United States Patent
Arienti et al.

(10) Patent No.: US 7,271,261 B2
(45) Date of Patent: Sep. 18, 2007

(54) SUBSTITUTED BENZIMIDAZOLES AND IMIDAZO-[4,5]-PYRIDINES

(75) Inventors: Kristen L. Arienti, La Mesa, CA (US); Frank U. Axe, Escondido, CA (US); J. Guy Breitenbucher, Escondido, CA (US); Liming Huang, San Diego, CA (US); Alice Lee, San Diego, CA (US); Kelly J. McClure, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 532 days.

(21) Appl. No.: 10/273,487

(22) Filed: Oct. 18, 2002

(65) Prior Publication Data

US 2003/0176438 A1   Sep. 18, 2003

Related U.S. Application Data

(60) Provisional application No. 60/330,304, filed on Oct. 18, 2001.

(51) Int. Cl.
*C07D 235/18* (2006.01)
*C07D 471/04* (2006.01)
*C07D 401/04* (2006.01)
*A61K 31/4184* (2006.01)

(52) U.S. Cl. ............ 544/139; 544/364; 544/370; 546/273.4; 548/309.7; 548/310.1; 548/310.4; 548/310.7; 548/311.7

(58) Field of Classification Search ......... 548/309.7, 548/310.1, 310.4, 310.7, 311.7; 546/273.4; 544/139, 364, 370; 514/234.5, 338, 253.01, 514/254.06, 394
See application file for complete search history.

(56) References Cited

U.S. PATENT DOCUMENTS 5,059,621 A   10/1991   Shroot et al. ............. 514/443

FOREIGN PATENT DOCUMENTS

| EP | 0148431 A1 | 7/1985 |
|---|---|---|
| EP | 0209707 A2 | 1/1987 |
| EP | 511187 | * 10/1992 |
| EP | 0719765 A2 | 7/1996 |
| WO | WO98/06703 A1 | 2/1998 |
| WO | WO99/11627 A1 | 3/1999 |
| WO | WO 99/30710 A | 6/1999 |
| WO | WO99/61019 A1 | 12/1999 |
| WO | WO99/61020 A1 | 12/1999 |
| WO | WO 00/26192 A | 6/2000 |
| WO | WO 01/00587 A | 1/2001 |
| WO | WO 01/53268 A | 7/2001 |
| WO | WO 01/74786 | * 10/2001 |
| WO | WO 01/98465 A1 | 12/2001 |

OTHER PUBLICATIONS

Bartek, DNA Damage Response: Mechanisms and Defects in Human Cancer, Jan. 2004.*
Simone, Oncology: Introduction, Cecil Textbook of Medicine, 20th Edition, vol. 1, pp. 1004-1010, 1996.*
Denny et al., Potential Antitumor Agents, Journal of Medicinal Chemistry, vol. 33, No. 2, pp. 814-819, 1990.*
Arienti, et al., Checkpoint Kinase Inhibitors; SAR and Radioprotective Properties of a Series of 2-Arylbenzimidazoles, J. Med. Chem., vol. 48, No. 6, pp. 1873-1885, 2005.*
Blasina, A. et al. A Human Homologue of the Checkpoint Kinase Cds 1 Directly Inhibits Cdc25 Phosphatase Curr. Biol. (1999) 9(1):1-10.
Buscemi, G. et al. Chk2 Activation Dependence on Nbs1 after DNA Damage Mol. Cell. Biol. (2001) 21(15):5214-5222.
Falck, J. et al. The ATM-Chk2-Cdc25A Checkpoint Pathway Guards against Radioresistant DNA Synthesis Nature (2001) 410:842-847.
Hirao, A. et al. Chk2 is a Tumor Suppressor That Regulates Apoptosis in both an Ataxia Telangiectasia Mutated (ATM)-Dependent and an ATM-Independent Manner Mol. Cell. Biol. (2002) 22(18):6521-6532.
Kim, J.S. et al. Structure-activity Relationships of Benzimidazoles and Related Heterocycles as Topoisomerase I Poisons Bioorg. Med. Chem. (1996) 4(4):621-630.
Lee, J. S. et al. hCds1-Mediated Phosphorylation of BRCA1 Regulates the DNA Damage Response Nature (2000) 404:201-204.
Matsuoka, S. et al. Linkage of ATM to Cell Cycle Regulation by the Chk2 Protein Kinase Science (1998) 282:1893-1897.
Takai, H. et al. Chk2-Deficient Mice Exhibit Radioresistance and Defective p53-Mediated Transcription EMBO J. (2002) 21(19):5195-5205.
Tominaga K. et al. Role of Human Cds1 (Chk2) Kinase in DNA Damage Checkpoint and Its Regulation by p53 J. Biol. Chem. (1999) 274(44):31463-31467.
White, A.W. et al Resistance-Modifying Agents. 9 Synthesis and Biological Properties of Benzimidazole Inhibitors of the DNA Repair Enzyme Poly(ADP-ribose) Polymerase J. Med. Chem. (2000) 43(22):4084-4097.

* cited by examiner

*Primary Examiner*—Deepak Rao
(74) *Attorney, Agent, or Firm*—John Harbour

(57) ABSTRACT

2-Aryl substituted benzimidazoles and imidazo[4,5]pyridines are disclosed as inhibitors of Cds1 and useful as adjuvants to chemotherapy or radiation therapy in the treatment of cancer.

18 Claims, No Drawings

SUBSTITUTED BENZIMIDAZOLES AND IMIDAZO-[4,5]-PYRIDINES

This application claims the benefit for the purpose of priority of U.S. Provisional Application No. 60/330,304, filed on Oct. 18, 2001.

FIELD OF THE INVENTION

The present invention relates to substituted benzimidazole and imidazo-[4,5]-pyridine compounds, compositions containing them, and methods of using them.

BACKGROUND OF THE INVENTION

The maintenance of an intact genome is of crucial importance to every organism. The individual cell in a multicellular eukaryotic organism possesses sophisticated and intricate mechanisms to properly respond to DNA damage. Such mechanisms repair damaged DNA or trigger programmed cell death (apoptosis). In response to DNA damage, checkpoint kinases are thought to be intimately involved in these processes. These kinases are activated by upstream proteins, such as ATM (ataxia-telangiectasia mutated) and ATR (ataxia-telangiectasia mutated and rad3-related), and in turn trigger cell cycle arrest by inhibition of proteins such as Cdc25A or Cdc25C. The checkpoint kinases may also modulate the activity of other proteins that are thought to be involved in DNA repair and programmed cell death. Examples of such proteins are BRCA1 and p53.

The checkpoint kinase Cds1 (in man also known as Chk2) is conserved from yeast to man. A human homolog of the *Schizosaccharomyces pombe* Cds1 gene has been described (Tominaga, K. et al. *J. Biol. Chem.* 1999, 274(44):31463-31467; Matsouka, S. et al. *Science* 1998, 282:1893-1897; Blasina, A. et al. *Curr. Biol.* 1999, 9(1):1-10). Human Cds1 was rapidly activated by phosphorylation in response to DNA damage in both normal cells and in p53-deficient cancer cells. High levels of hCds1 were observed in p53-deficient cells. In human cells Cds1 has been implicated in the regulation by phosphorylation of proteins such as p53, BRCA1, Cdc25A, and Cdc25C (See: Lee, J. -S. et al. *Nature* 2000, 404:201-204; Falck, J. et al. *Nature* 2001, 410:842-847; and Buscemi, G. et al. *Mol. Cell. Biol.* 2001, 21(15): 5214-5222). As described below, inhibition of Cds1 offers two strategies for improving the effectiveness of DNA-damaging cancer treatments.

Cancer cells are often deficient in the mechanisms responsible for maintaining an intact genome. In particular, they have often lost proper p53 function, which generally correlates with the progression of a tumor to a more aggressive state, such as the progression from a preinvasive to invasive stage of colon cancer, or from a low grade to a high grade astrocytoma. Between 30% and 70% of all subtypes of tumors have a point mutation in one of the two p53 gene copies and have lost the other allele. P53-deficient cells are generally more resistant to radiation. It is thought that the lack of initiation of programmed cell death in cancer cells may render such cells less sensitive to DNA-damaging cancer treatments. The transcription factor p53 is of importance not only for the initiation of programmed cell death, but also in cell cycle arrest. Loss of p53 function may therefore leave cancer cells with limited protection against insult to the genome. Further disruption of DNA damage repair and cell cycle arrest by inhibition of kinases such as Cds1 could then render cancer cells unable to survive after DNA damage. Therefore inhibition of Cds1 could, by removing the remaining components of DNA damage repair, render the cancer cells more susceptible to treatments such as chemical DNA-damaging agents or ionizing radiation.

Normal cells, on the other hand, have an intact p53 system, and will often undergo apoptosis in response to DNA-damaging treatments at a much lower dose than that required to kill cancer cells. Therefore, in such situations, normal cells will be at a disadvantage compared to cancer cells, and cancer treatments often have to be discontinued due to serious side effects caused by loss of normal cells before the cancer has been eradicated. Inhibition of Cds1, which would prevent this kinase from phosphorylating and thereby stabilizing p53, could therefore protect normal cells from the effects of ionizing radiation or DNA-damaging chemotherapeutics while still allowing these agents to be effective against p53-deficient cancer cells. This would have the effect of increasing the therapeutic potential of these agents. This view is supported by studies of mice deficient in Cds1 (See: Hirao, A. et al. *Mol. Cell. Biol.* 2002, 22(18): 6521-6532; Takai, H. et al. EMBO J. 2002, 21(19):5195-5205; WO 01/98465 A1 Chugai Seiyaku Kabushiki Kaisha, Dec. 27, 2001). These animals showed increased resistance to the apoptosis caused by ionizing radiation over their wild-type counterparts. For example, it was shown that these animals were protected from apoptosis of intestinal cells, hair follicle cells, cells of the CNS, and thymus cells relative to their wild-type counterparts when treated with ionizing radiation. Cds1 knockout animals also showed increased survival when exposed to ionizing radiation. It is therefore logical to assume that chemical inhibitors of Cds1 would have therapeutic potential in the protection of patients from the deleterious side effects of radiation or DNA-damaging chemotherapeutics.

Additional examples of cell cycle checkpoint modulators in development include UCN-01 (CAS 112953-11-4), UCN—$O_2$, KW-2401, NSC-638850 (Kyowa Hakko/National Cancer Institute) and SB-218078 (CAS 135897-06-2) (SmithKline Beecham).

Publications that may be considered as potential prior art with respect to one or more of the compounds of the invention include DE 0148431 (T 7570), WO 01/21771 A2, and White, A. W. et al. *J. Med. Chem.* 2000, 43(22):4084-4097.

It is an object of the present invention to provide a Cds1-inhibiting adjuvant for use with ionizing radiation in the treatment of cancers.

It is another object of the present invention to provide a Cds1-inhibiting adjuvant for use with DNA-damaging chemotherapeutics in the treatment of cancers.

It is still another object of the present invention to provide a Cds1-inhibiting adjuvant for use with ionizing radiation and/or DNA-damaging chemotherapeutics that promotes the death of cancer cells damaged by such radiation or chemotherapeutics.

It is yet another object of the present invention to provide a Cds1-inhibiting adjuvant for use with ionizing radiation and/or DNA-damaging chemotherapeutics that prevents apoptosis of healthy cells damaged by such radiation or chemotherapeutics.

It is also an object of the present invention to provide a Cds1-inhibiting adjuvant for use with ionizing radiation and/or DNA-damaging chemotherapeutics that both promotes in a patient the death of cancer cells and prevents the apoptosis of healthy cells damaged by such radiation or chemotherapeutics.

It is also another object of the present invention to provide a Cds1-inhibiting adjuvant for use with ionizing radiation and/or DNA-damaging chemotherapeutics in the treatment of p53-deficient cancer cells.

It is an additional object of the present invention to provide a Cds1-inhibiting adjuvant for use with ionizing radiation and/or DNA-damaging chemotherapeutics that both promotes in a patient the death of p53-deficient cancer cells and prevents the apoptosis of healthy cells damaged by such radiation or chemotherapeutics.

It is an object of the present invention to provide a method for the treatment of cancer in a patient comprising exposing the cancer to ionizing radiation and administering a Cds1-inhibiting adjuvant.

It is another object of the present invention to provide a method for the treatment of cancer in a patient comprising administering a DNA-damaging chemotherapeutic and a Cds1-inhibiting adjuvant.

It is still another object of the present invention to provide a method to promote in a patient the death of cancer cells damaged by exposure to ionizing radiation and/or by administration of a DNA-damaging chemotherapeutic comprising the step of administering a Cds1-inhibiting adjuvant in conjunction with such therapies.

It is yet another object of the present invention to provide a method to prevent in a patient the apoptosis of healthy cells damaged by exposure to ionizing radiation and/or by administration of a DNA-damaging chemotherapeutic comprising the step of administering a Cds1-inhibiting adjuvant in conjunction with such therapies.

It is also an object of the present invention to provide a method to both promote in a patient the death of cancer cells and prevent the apoptosis of healthy cells damaged by exposure to ionizing radiation and/or by administration of a DNA-damaging chemotherapeutic comprising the step of administering a Cds1-inhibiting adjuvant in conjunction with such therapies.

It is also another object of the present invention to provide a method for the treatment of p53-deficient cancer cells in a patient comprising exposing the cancer cells to ionizing radiation and/or administering a DNA-damaging chemotherapeutic and administering a Cds1-inhibiting adjuvant.

It is an additional object of the present invention to provide a method to both promote in a patient the death of p53-deficient cancer cells and to prevent the apoptosis of healthy cells damaged by exposure to ionizing radiation and/or by administration of a DNA-damaging chemotherapeutic comprising the step of administering a Cds1-inhibiting adjuvant in conjunction with such therapies.

SUMMARY OF THE INVENTION

The present invention features compounds of formula (I):

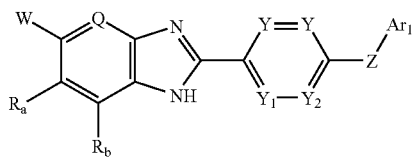

wherein
W is COOH, —(CO)NHR$^1$, or —(SO$_2$)NHR$^1$;
R$^1$ is H or C$_{1-4}$alkyl;
Q is N or CH;
R$_a$ and R$_b$ are H or halogen;
Y, Y$_1$ and Y$_2$ are independently selected from N and C—R$_c$ with the proviso that 0, 1 or 2 of Y, Y$_1$ and Y$_2$ are N and at least 2 of R$_c$ must be hydrogen;
R$_c$ are independently selected from the group consisting of —H, —OH, —C$_{1-6}$alkyl, —SCF$_3$, halo, —CF$_3$ and —OCF$_3$;
Z is selected from the group consisting of O, S, SO, SO$_2$, SO$_2$NR 2, NR$^2$SO$_2$, NH, CONR, piperazin-diyl or a covalent bond;
R$^2$ is H or C$_{1-4}$alkyl;
Ar$_1$ is selected from the group consisting of:
 a) phenyl, optionally mono-, di- or tri-substituted with R$^p$;
  R$^p$ is selected from the group consisting of —OH, —C$_{1-6}$alkyl, —OC$_{1-6}$alkyl, —C$_{3-6}$cycloalkyl, —OC$_{3-6}$cycloalkyl, —CN, —NO$_2$, —N(R$^y$)R$^z$ (wherein R$^y$ and R$^z$ are independently selected from H or C$_{1-6}$alkyl, or may be taken together with the nitrogen of attachment to form an otherwise aliphatic hydrocarbon ring, said ring having 5 to 7 members, optionally having one carbon replaced with >O, =N—, >NH or >N(C$_{1-4}$alkyl) and optionally having one or two unsaturated bonds in the ring), —(C=O)N(R$^y$)R$^z$, —(N—R$^t$)COR$^t$ (wherein R$^t$ is independently H or C$_{1-6}$alkyl), —(N—R$^r$)SO$_2$C$_{1-6}$alkyl, —(C=O)C$_{1-6}$alkyl, —(S=(O)n)—C$_{1-6}$alkyl (wherein n is selected from 0, 1 or 2), —SO$_2$N(R$^y$)R$^z$, —SCF$_3$, halo, —CF$_3$, —OCF$_3$, —COOH, —C$_{1-6}$ alkylCOOH, —COOC$_{1-6}$alkyl and —C$_{1-6}$alkylCOOC$_{1-6}$alkyl;
 b) phenyl, attached at two adjacent ring members to a C$_{3-5}$alkyl moiety to form a fused 5 to 7 membered ring, said fused ring optionally having a second unsaturated bond, said fused ring optionally having one or two members replaced with, =N—, >O, >NH or >N(C$_{1-4}$alkyl) except that no such replacement is permitted where the fused ring is 5 membered and has a second unsaturated bond, and said fused ring optionally having one carbon member replaced with >C=O, the fused rings optionally mono-, di- or tri-substituted with R$^p$;
 c) a monocyclic aromatic hydrocarbon group having six ring carbon atoms, having a carbon atom which is the point of attachment, having one or two carbon atoms replaced by N, and optionally mono- or di-substituted with R$^p$;
 d) a monocyclic aromatic hydrocarbon group having six ring carbon atoms, having a carbon atom which is the point of attachment, having zero, one or two carbon atoms replaced by N, and having attachment at two adjacent carbon ring members to a three membered hydrocarbon moiety to form a fused five membered aromatic ring, which moiety has one carbon atom replaced by >O, >S, >NH or >N(C$_{1-4}$alkyl) and which moiety has up to one additional carbon atom optionally replaced by N, the fused rings optionally mono-, di- or tri-substituted with R$^p$;
 e) a monocyclic aromatic hydrocarbon group having six ring carbon atoms, having a carbon atom which is the point of attachment, having zero, one or two carbon atoms replaced by N, and having attachment at two adjacent carbon ring members to a four membered hydrocarbon moiety to form a fused six membered aromatic ring, which moiety has zero, one or two carbon atoms replaced by N, the fused rings optionally mono-, di- or tri-substituted with R$^p$;

f) a monocyclic aromatic hydrocarbon group having five ring carbon atoms, having a carbon atom which is the point of attachment, having one carbon atom replaced by >O, >S, >NH or >N($C_{1-4}$alkyl), having up to one additional carbon atom optionally replaced by N, and optionally mono- or di-substituted with $R^p$;

g) a monocyclic aromatic hydrocarbon group having five ring carbon atoms, having a carbon atom which is the point of attachment, having one carbon atom replaced by >O, >S, >NH or >N($C_{1-4}$alkyl), and having attachment at two adjacent carbon ring members to a four membered hydrocarbon moiety to form a fused six membered aromatic ring, which moiety has zero, one or two carbon atoms replaced by N, the fused rings optionally mono-, di- or tri-substituted with $R^p$; and and enantiomers, diastereomers and pharmaceutically acceptable salts, esters or amides thereof.

In one aspect, the invention provides a method for treating a subject suffering from cancer, said method comprising administering to said subject a therapeutically effective amount of a pharmaceutical composition comprising a compound of formula (I). According to one aspect, the cancer is p-53 deficient.

In another aspect, the invention provides a method for treating a subject suffering from a p53-deficient tumor, said method comprising (a) administering to said subject a therapeutically effective amount of a pharmaceutical composition comprising a compound of formula (I) and (b) damaging the DNA of said subject, for example, by administration of a DNA-damaging treatment or agent, such as ionizing radiation or a chemical agent that causes DNA damage. In one aspect, the DNA damaging treatment is provided such that administration of the compound of formula (I) provides effective serum levels of the compound of formula (I) during the treatment and 12 hours to 5 days thereafter, for example, 1-2 days thereafter. In a further aspect, the method of treatment further includes administration of one or more additional anti-cancer agents, to provide in total three or four (or more) agents, to be administered in an effective anti-cancer amount. Multiple or combination therapies may allow use of lower amounts of one or more of the individual agents, when compared with monotherapy, and thereby reducing the incidence or degree of adverse effects.

Examples of such DNA-damaging chemical agents are compounds that cause DNA strand breaks directly such as bleomycin. DNA damage may also be caused by alkylating agents such as hexamethylamine, busulfan, carboplatin, carmustine, cisplatinum, cyclophosphamide, dacarbazine, ifosfamide, lomustine, mechlorethamine, melphalan, procarbazine, streptozocin or thiotepa, or combinations thereof. DNA damage may also be caused indirectly by topoisomerase inhibitors such as etoposide, irinotecan, teniposide, topotecan, and doxorubicin or by antimetabolites such as cladribine, cytarabine, floxuridine, 5-fluorouracil, gemcitibine, hydroxyurea, mercaptopurine, methotreaxate, pentostatin, thioguanine, and triemtrexate. Enhancement of DNA damaging effects and improved therapeutic responses can be obtained by combining anticancer agents such as those exemplified above.

A third aspect of the invention provides the use, or the use for the manufacture of a medicament, of a disclosed compound for treating a tumor, in particular, a p53 deficient tumor, and more in particular, a tumor selected from lung, prostate, colon, brain, head and neck, and breast. Other tumors include tumors of the stomach, liver, and ovary. A p-53 deficient tumor is a tumor wherein the functions mediated by p53 are lacking or suppressed due to genetic mutations in the gene encoding p53 or through deficiencies or disregulation of proteins that modulate p53 expression levels and function. Examples of such proteins are MDM2 and p14(ARF). A further aspect of the invention includes the treatment of a late-stage, e.g., stage 3 or stage 4, tumor.

The invention also features anti-cancer pharmaceutical compositions comprising as active ingredient an effective amount of a disclosed compound of formula (I), and a pharmaceutically acceptable carrier. The active ingredient can be formulated in any manner suitable for the particular tumor, including aerosol, oral, injectable and topical formulations, and time-release formulations thereof.

Additional features and advantages of the invention will become apparent from the detailed description and examples below, and the appended claims.

DETAILED DESCRIPTION OF THE INVENTION

Preferably W is COOH, —(CO)NHCH$_3$, —(CO)NH$_2$, —(SO$_2$)NHCH$_3$ or —(SO$_2$)NH$_2$.

More preferably W is COOH, —(CO)NH$_2$ or —(SO$_2$)NH$_2$.

Preferably $R_a$ and $R_b$ are H, Cl or F.

More preferably, $R_a$ is H and $R_b$ is Cl or F.

Most preferably $R_a$ and $R_b$ are H.

Preferably Y, $Y_1$ and $Y_2$ are independently selected from N and C—$R_c$ with the proviso that 0 or 1 of $Y_2$ is N.

Most preferably Y, $Y_1$ and $Y_2$ are C—$R_c$.

Preferably $R_c$ is selected from the group consisting of —H, —OH, —CH$_3$, —CH$_2$CH$_3$, —SCF$_3$, —F, —Cl, —Br, I, —CF$_3$ and —OCF$_3$.

Most preferably $R_c$ is selected from the group consisting of H, F, Cl, CH$_3$, OCH$_3$.

Preferably Z is selected from the group consisting of O, S, SO, SO$_2$, SO$_2$NH, SO$_2$NCH$_3$, NHSO$_2$, NCH$_3$SO$_2$, NH, CONH, CONCH$_3$, piperazin-1,4-diyl and a covalent bond.

More preferably Z is selected from the group consisting of O, S, SO, SO$_2$, SO$_2$NH, NHSO$_2$, NH and CONH.

Most preferably Z is selected from the group consisting of O, S, SO, SO$_2$ and SO$_2$NH.

Preferably Ar$_1$, optionally substituted with $R^p$ as described above, is selected from the group consisting of:

a) phenyl, b) tetralin-5,6,7 or 8-yl, chroman-5,6,7 or 8-yl, benzo-1,2-pyran-5,6,7 8-yl, benzo-2,3-pyron-5,6,7 or 8-yl, coumarin-5,6,7 or 8-yl, isocoumarin-5,6,7 or 8-yl, benzo-1,3,2-benzoxazin-5,6,7 or 8-yl, benzo-1,4-dioxan-5,6,7 or 8-yl, 1,2,3,4-tetrahydroquinolin-5,6,7 or 8-yl, 1,2,3,4-tetrahydroquinoxalin-5,6,7 or 8-yl, thiochroman-5,6,7 or 8-yl, 2,3-dihydrobenzo[1,4]dithiin-5,6,7 or 8-yl, 1,2,3,4-tetrahydroisoquinolin-5, 6,7 or 8-yl, indene-4,5,6, or 7-yl, 1,2,3,4-tetrahydronapth-5,6,7, or 8 yl, 1,2-dihydroisoindolo-4,5,6, or 7-yl, 2,3-dihydroindene-4,5,6, or 7-yl, benzo-1,3-dioxol-4,5,6 or 7-yl, 2,3-dihydroindol-4,5,6 or 7-yl, 2,3-dihydrobenzofuran-4,5,6 or 7-yl, 2,3-dihydrobenzothiophen-4,5,6 or 7-yl, 2,3-dihydrobenzoimidazol-4,5,6 or 7-yl, c) pyridinyl, pyrazinyl, pyrimidinyl, pyridazinyl, d) benzoxazol-4,5,6 or 7-yl, benzothiophen-4,5,6 or 7-yl, benzofuran-4,5,6 or 7-yl, indol-4,5,6 or 7-yl, benzthiazo-4,5,6 or 7-yl, benzimidazo-4,5,6 or 7-yl, indazol-4,5,6 or 7-yl, 1H-pyrrolo[2,3-b]pyridin-4,5 or 6-yl, 1H-pyrrolo[3,2-c]pyridin-4,6 or 7-yl, 1H-pyrrolo[2,3-c]pyridin-4,5 or 7-yl, 1H-pyrrolo[3,2-b]pyridin-5,6 or 7-yl, purin-2-yl, e) isoquinolin-5,6,7 or 8-yl, quinolin-5,6,7 or 8-yl, quinoxalin-5,6,7 or 8-yl, quinazolin-5,6,7 or 8-yl, naphthyridinyl,
f) furanyl, oxazolyl, isoxazolyl, thiophenyl, thiazolyl, isothiazolyl, pyrrolyl, imidazolyl, pyrazolyl, and
g) benzoxazol-2-yl, benzothiophen-2 or 3-yl, benzofuran-2 or 3-yl, indol-2 or 3-yl, benzthiazol-2-yl, benzimidazo-2-yl, indazol-3-yl, 1H-pyrrolo[2,3-b]pyridin-2 or 3-yl, 1H-pyrrolo[3,2-c]pyridin-2 or 3-yl, 1H-pyrrolo[2,3-c]pyridin-2 or 3-yl, 1H-pyrrolo[3,2-b]pyridin-2 or 3-yl, purin-8-yl.

More preferably $Ar_1$, optionally substituted with $R^p$ as described above, is selected from the group consisting of:
a) phenyl,
b) coumarin-5,6,7 or 8-yl, benzo-1,4-dioxan-5,6,7 or 8-yl, 1,2,3,4-tetrahydroquinolin-5,6,7 or 8-yl, or 8-yl, 1,2,3,4-tetrahydroisoquinolin-5,6,7 or 8-yl, indene-4,5,6, or 7-yl, 1,2,3,4-tetrahydronapth-5,6,7, or 8 yl, 1,2-dihydroisoindolo-4,5,6, or 7-yl, 2,3-dihydroindene-4,5,6, or 7-yl, benzo-1,3-dioxol-4,5,6 or 7-yl, 2,3-dihydroindol-4,5,6 or 7-yl, 2,3-dihydrobenzofuran-4,5,6 or 7-yl, 2,3-dihydrobenzothiophen-4,5,6 or 7-yl,
c) pyridinyl, pyrazinyl, pyrimidinyl, pyridazinyl,
d) benzothiophen-4,5,6 or 7-yl, benzofuran-4,5,6 or 7-yl, indol-4,5,6 or 7-yl,
e) isoquinolin-5,6,7 or 8-yl, quinolin-5,6,7 or 8-yl,
f) furanyl, oxazolyl, isoxazolyl, thiophenyl, thiazolyl, isothiazolyl, pyrrolyl, imidazolyl, pyrazolyl, and
g) benzoxazol-2-yl, benzothiophen-2 or 3-yl, benzofuran-2 or 3-yl, indol-2 or 3-yl.

Most preferably $Ar^1$, optionally substituted with $R^p$ as described above, is selected from the group consisting of: phenyl, benzo-1,4-dioxan-5,6,7 or 8-yl, indene-4,5,6, or 7-yl, 1,2,3,4-tetrahydronapth-5,6,7, or 8 yl, 2,3-dihydroindene-4,5,6, or 7-yl, benzo-1,3-dioxol-4,5,6 or 7-yl, 2,3-dihydroindol-4,5,6 or 7-yl, 2,3-dihydrobenzofuran-4,5,6 or 7-yl, 2,3-dihydrobenzothiophen-4,5,6 or 7-yl, pyridinyl, benzothiophen-4,5,6 or 7-yl, benzofuran-4,5,6 or 7-yl, indol-4,5,6 or 7-yl, furanyl, thiophenyl, pyrrolyl, pyrazolyl, and benzothiophen-2 or 3-yl, benzofuran-2 or 3-yl and indol-2 or 3yl.

Specific $Ar_1$, including the $R^p$ substituent, are selected from the group consisting of pyridyl, phenyl, naphthyl, 4-chloro phenyl, 4-methyl-3-chloro phenyl, 4-chloro-3-trifluoromethyl phenyl, 3,4-dichloro phenyl, 3-chloro-4-fluoro phenyl, 2-flouro-5-trifluoromethyl, 4-chloro-3-fluoro phenyl, 3,4-dimethyl phenyl, 2-napthyl, 4-trifluoromethyl phenyl, 4-bromo phenyl, 4-fluoro-3-methyl phenyl, 3-chloro phenyl, tetrahydronapthyl, 5-chloro-2-methyl phenyl, 3-trifluoromethyl phenyl, 4-methoxy phenyl, 4-methyl phenyl, 2-fluoro-3-trifluoromethyl phenyl, 2-chloro-4-methyl phenyl, 4-ethyl phenyl, 4-fluoro phenyl, 3,4-dimethoxy phenyl, 3-(dimethylamino) phenyl, 4-nitro phenyl, 4-cyano phenyl, 2-methoxy-4-methyl phenyl, 4-trifluoromethoxy phenyl, 2-chloro phenyl, 4-morpholino phenyl, 3-chloro phenyl, 2,3-dichloro phenyl, benzo[1,3]dioxolyl, 4-amino phenyl, 4-hydroxy phenyl, 4-bromo-3-hydroxy phenyl, 4-chloro-2-hydroxy phenyl, 4-chloro-3-hydroxy phenyl, 2,4-dichloro phenyl, 4-bromo-3-methoxy phenyl and 4-iodo phenyl.

Preferably $R^p$ is selected from the group consisting of —OH, —CH$_3$, —CH$_2$CH$_3$, —OCH$_3$, —OCH$_2$CH$_3$, —OCH(CH$_3$)$_2$, cyclopropyl, cyclobutyl, cyclopentyl, cyclohexyl, -Ocyclopentyl, -Ocyclohexyl, —CN, —NO$_2$, —C(O)NH$_2$, —C(O)N(CH$_3$)$_2$, —C(O)NH(CH$_3$), —NHCOCH$_3$, —NCH$_3$COCH$_3$, —NHSO$_2$CH$_3$, —NCH$_3$SO$_2$CH$_3$, —C(O)CH$_3$, —SOCH$_3$, —SO$_2$CH$_3$, —SO$_2$NH$_2$, —SO$_2$NHCH$_3$, —SO$_2$N(CH$_3$)$_2$, —SCF$_3$—F, —Cl, —Br, I, —CF$_3$, —OCF$_3$, —COOH, —COOCH$_3$, —COOCH$_2$CH$_3$, —NH$_2$, —NHCH$_3$, —N(CH$_3$)$_2$, —N(CH$_2$CH$_3$)$_2$, —NCH$_3$(CH(CH$_3$)$_2$), imidazolidin-1-yl, 2-imidazolin-1-yl, pyrazolidin-1-yl, piperidin-1-yl, 2- or 3-pyrrolin-1-yl, 2-pyrazolinyl, morpholin-4-yl, thiomorpholin-4-yl, piperazin-1-yl, pyrrolidin-1-yl, homopiperidin-1-yl.

Most preferably $R^p$ is selected from the group consisting of H, —OH, OCH$_3$, OCF$_3$, —CH$_3$, —CH$_2$CH$_3$, —CF$_3$, —F, —Cl, —Br, —I, —NH$_2$, —N(CH$_3$)$_2$, morpholin-4-yl, —NO$_2$, CN, —C(O)NH$_2$, —COOH, —NHSO$_2$CH$_3$, —SO$_2$NH$_2$.

The invention features pharmaceutically active, substituted benzimidazole compounds as disclosed in the Summary section above.

A. Terms

The following terms are defined below and by their usage throughout this disclosure.

"Alkyl" includes optionally substituted straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl includes cycloalkyl, such as cyclopropyl, cyclobutyl, cyclopentyl, and cyclohexyl.

"Alkenyl" includes optionally substituted straight chain and branched hydrocarbon radicals as above with at least one carbon-carbon double bond (sp$^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention.

"Alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

"Alkoxy" includes an optionally substituted straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and SO$_2$. Heteroalkyl includes alkoxy, aminoalkyl, thioalkyl, and so on.

"Aryl" includes phenyl, naphthyl, biphenylyl, tetrahydronaphthyl, and so on, any of which may be optionally substituted. Aryl also includes arylalkyl groups such as benzyl, phenethyl, and phenylpropyl. Aryl includes a ring system containing an optionally substituted 6-membered carbocyclic aromatic ring, said system may be bicyclic, bridge, and/or fused. The system may include rings that are aromatic, or partially or completely saturated. Examples of ring systems include indenyl, pentalenyl, 1-4-dihydronaphthyl, indanyl, benzimidazolyl, benzothiophenyl, indolyl, benzofuranyl, isoquinolinyl, and so on.

"Heterocyclyl" includes optionally substituted aromatic and nonaromatic rings having carbon atoms and at least one heteroatom (O, S, N) or heteroatom moiety (SO$_2$, CO, CONH, COO) in the ring. Unless otherwise indicated, a heterocyclic radical may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 4 and 7 ring atoms, or between 5 and 6 ring atoms; there may be between 1 and 5 heteroatoms or heteroatom moieties in the ring, and preferably between 1 and 3. A heterocyclyl may be saturated, unsaturated, aromatic (e.g., heteroaryl), nonaromatic, or fused.

Heterocyclyl also includes fused, e.g., bicyclic, rings, such as those optionally condensed with an optionally substituted carbocyclic or heterocyclic five- or six-membered aromatic ring. For example, "heteroaryl" includes an optionally substituted six-membered heteroaromatic ring containing 1, 2 or 3 nitrogen atoms condensed with an optionally substituted five- or six-membered carbocyclic or heterocyclic aromatic ring. Said heterocyclic five- or six-membered aromatic ring condensed with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

Examples of heterocyclyls include thiazolyl, furyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imdazolidinyl, imidazolinyl, pyrazolidinyl, pyrazolinyl, piperidyl, piperazinyl, indolinyl, and morpholinyl. For example, preferred heterocyclyls or heterocyclic radicals include morpholinyl, piperazinyl, pyrrolidinyl, pyridyl, cyclohexylimino, cycloheptylimino, and more preferably, piperidyl.

Examples illustrating heteroaryl are thienyl, furanyl, pyrrolyl, imidazolyl, oxazolyl, thiazolyl, benzothienyl, benzofuranyl, benzimidazolyl, benzoxazolyl, benzothiazolyl.

"Acyl" refers to a carbonyl moiety attached to either a hydrogen atom (i.e., a formyl group) or to an optionally substituted alkyl or alkenyl chain, or heterocyclyl.

"Halo" or "halogen" includes fluoro, chloro, bromo, and iodo, and preferably chloro or bromo as a substituent.

"Alkanediyl" or "alkylene" represents straight or branched chain optionally substituted bivalent alkane radicals such as, for example, methylene, ethylene, propylene, butylene, pentylene or hexylene.

"Alkenediyl" represents, analogous to the above, straight or branched chain optionally substituted bivalent alkene radicals such as, for example, propenylene, butenylene, pentenylene or hexenylene. In such radicals, the carbon atom linking a nitrogen preferably should not be unsaturated.

"Aroyl" refers to a carbonyl moiety attached to an optionally substituted aryl or heteroaryl group, wherein aryl and heteroaryl have the definitions provided above. In particular, benzoyl is phenylcarbonyl.

As defined herein, two radicals, together with the atom(s) to which they are attached may form an optionally substituted 4- to 7-, 5- to 7-, or a 5- to 6-membered ring carbocyclic or heterocyclic ring, which ring may be saturated, unsaturated or aromatic. Said rings may be as defined above in the Summary of the Invention section. Particular examples of such rings are as follows in the next section.

"Pharmaceutically acceptable salts, esters, and amides" include carboxylate salts (e.g., $C_{1-8}$ alkyl, $C_{3-8}$ cycloalkyl, aryl, $C_{2-10}$ heteroaryl, or $C_{2-10}$ non-aromatic heterocyclic) amino acid addition salts, esters, and amides that are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66:1-19, which is incorporated herein by reference. Representative pharmaceutically acceptable amides of the invention include those derived from ammonia, primary $C_{1-6}$ alkyl amines and secondary di ($C_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di ($C_{1-2}$ alkyl)amines. Representative pharmaceutically acceptable esters of the invention include $C_{1-7}$ alkyl, $C_{5-7}$ cycloalkyl, phenyl, and phenyl ($C_{1-6}$)alkyl esters. Preferred esters include methyl esters.

"Patient" or "subject" includes mammals such as humans and animals (dogs, cats, horses, rats, rabbits, mice, non-human primates) in need of observation, experiment, treatment or prevention in connection with the relevant disease or condition. Preferably, the patient or subject is a human.

"Composition" includes a product comprising the specified ingredients in the specified amounts as well as any product that results directly or indirectly from combinations of the specified ingredients in the specified amounts.

"Therapeutically effective amount" or "effective amount" means that amount of active compound or pharmaceutical agent that elicits the biological or medicinal response in a tissue system, animal or human that is being sought by a researcher, veterinarian, medical doctor or other clinician, which includes alleviation of the symptoms of the condition or disorder being treated.

Concerning the various radicals in this disclosure and in the claims, three general remarks are made. The first remark concerns valency. As with all hydrocarbon radicals, whether saturated, unsaturated or aromatic, and whether or not cyclic, straight chain, or branched, and also similarly with all heterocyclic radicals, each radical includes substituted radicals of that type and monovalent, bivalent, and multivalent radicals as indicated by the context of the claims. The context will indicate that the substituent is an alkylene or hydrocarbon radical with at least two hydrogen atoms removed (bivalent) or more hydrogen atoms removed (multivalent). An example of a bivalent radical linking two parts of the molecule is Z in formula (I), which links X and $Ar_1$.

Second, radicals or structure fragments as defined herein are understood to include substituted radicals or structure fragments. Hydrocarbyls include monovalent radicals containing carbon and hydrogen such as alkyl, alkenyl, alkynyl, cycloalkyl, and cycloalkenyl (whether aromatic or unsaturated), as well as corresponding divalent radicals such as alkylene, alkenylene, phenylene, and so on. Heterocarbyls include monovalent and divalent radicals containing carbon, hydrogen, and at least one heteroatom. Examples of monovalent heterocarbyls include acyl, acyloxy, alkoxyacyl, heterocyclyl, heteroaryl, aroyl, benzoyl, dialkylamino, hydroxyalkyl, and so on. Using "alkyl" as an example, "alkyl" should be understood to include substituted alkyl having one or more substitutions, such as between 1 and 5, 1 and 3, or 2 and 4 substituents. The substituents may be the same (dihydroxy, dimethyl), similar (chlorofluoro), or different (chlorobenzyl- or aminomethyl-substituted).

Examples of substituted alkyl include haloalkyl (such as fluoromethyl, chloromethyl, difluoromethyl, perchloromethyl, 2-bromoethyl, perfluoromethyl, and 3-iodocyclopentyl), hydroxyalkyl (such as hydroxymethyl, hydroxyethyl, 2-hydroxypropyl, aminoalkyl (such as aminomethyl, 2-aminoethyl, 3-aminopropyl, and 2-aminopropyl), nitroalkyl, alkylalkyl, and so on. A di($C_{1-6}$ alkyl)amino group includes independently selected alkyl groups, to form, for example, methylpropylamino and isopropylmethylamino, in addition dialkylamino groups having two of the same alkyl group such as dimethyl amino or diethylamino.

Third, only stable compounds are intended. For example, where there is an NR'R" group, and R can be an alkenyl group, the double bond is at least one carbon removed from the nitrogen to avoid enamine formation. Similarly, where a dashed line is an optional $sp^2$ bond, if it is absent, the appropriate hydrogen atom(s) is(are) included.

Compounds of the invention are further described in the next section.

B. Compounds

The invention features the treatment, or inhibition of onset or progression, of cancer using one or more Cds1 inhibitors as described in the Summary section.

Preferred compounds of Formula I were made as described in Examples 1-100 and are selected from the group consisting of:

| EX | Compound Name |
|---|---|
| 1 | 2-[4-(4-chloro-phenoxy)-phenyl]-1H-benzoimidazole-5-carboxylic acid amide |
| 2 | 2-[4-(3-chloro-4-methyl-phenoxy)-phenyl]-1H-benzoimidazole-5-carboxylic acid amide |
| 3 | 2-[4-(4-chloro-3-trifluoromethyl-phenoxy)-phenyl]-1H-benzoimidazole-5-carboxylic acid amide |
| 4 | 2-[4-(3,4-dichloro-phenoxy)-phenyl]-1H-benzoimidazole-5-carboxylic acid amide |
| 5 | 2-[4-(3-chloro-4-fluoro-phenoxy)-phenyl]-1H-benzoimidazole-5-carboxylic acid amide |
| 6 | 2-[4-(2-fluoro-5-trifluoromethyl-phenoxy)-phenyl]-1H-benzoimidazole-5-carboxylic acid amide |
| 7 | 2-[4-(4-chloro-3-fluoro-phenoxy)-phenyl]-1H-benzoimidazole-5-carboxylic acid amide |
| 8 | 2-[4-(3,4-dimethyl-phenoxy)-phenyl]-1H-benzoimidazole-5-carboxylic acid amide |
| 9 | 2-[4-(2-naphthyloxy)-phenyl]-1H-benzoimidazole-5-carboxylic acid amide |
| 10 | 2-[4-(4-trifluoromethyl-phenoxy)-phenyl]-1H-benzoimidazole-5-carboxylic acid amide |
| 11 | 2-[4-(4-bromo-phenoxy)-phenyl]-1H-benzoimidazole-5-carboxylic acid amide |
| 12 | 2-[4-(4-fluoro-3-methyl-phenoxy)-phenyl]-1H-benzoimidazole-5-carboxylic acid amide |
| 13 | 2-[4-(3-chloro-phenoxy)-phenyl]-1H-benzoimidazole-5-carboxylic acid amide |
| 14 | 2-[4-(5,6,7,8-tetrahydro-naphthalen-2-yloxy)-phenyl]-1H-benzoimidazole-5-carboxylic acid amide |
| 15 | 2-[4-(5-chloro-2-methyl-phenoxy)-phenyl]-1H-benzoimidazole-5-carboxylic acid amide |
| 16 | 2-[4-(3-trifluoromethyl-phenoxy)-phenyl]-1H-benzoimidazole-5-carboxylic acid amide |
| 17 | 2-[4-(4-methoxy-phenoxy)-phenyl]-1H-benzoimidazole-5-carboxylic acid amide |
| 18 | 2-[4-(4-methyl-phenoxy)-phenyl]-1H-benzoimidazole-5-carboxylic acid amide |
| 19 | 2-[4-(2-fluoro-3-trifluoromethyl-phenoxy)-phenyl]-1H-benzoimidazole-5-carboxylic acid amide |
| 20 | 2-[4-(2-chloro-4-methyl-phenoxy)-phenyl]-1H-benzoimidazole-5-carboxylic acid amide |
| 21 | 2-[4-(4-ethyl-phenoxy)-phenyl]-1H-benzoimidazole-5-carboxylic acid amide |
| 22 | 2-[4-(4-fluoro-phenoxy)-phenyl]-1H-benzoimidazole-5-carboxylic acid amide |
| 23 | 2-[4-(3,4-dimethoxy-phenoxy)-phenyl]-1H-benzoimidazole-5-carboxylic acid amide |
| 24 | 2-[4-(4-carbamoyl-phenoxy)-phenyl]-1H-benzoimidazole-5-carboxylic acid amide |
| 25 | 2-[4-(3-(N,N-dimethyl)amino-phenoxy)-phenyl]-1H-benzoimidazole-5-carboxylic acid amide |
| 26 | 2-[4-(4-nitro-phenoxy)-phenyl]-1H-benzoimidazole-5-carboxylic acid amide |
| 27 | 2-[4-(4-cyano-phenoxy)-phenyl]-1H-benzoimidazole-5-carboxylic acid amide |
| 28 | 3-{4-[4-(5-carbamoyl-1H-benzoimidazol-2-yl)-phenoxy]-phenyl}-propionic acid |
| 29 | 2-[4-(3-carboxy-phenoxy)-phenyl]-1H-benzoimidazole-5-carboxylic acid amide |
| 30 | 2-[4-(3-diethylcarbamoyl-phenoxy)-phenyl]-1H-benzoimidazole-5-carboxylic acid amide |
| 31 | 2-[4-(3-pyridyloxy)-phenyl]-1H-benzoimidazole-5-carboxylic acid amide |
| 32 | 2-[3-chloro-4-(3,4-dimethoxy-phenoxy)-phenyl]-1H-benzoimidazole-5-carboxylic acid amine |
| 33 | 2-[2-chloro-4-(4-chloro-phenoxy)-phenyl]-1H-benzoimidazole-5-carboxylic acid amide |
| 34 | 2-[3-chloro-4-(4-fluoro-methyl-phenoxy)-phenyl]-1H-benzoimidazole-5-carboxylic acid amide |
| 35 | 2-[3-chloro-4-(2-methoxy-4-methyl-phenoxy)-phenyl]-1H-benzoimidazole-5-carboxylic acid amide |
| 36 | 2-[3-chloro-4-(3-chloro-4-methyl-phenoxy)-phenyl]-1H-benzoimidazole-5-carboxylic acid amide |
| 37 | 2-(6-p-tolyloxy-pyridin-3-yl)-1H-benzoimidazole-5-carboxylic acid amide |
| 38 | 2-[4-(3-chloro-4-fluoro-phenylsulfanyl)-phenyl]-1H-benzoimidazole-5-carboxylic acid amide |
| 39 | 2-[4-(4-ethyl-phenylsulfanyl)-phenyl]-1H-benzoimidazole-5-carboxylic acid amide |
| 40 | 2-[4-(3,4-dimethoxy-phenylsulfanyl)-phenyl]-1H-benzoimidazole-5-carboxylic acid amide |
| 41 | 2-[4-(4-chloro-phenylsulfanyl)-phenyl]-1H-benzoimidazole-5-carboxylic acid amide |
| 42 | 2-[6-(4-chloro-phenylsulfanyl)-pyridin-3-yl]-1H-benzoimidazole-5-carboxylic acid amide |
| 43 | 2-[6-(4-methyl-phenylsulfanyl)-pyridin-3-yl]-1H-benzoimidazole-5-carboxylic acid amide |
| 44 | 2-[4-(4-trifluoromethoxy-phenylsulfanyl)-phenyl]-1H-benzoimidazole-5-carboxylic acid amide |
| 45 | 2-[4-(4-fluoro-phenyl)-phenyl]-1H-benzoimidazole-5-carboxylic acid amide |
| 46 | 2-[4-phenyl-phenyl]-1H-benzoimidazole-5-carboxylic acid amide |
| 47 | 2-[4-(2-chloro-phenyl)-phenyl]-1H-benzoimidazole-5-carboxylic acid amide |
| 48 | 2-[4-(4-chloro-phenyl)-phenyl]-1H-benzoimidazole-5-carboxylic acid amide |
| 49 | 2-[4-(2-pyridyl)-phenyl]-1H-benzoimidazole-5-carboxylic acid amide |
| 50 | 2-[4-(4-chloro-phenoxy)-phenyl]-1H-benzoimidazole-5-carboxylic acid |
| 51 | 2-[4-(4-methoxy-phenoxy)-phenyl]-1H-benzoimidazole-5-carboxylic acid |
| 52 | 2-[4-(4-fluoro-phenoxy)-phenyl]-1H-benzoimidazole-5-carboxylic acid |
| 53 | 2-[2-chloro-4-(4-chloro-phenoxy)-phenyl]-1H-benzoimidazole-5-carboxylic acid |
| 54 | 2-[4-(4-nitro-phenoxy)-phenyl]-1H-benzoimidazole-5-carboxylic acid |
| 55 | 2-[4-(4-chloro-phenyl)-phenyl]-1H-benzoimidazole-5-carboxylic acid |
| 56 | 2-[4-phenoxy-phenyl]-1H-benzoimidazole-5-carboxylic acid |
| 57 | 2-(4-phenoxy-phenyl)-1H-benzoimidazole-5-sulfonic acid amide |
| 58 | 2-[4-(3,4-dichloro-phenylsulfamoyl)-phenyl]-1H-benzoimidazole-5-carboxylic acid amide |
| 59 | 2-[4-(4-chloro-phenylsulfamoyl)-phenyl]-1H-benzoimidazole-5-carboxylic acid amide |
| 60 | 2-[4-(4-nitro-phenylsulfamoyl)-phenyl]-1H-benzoimidazole-5-carboxylic acid amide |
| 61 | 2-[4-(4-bromo-phenylsulfamoyl)-phenyl]-1H-benzoimidazole-5-carboxylic acid amide |
| 62 | 2-[4-(4-trifluoromethyl-phenylsulfamoyl)-phenyl]-1H-benzoimidazole-5-carboxylic acid amide |

-continued

| EX | Compound Name |
|---|---|
| 63 | 2-[4-(2-naphthylsulfamoyl)-phenyl]-1H-benzoimidazole-5-carboxylic acid amide |
| 64 | 2-[4-(4-methoxy-phenylsulfamoyl)-phenyl]-1H-benzoimidazole-5-carboxylic acid amide |
| 65 | 2-{4-[(4-chloro-phenyl)-methyl-sulfamoyl]-phenyl}-1H-benzoimidazole-5-carboxylic acid amide |
| 66 | 2-[4-(4-morpholino-4-yl-phenylsulfamoyl)-phenyl]-1H-benzoimidazole-5-carboxylic acid amide |
| 67 | 2-[4-(3,4-dichloro-benzenesulfonylamino)-phenyl]-1H-benzoimidazole-5-carboxylic acid amide |
| 68 | 6-chloro-2-[4-(3,4-dichloro-phenoxy)-phenyl]-1H-benzoimidazole-5-carboxylic acid amide |
| 69 | 2-[4-(4-methoxy-phenoxy)-phenyl]-1H-benzoimidazole-5-carboxylic acid methylamide |
| 70 | 2-[4-(4-chloro-phenoxy)-phenyl]-1H-benzoimidazole-5-carboxylic acid methylamide |
| 71 | 2-[4-(4-chloro-benzenesulfonyl)-phenyl]-1H-benzoimidazole-5-carboxylic acid amide |
| 72 | 2-[4-(4-chloro-benzenesulfinyl)-phenyl]-1H-benzoimidazole-5-carboxylic acid amide |
| 73 | 2-[4-(4-chloro-benzenesulfonyl)-phenyl]-1H-benzoimidazole-5-carboxylic acid |
| 74 | 2-[4-(4-chloro-benzenesulfinyl)-phenyl]-1H-benzoimidazole-5-carboxylic acid |
| 75 | 2-[4-(3,4-dichloro-phenoxy)-phenyl]-1H-imidazo[4,5-b]pyridine-5-carboxylic acid amide |
| 76 | 2-[4-(4-chloro-phenoxy)-phenyl]-1H-imidazo[4,5-b]pyridine-5-carboxylic acid amide |
| 77 | 2-{4-[4-(4-fluoro-phenyl)-piperazin-1-yl]-phenyl}-1H-benzoimidazole-5-carboxylic acid amide |
| 78 | 2-{4-[4-(pyridin-2-yl)-piperazin-1-yl]-phenyl}-1H-benzoimidazole-5-carboxylic acid amide |
| 79 | 2-{4-[4-(3-chloro-phenyl)-piperazin-1-yl]-phenyl}-1H-benzoimidazole-5-carboxylic acid amide |
| 80 | 2-[4-(4-phenyl-piperazin-1-yl)-phenyl]-1H-benzoimidazole-5-carboxylic acid amide |
| 81 | 2-{4-[4-(2,3-dichloro-phenyl)-piperazin-1-yl]-phenyl}-1H-benzoimidazole-5-carboxylic acid amide |
| 82 | 2-{4-[4-(4-methoxy-phenyl)-piperazin-1-yl]-phenyl}-1H-benzoimidazole-5-carboxylic acid amide |
| 83 | 2-{4-[4-(4-nitro-phenyl)-piperazin-1-yl]-phenyl}-1H-benzoimidazole-5-carboxylic acid amide |
| 84 | 2-[4-(benzo[1,3]dioxol-5-yloxy)-phenyl]-1H-benzoimidazole-5-carboxylic acid amide |
| 85 | 2-[4-(4-amino-phenoxy)-phenyl]-1H-benzoimidazole-5-carboxylic acid amide |
| 86 | 2-[4-(4-methanesulfonylamino-phenoxy)-phenyl]-1H-benzoimidazole-5-carboxylic acid amide |
| 87 | 2-[4-(4-hydroxy-phenylsulfanyl)-phenyl]-1H-benzoimidazole-5-carboxylic acid amide |
| 88 | 2-[4-(4-bromo-3-hydroxy-phenoxy)-phenyl]-1H-benzoimidazole-5-carboxylic acid amide |
| 89 | 2-[4-(4-chloro-2-hydroxy-phenoxy)-phenyl]-1H-benzoimidazole-5-carboxylic acid amide |
| 90 | 2-[4-(4-chloro-3-hydroxy-phenoxy)-phenyl]-1H-benzoimidazole-5-carboxylic acid amide |
| 91 | 2-[4-(3-chloro-4-fluoro-phenylsulfanyl)-phenyl]-1H-benzoimidazole-5-sulfonic acid amide |
| 92 | 2-[4-(naphthaten-2-yloxy)-phenyl]-1H-benzoimidazole-5-sulfonic acid amide |
| 93 | 2-[4-(4-chloro-3-trifluoromethyl-phenoxy)-phenyl]-1H-benzoimidazole-5-sulfonic acid amide |
| 94 | 2-[4-(4-chloro-phenoxy)-phenyl]-1H-benzoimidazole-5-sulfonic acid amide |
| 95 | 2-[4-(2,4-dichloro-phenylsulfamoyl)-phenyl]-1H-benzoimidazole-5-carboxylic acid amide |
| 96 | 2-[4-(3-chloro-phenoxy)-3-nitro-phenyl]-1H-benzoimidazole-5-carboxylic acid amide |
| 97 | 2-[4-(4-iodo-phenoxy)-phenyl]-1H-benzoimidazole-5-carboxylic acid amide |
| 98 | 2-(4-phenylcarbamoyl-phenyl)-1H-benzoimidazole-5-carboxylic acid amide |
| 99 | 2-[4-(4-chloro-phenylcarbamoyl)-phenyl]-1H-benzoimidazole-5-carboxylic acid amide |
| 100 | 2-{4-[(4-chloro-phenyl)-methyl-carbamoyl]-phenyl}-1H-benzoimidazole-5-carboxylic acid amide |
| 106A | 2-[4-(4-Methoxy-phenylsulfanyl)-phenyl]-1H-benzoimidazole-5-carboxylic acid amide |
| 106B | 2-[4-(3-Methoxy-phenylsulfanyl)-phenyl]-1H-benzoimidazole-5-carboxylic acid amide |
| 106C | 2-[4-(4-Bromo-3-methoxy-phenoxy)-phenyl]-1H-benzoimidazole-5-carboxylic acid amide |

Additional preferred compounds include: 2-[6-(4-chloro-phenoxy)-pyridazin-3-yl]-3H-benzoimidazole-5-carboxylic acid amide; 2-[4-(4-chloro-phenylamino)-phenyl]-3H-benzoimidazole-5-carboxylic acid amide; 2-[4-(4-chloro-3-dimethylamino-phenoxy)-phenyl]-3H-benzoimidazole-5-carboxylic acid amide; 2-[4-(4-chloro-3-methanesulfonylamino-phenoxy)-phenyl]-3H-benzoimidazole-5-carboxylic acid amide; 2-[4-(4-chloro-3-sulfamoyl-phenoxy)-phenyl]-3H-benzoimidazole-5-carboxylic acid amide; 2-[3-chloro-4-(4-chloro-phenylsulfamoyl)-phenyl]-3H-benzoimidazole-5-carboxylic acid amide; 2-[6-(4-chloro-phenylsulfamoyl)-pyridin-3-yl]-3H-benzoimidazole-5-carboxylic acid amide; 2-[6-(3,4-dichloro-phenylsulfamoyl)-pyridin-3-yl]-3H-benzoimidazole-5-carboxylic acid amide; 2-[6-(2,4-dichloro-phenylsulfamoyl)-pyridin-3-yl]-3H-benzoimidazole-5-carboxylic acid amide; and 2-[6-(4-chloro-benzenesulfonylamino)-pyridin-3-yl]-3H-benzoimidazole-5-carboxylic acid amide.

Related Compounds

The invention provides the disclosed compounds and closely related, pharmaceutically acceptable forms of the disclosed compounds, such as salts, esters, amides, acids, hydrates or solvated forms thereof; masked or protected forms; and racemic mixtures, or enantiomerically or optically pure forms. Related compounds also include compounds of the invention that have been modified to be detectable, e.g., isotopically labelled with $^{11}$C, or $^{18}$F for use as a probe in positron emission tomography (PET) or single-photon emission computed tomography (SPECT).

The invention also includes disclosed compounds having one or more functional groups (e.g., hydroxyl, amino, or carboxyl) masked by a protecting group. See, e.g., Greene and Wuts, *Protective Groups in Organic Synthesis*, 3$^{rd}$ ed., (1999) John Wiley & Sons, NY. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl) ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-d ioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyidiphenylmethyl, p-methoxyphenyldiphenylmethyl, di(p-methoxyphenyl) phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(Imidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate (levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Sulfonates

Examples of sulfonates include sulfate, methanesulfonate (mesylate), benzylsulfonate, and tosylate.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butyl phenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinyl benzyl, 9-anthrylmethyl and diphenylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Examples of Amides Include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Protection for the Carbonyl Group

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Protection for the Carboxyl Group

Esters

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthryl methyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

C. Synthetic Methods

The invention provides methods of making the disclosed compounds according to traditional organic synthetic methods as well as matrix or combinatorial synthetic methods. Schemes 1 through 12 describe suggested synthetic routes. Using these Schemes, the guidelines below, and the examples, a person of skill in the art may develop analogous or similar methods for a given compound that are within the invention.

One skilled in the art will recognize that synthesis of the compounds of the present invention may be effected by purchasing an intermediate or protected intermediate compounds described in any of the schemes disclosed herein. One skilled in the art will further recognize that during any of the processes for preparation of the compounds in the present invention, it may be necessary and/or desirable to protect sensitive or reactive groups on any of the molecules concerned. This may be achieved by means of conventional protecting groups, such as those described in "Protective Groups in Organic Synthesis", John Wiley & Sons, 1991. These protecting groups may be removed at a convenient stage using methods known from the art.

Examples of the described synthetic routes include Synthetic Examples 1 through 100. Compounds analogous to the target compounds of these examples can be, and in many cases, have been, made according to similar routes. The disclosed compounds are useful in basic research and as pharmaceutical agents as described in the next section.

Generally, a compound of structure (VII) was synthesized using the methods outlined in Schemes 1 and 2. An aryl or heteroaryl nucleophile of formula (I) in Scheme 1 was added to an aryl or heteroaryl fluoroaldehyde of formula (II) in the presence of a base, preferably $Cs_2CO_3$, to form compounds of general formula (III). These aldehydes can then be condensed with a 3,4-diamino-benzamide (VI), in the presence of an oxidizing agent such as $Na_2S_2O_5$ to provide benzimidazoles (VII). Additionally, compound (VI) can be obtained by condensation of the carboxylate (IV) with ammonia in the presence of an activating agent such as thionyl chloride. The resulting amide (V) can then be reduced using such reagents as $SnCl_2$, or $H_2$ and palladium to afford the diamine of formula (VI).

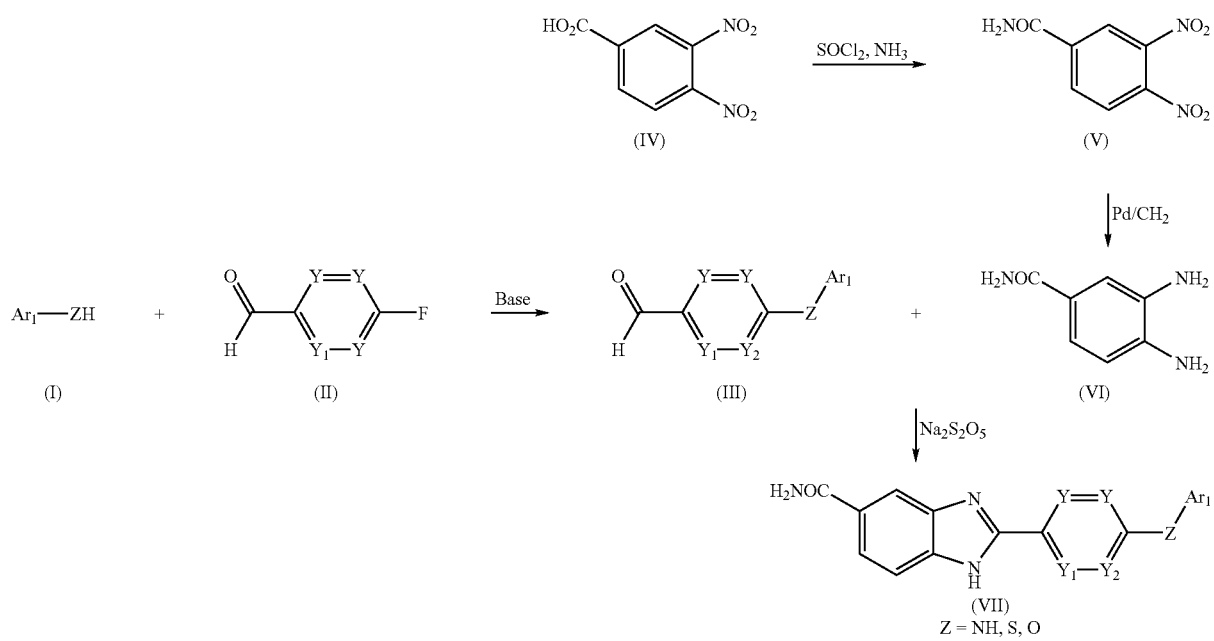

Alternatively compounds of formula (VII) can be obtained by the initial condensation of an aldehyde of formula (III) with 3,4-diamino-benzoic acid (VIII) (Scheme 2), in the presence of an oxidizing agent such as $Na_2S_2O_5$ to give a benzimidazole of formula (IX). The carboxylate of (IX) can then be converted to an amide by activation with 1,1'-carbonyldiimidazole (CDI), or other similar activating agent, followed by a nucleophilic amine to provide compounds of formula (VII).

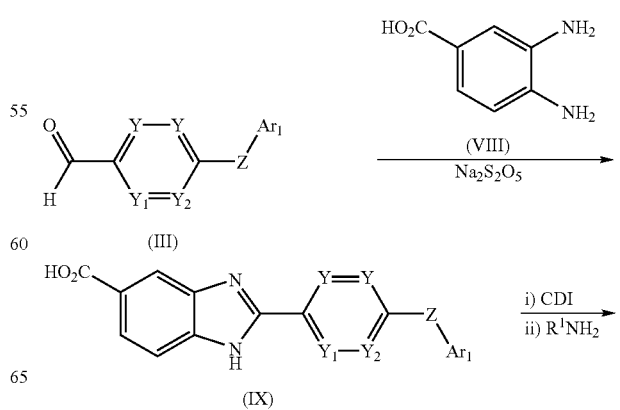

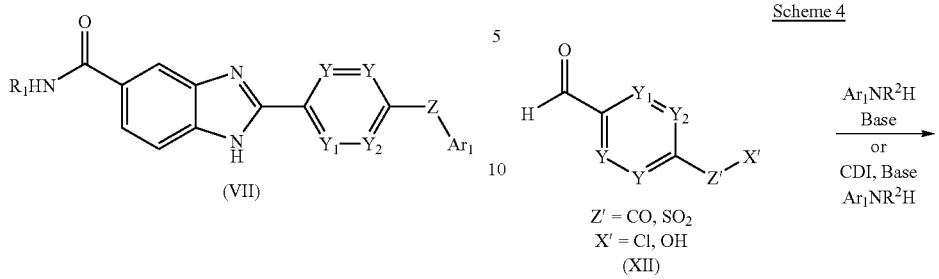

In addition compounds of formula (XI) (Scheme 3) can be obtained by the direct condensation of any commercial or synthesized aryl or heteroaryl aldehyde of formula (III) with a commercial or synthesized phenylenediamine or pyridinediamine of formula (X), in the presence of an oxidizing agent such as $Na_2S_2O_5$.

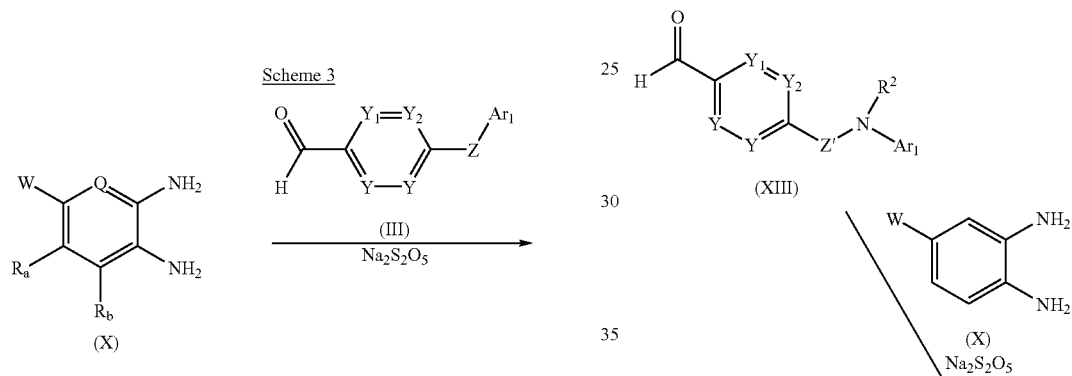

Compounds of general formula (XIV) can be synthesized by the methods outlined in Scheme 4. A sulfonyl chloride, or acid chloride of formula (XII) can be coupled with an aryl or heteroaryl amine, in the presence of base such as pyridine, to provide an aldehyde of formula (XIII). Alternatively a carboxylic acid of formula (XII) can be treated with an activating agent such as isobutyl chloroformate or 1,1'-carbonyldiimidazole and a base, followed by treatment with an aniline or heteroaryl amine to form amides of general formula (XIII). This compound can then be condensed with a phenylenediamine of formula (X) in the presence of an oxidizing agent such as $Na_2S_2O_5$ to provide benzimidazoles of formula (XIV).

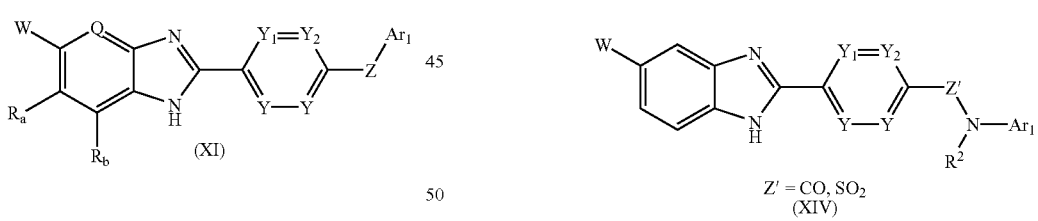

Compounds of the general formula (XIX) can be prepared according to the procedures outlined in Scheme 5. A substituted amino-benzoic acid of formula (XV) can be sequentially protected and nitrated by known methods to obtain compounds of formula (XVI). The carboxylate of (XVI) can then be converted to the amide through known coupling procedures, and subsequently deprotected to form compounds of formula (XVII). Reduction of the nitro group using reagents such as NaSH or $SnCl_2$ then provides the requisite phenylenediamine of formula (XVIII). Compound (XVIII) can then be condensed with compounds of formula (III), obtained by a method described above, in the presence of an oxidizing agent such as $Na_2S_2O_5$ to provide compounds of formula (XIX).

Scheme 5

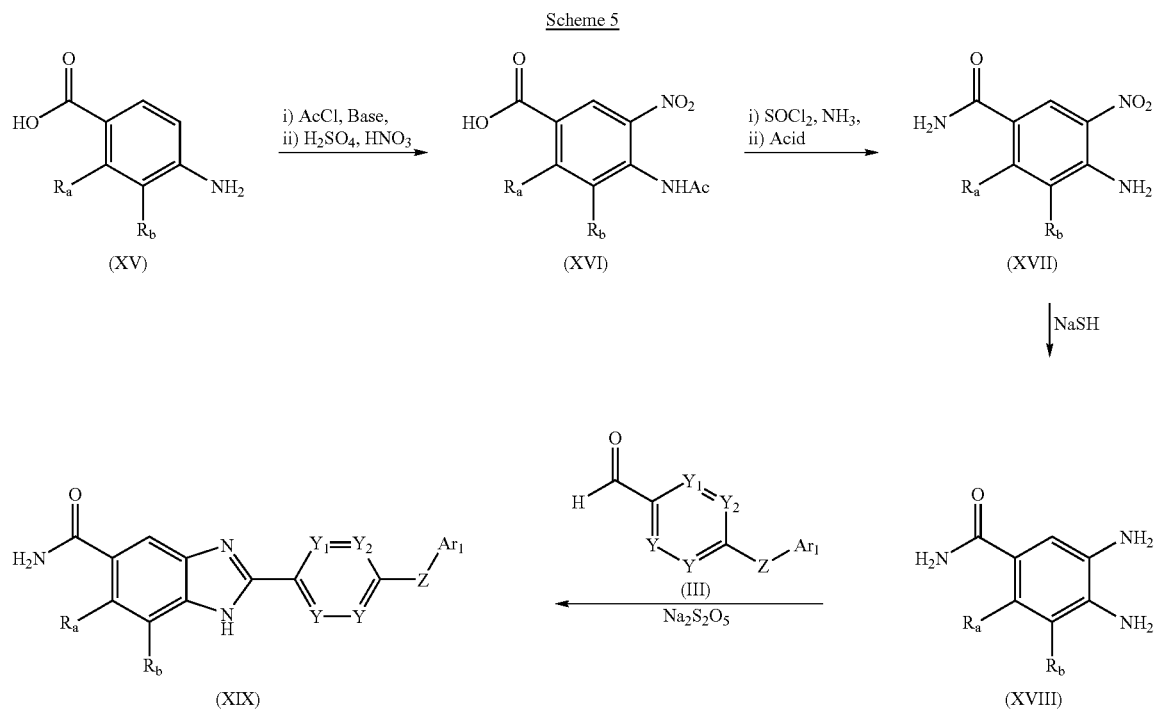

Compounds of general formula (XXI) and (XXIII) can be obtained using the general routes outlined in Scheme 6. Compounds of formula (VIIa), obtained using previously described methods, can be oxidized selectively to either sulfoxides of formula (XXII) or sulfones of formula (XX), using TeO$_2$ or oxone respectively. Additionally these carboxylates can be converted to amides by treatment with coupling agents such as 1,1'-carbonyldiimidazole, followed by an ammonia source such as (NH$_4$)$_2$CO$_3$ to afford compounds of formula (XXI) or (XXIII).

Scheme 6

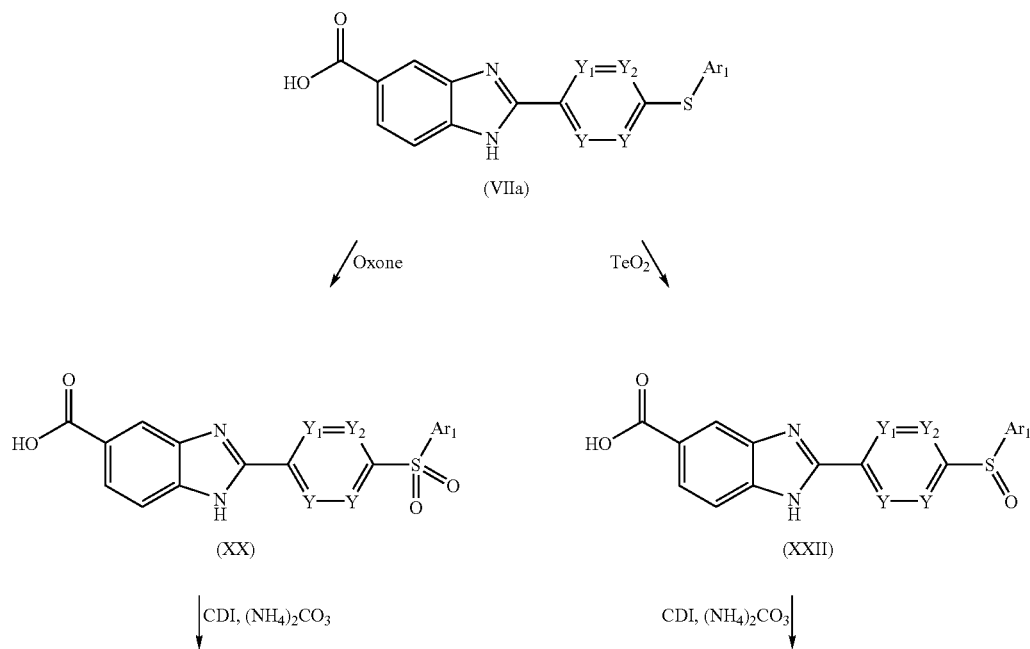

-continued

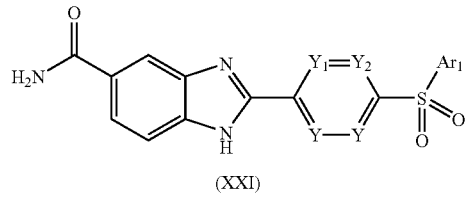

(XXI)

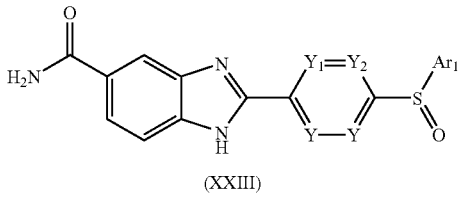

(XXIII)

Compounds of formula (XXX) can be obtained using the general procedures outlined in Scheme 7. Nitro-arylaldehydes or nitro-heteroarylaldehydes of formula (XXVII) can be reduced using SnCl₂ or other such reducing agent to amines of general formula (XXVIII). The resulting amines can then be treated with an aryl sulfonyl chloride in the presence of base to afford compounds of formula (XXIX). Condensation of (XXIX) with phenylenediamines of formula (X) in the presence of an oxidizing agent such as Na₂S₂O₅ provides benzimidazoles of general formula (XXX).

aldehyde of type (III) in the presence of an oxidizing agent such as Na₂S₂O₅ provides imidazopyridines of general formula (XXXV). The cyano group of (XXXV) can then be converted to an amide of formula (XXXVI) by hydrolysis with BF₃ in acetic acid.

Scheme 7

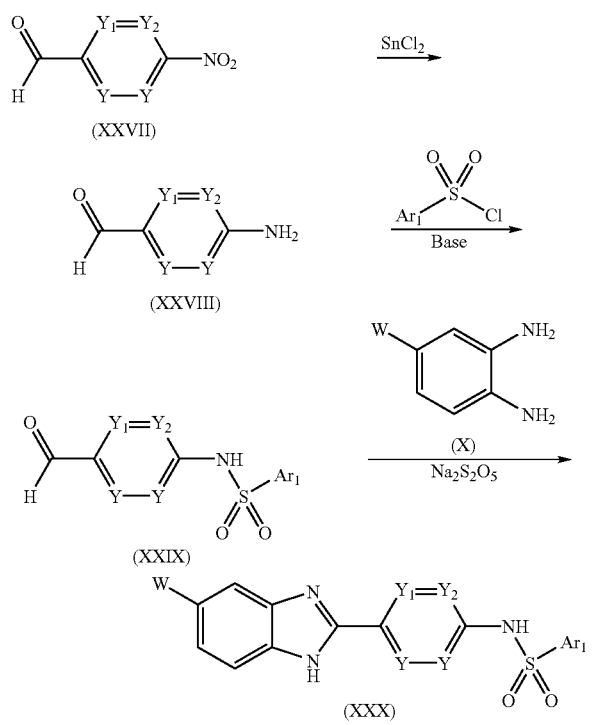

Scheme 8

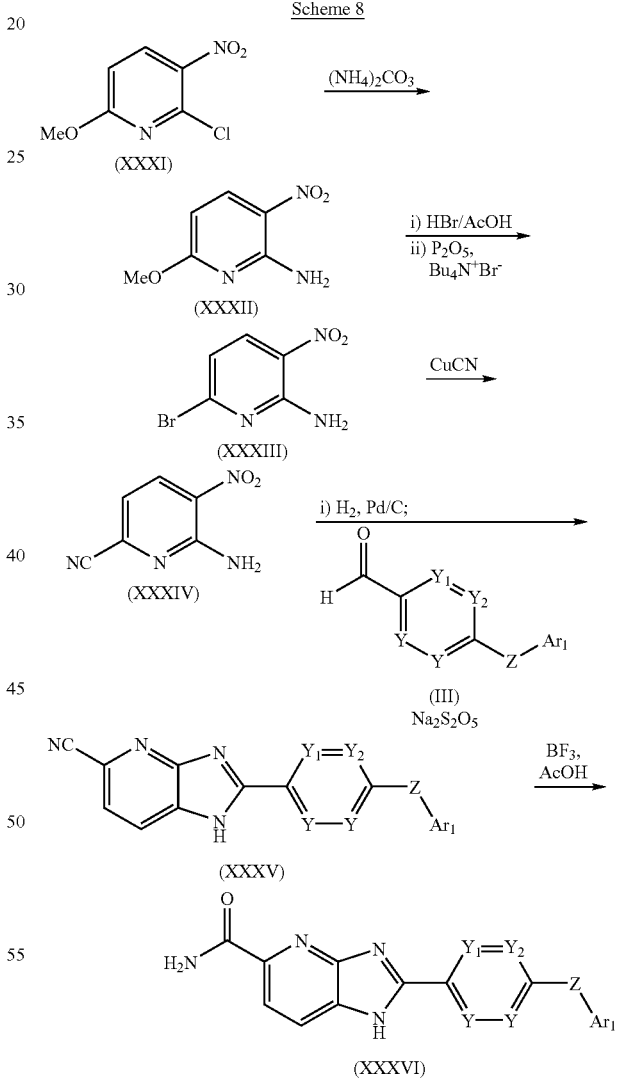

Compounds of general formula (XXXVI) can be synthesized using the methods outlined in Scheme 8. Treatment of pyridine (XXXI) with an ammonium equivalent such as (NH₄)₂CO₃ provides 2-aminopyridine (XXXII). Removal of the methyl group in (XXXII) with hydrobromic acid and acetic acid, followed by conversion to the bromide using a nucleophilic bromide source such as (C₄H₉)₄N⁺Br⁻, in the presence of P₂O₅, gives compound (XXXIII). Treatment of the bromide with a metallic cyanide such as CuCN then results in the formation of compound (XXXIV). Reduction of the nitro group of (XXXIV) using H₂ and Pd or other reducing agent, followed by condensation with an aryl Compounds of general formula (XXVI) were synthesized by the general methods described in Scheme 9. A fluoro-arylaldehyde or halo-heteroarylaldehyde of general formula (II) can be treated with a piperazine of formula (XXIV) in the presence of a base such as Cs₂CO₃ to afford compounds of general formula (XXV). Condensation of (XXV) with phenylenediamines of formula (X) in the presence of an oxidizing agent such as Na$_2$S$_2$O$_5$ provides benzimidazoles of general formula (XXVI).

a sulfonyl chloride (X=SO$_2$) or acid chloride (X=CO), under basic conditions to provide benzimidazoles of general formula (VIIf).

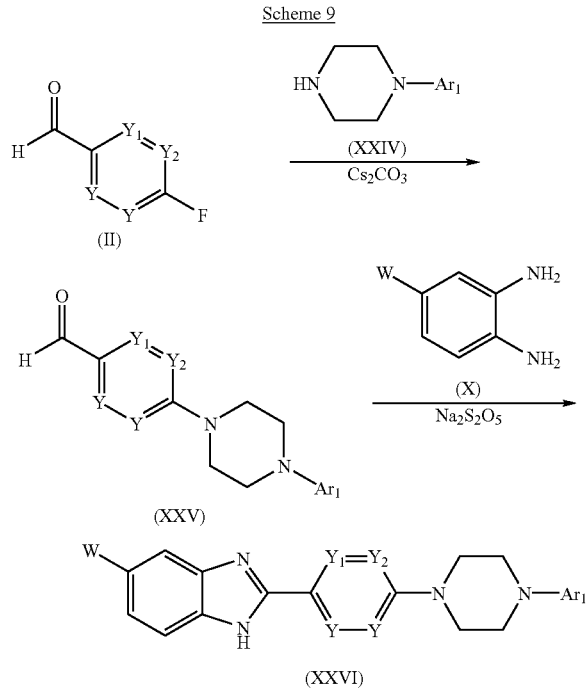

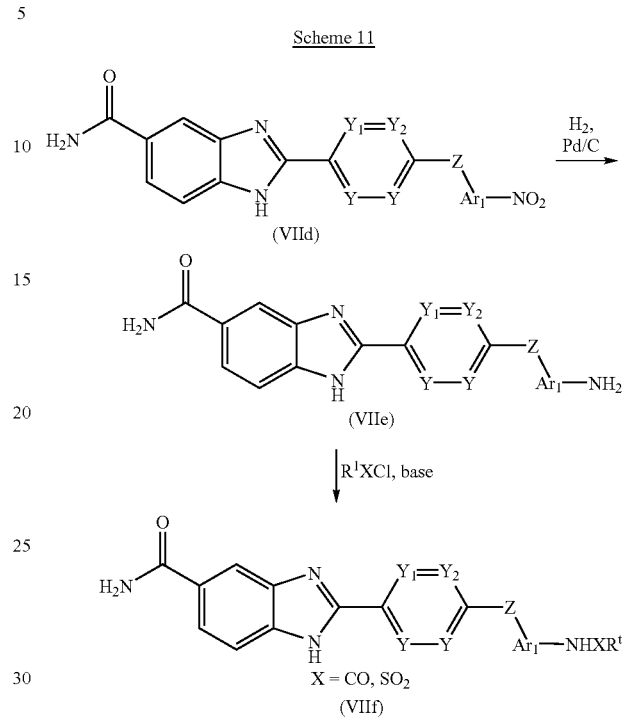

Compounds of general formula (VIIc) can be synthesized from compounds of formula (VIIb) by the methods described in Scheme 10. Compounds of general formula (VIIb), obtained from the methods described in Scheme 1, are treated with a coupling agent such as 1,1'-carbonyldiimidazole, or other similar coupling agent, and a nucleophilic amine to provide amides of formula (VIIc).

Compounds of general formula (VIIh) can be synthesized using the route outlined in Scheme 12. Compounds of formula (VIIg), obtained using previously described methods, can be treated with boron tribromide to remove the methyl group and provide benzimidazoles of general formula (VIIh).

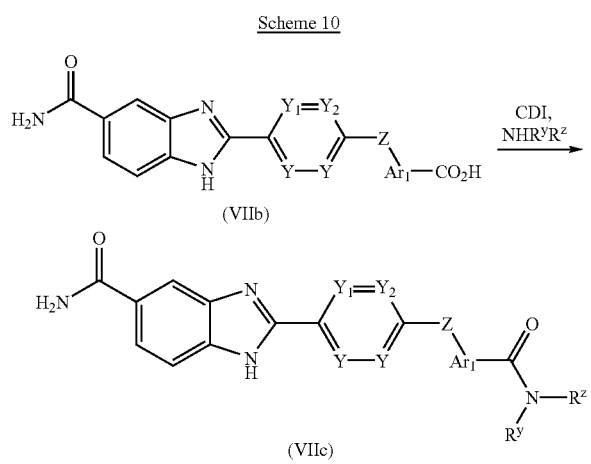

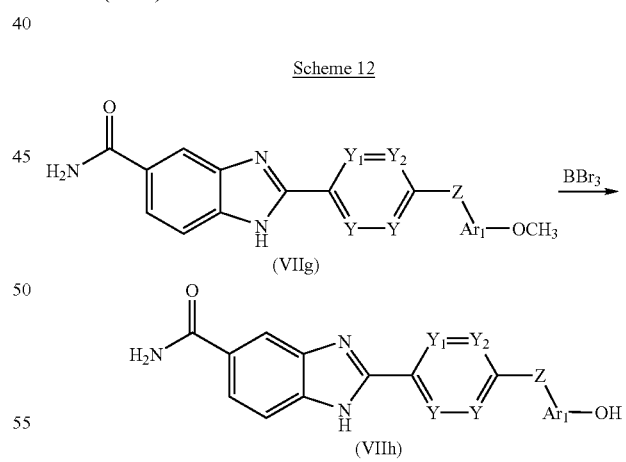

Compounds of general formula (VIIf) can be synthesized by the methods outlined in Scheme 11. Compounds of formula (VIId), obtained using previously described methods, can be reduced using H$_2$ and Pd or other reducing agent. The resulting amines of formula (VIIe) can be treated with

D. Formulation and Administration

The present compounds inhibit the checkpoint modulator Cds1 and therefore are useful as a medicine especially in methods for treating patients suffering from disorders or conditions that are modulated or regulated by Cds1, such as cancer.

The invention features a method for treating a subject with cancer, said method comprising administering to the subject a therapeutically effective amount of a pharmaceutical composition comprising a compound of the invention. The invention also provides a method for inhibiting Cds1 activity in a subject, wherein the method comprises administering to the subject a therapeutically effective amount of a pharmaceutical composition comprising a compound of the invention.

The compounds of the present invention may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier.

A carrier may take a wide variety of forms depending on the form of preparation desired for administration. These pharmaceutical compositions are desirably in unitary dosage form suitable, preferably, for oral administration, intravenous injection or parenteral injection. For example, in preparing the compositions in oral dosage form, any of the usual pharmaceutical media may be employed. These include water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. In view of their ease in administration, tablets and capsules represent the most advantageous oral dosage unit form, in which case solid pharmaceutical carriers are generally employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Such additives may facilitate the administration to the skin and/or may be helpful for preparing the desired compositions. These compositions may be administered in various ways, e.g., as a transdermal patch, as a spot-on, as an ointment. Acid addition salts of the compounds of formula I, due to their increased water solubility over the corresponding base form, are more suitable in the preparation of aqueous compositions.

It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Pharmaceutically acceptable acid addition salts include the therapeutically active non-toxic acid addition salt forms that the disclosed compounds are able to form. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term addition salt also comprises the solvates that the disclosed compounds, as well as the salts thereof, are able to form. Such solvates are for example hydrates, alcoholates and the like. Conversely the salt form can be converted by treatment with alkali into the free base form.

Stereoisomeric forms defines all the possible isomeric forms that the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention. For example, the present invention includes

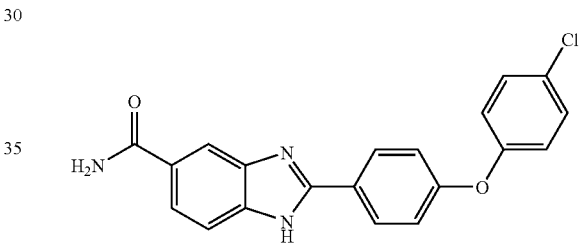

2-[4-(4-Chloro-phenoxy)-phenyl]-1H-benzoimidazole-5-carboxylic acid amide as well as

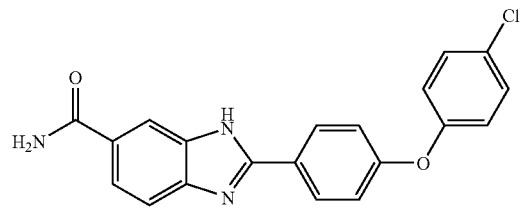

2-[4-(4-Chloro-phenoxy)-phenyl]-3H-benzoimidazole-5-carboxylic acid amide.

Those of skill in the treatment of disorders or conditions mediated by the Cds1 enzyme could easily determine the effective daily amount from the test results presented hereinafter and other information. In general it is contemplated that a therapeutically effective dose would be from 0.001 mg/kg to 100 mg/kg body weight, more preferably from 1 mg/kg to 50 mg/kg body weight. It may be appropriate to administer the therapeutically effective dose as two, three, four or more sub-doses at appropriate intervals throughout the day. Said sub-doses may be formulated as unit dosage forms, for example, containing 1 mg to 2000 mg, and in particular 10 to 500 mg of active ingredient per unit dosage form. Examples include 10 mg, 25 mg, 50 mg, 100 mg, 150 mg, 250 mg, and 500 mg dosage forms. Compounds of the invention may also be prepared in time-release or subcutaneous or transdermal patch formulations. Disclosed compound may also be formulated as a spray or other topical or inhalable formulations.

The exact dosage and frequency of administration depends on the particular compound of formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines.

The next section includes detailed information relating to the use of the disclosed compounds.

D. EXAMPLES

General Experimental:

All NMRs were obtained on a Bruker model EM 400, 400 MHz spectrometer. The format of the $^1$H NMR data below is: chemical shift in ppm down field of the tetramethylsilane reference (multiplicity, coupling constant J in Hz, integration).

HPLC retention times are reported in minutes, using the methods and conditions reported below.

| | |
|---|---|
| Instrument: | Agilent HP-1100 |
| Solvent: | Acetonitrile (0.05% TFA)/H$_2$O (0.05% TFA) |
| Flow rate: | 0.75 mL/min |
| Gradient: | 1 min at 1% H$_2$O; 7 min linear ramp to 99% H$_2$O; 4 min at 99% H$_2$O. |
| Column: | Zorbax Eclipse XDB-C8 (5 μm, 4.6 × 150 mm) |
| Temperature: | 35° C. |
| Wavelength: | Duel detection at 220 nM and 254 nM. |

All mass spectra were obtained on an Agilent series 1100 MSD using electrospray ionization in either positive or negative modes as indicated.

Example 1

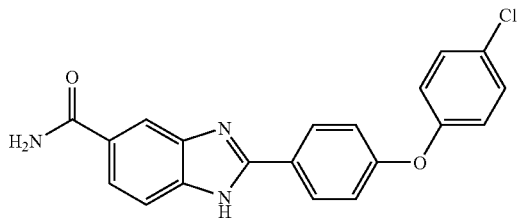

2-[4-(4-Chloro-phenoxy)-phenyl]-1H-benzoimidazole-5-carboxylic acid amide.

Scheme 2: To a solution of 5.0 g (13.7 mmol) of 2-[4-(4-chloro-phenoxy)-phenyl]-1H-benzoimidazole-5-carboxylic acid (Example 50), in N,N-dimethylformamide (100 mL) was added 1,1'-carbonyldiimidazole (5.1 g, 31.5 mmol). The mixture was stirred for 30 min at room temperature and then cooled to 0° C. Ammonium carbonate (6.0 g, 63 mmol) was added, and the reaction mixture was stirred for 18 h at room temperature. The solvent was evaporated under reduced pressure, and the residue was partitioned with ethyl acetate (30 mL) and water (3×10 mL). The ethyl acetate layer was collected and concentrated. The residue was purified by silica gel chromatography (5% methanol/CH$_2$Cl$_2$) yielding 4.2 g (85.7%) of the pure compound as a slightly yellow solid.

HPLC: R$_f$=7.3. MS (ESI+): mass calculated for C$_{20}$H$_{14}$ClN$_3$O$_2$, 363.08; m/z found, 364.1 [M+H]$^+$. $^1$H NMR (400 MHz, DMSO-d$_6$); 8.23 (d, J=9.0 Hz, 2H), 8.20 (d, J=0.78 Hz, 1H), 8.13 (br, s, 1H), 7.92 (dd, J=8.4, 1.6 Hz, 1H), 7.73 (d, J=8.4 Hz, 1H), 7.51 (d, J=8.8 Hz, 2H), 7.44 (br, s, 1H), 7.26 (d, J=8.8 Hz, 2H), 7.18 (d, J=9.0 Hz, 2H), 6.76 (br, s, 1H). $^{13}$C NMR (100 MHz, DMSO-d$_6$): 167.69, 159.75, 154.19, 151.40, 137.53, 135.53, 130.24, 130.16, 129.65, 128.54, 123.65, 121.59, 121.42, 118.54, 114.18, 113.85 ppm. Elemental analysis: calculated for C$_{20}$H$_{14}$ClN$_3$O$_2$: C, 66.03; H, 3.88; N, 11.55; found: C, 66.57; H, 3.87; N, 11.50.

Example 2

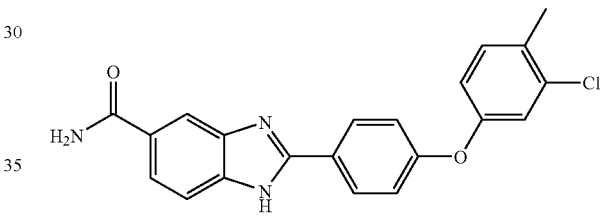

2-[4-(3-Chloro-4-methyl-phenoxy)-phenyl]-1H-benzoimidazole-5-carboxylic acid amide.

Scheme 1: To a solution of 4-fluorobenzaldehyde (0.3 mmol) in N,N-dimethylformamide (1.5 mL) was added 3-chloro-4-methylphenol (107 mg, 0.66 mmol), followed by Cs$_2$CO$_3$ (215 mg, 0.66 mmol). The mixture was heated at 90° C. for 24 h. The reaction mixture was then cooled to room temperature, and 311 mg of MP-carbonate scavenger resin (Argonaut, loading =2.64 mmol/g) was added. The mixture was shaken for 24 h, and the MP-carbonate resin was removed by filtration to provide crude 4-(3-chloro-4-methyl-phenoxy)-benzaldehyde. The crude filtrate was treated with 1.0 mL of a solution of 3,4-diamino-benzamide (0.33 mM) in N,N-dimethylformamide, followed by Na$_2$S$_2$O$_5$ (94 mg, 0.5 mmol). The mixture was heated to 95° C. for 24 h. The reaction mixture was then cooled to room temperature, and concentrated on a centrifugal evaporator. The residue was dissolved in 1.5 mL of N,N-dimethylformamide and purified by reverse phase HPLC (C$_{18}$, water/acetonitrile/0.1% TFA) to provide 55 mg (33% overall yield) of a white solid (TFA-salt).

HPLC: R$_f$=7.67. MS (ESI+): mass calculated for C$_{21}$H$_{16}$ClN$_3$O$_2$, 377.09; m/z found 378.09 [M+H]$^+$. $^1$H NMR (400 MHz, DMSO-d$_6$): 8.07 (d, J=8.9 Hz, 2H), 8.03 (d, J=1.0 Hz, 1H), 7.93 (br s, 1H), 7.72 (dd, J=8.5 Hz, J=1.5 Hz, 1H), 7.54 (d, J=8.5 Hz, 1H), 7.29 (d, J=8.8 Hz, 1H), 7.24 (br s, 1H), 7.10 (s, 1H), 7.08 (d, J=8.9 Hz, 2H), 6.91 (dd, J=8.3 Hz, J=2.6 Hz, 1H), 2.19 (s, 3H).

Example 3

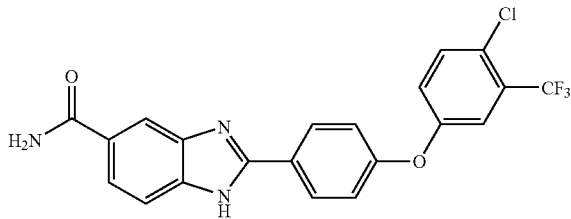

2-[4-(4-Chloro-3-trifluoromethyl-phenoxy)-phenyl]-1H-benzoimidazole-5-carboxylic acid amide.

This compound was prepared according to the methods described in Example 2 and Scheme 1, substituting 4-chloro-3-trifluoromethylphenol for 3-chloro-4-methylphenol.

HPLC: $R_t$=7.45. MS (ESI+): mass calc. for $C_{21}H_{13}ClF_3N_3O_2$, 431.06; m/z found, 432.0 [M+H]$^+$. $^1$H NMR (400 MHz, CD$_3$OD): 8.15 (br s, 1H), 8.13 (d, J=8.8, 2H), 7.80 (d, J=7.6, 1H), 7.61 (br s, 1H), 7.60 (d, J=8.8, 2H), 7.44 (d, J=2.8, 1H), 7.29-7.26 (dd, J=8.8, 2.7, 1H), 7.20 (d, J=8.8, 2H).

Example 4

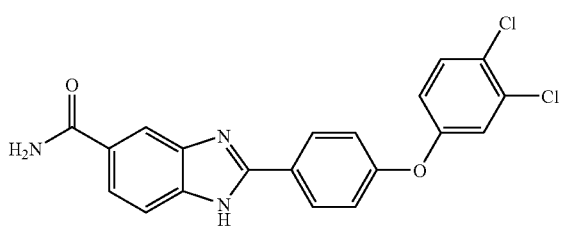

2-[4-(3,4-Dichloro-phenoxy)-phenyl]-1H-benzoimidazole-5-carboxylic acid amide.

This compound was prepared according to the methods described in Example 2 and Scheme 1, substituting 3,4-dichlorophenol for 3-chloro-4-methylphenol.

HPLC: $R_t$=7.64. MS (ESI+): mass calculated for $C_{20}H_{13}Cl_2N_3O_2$, 397.04; m/z found 398.0 [M+H]$^+$. $^1$H NMR (400 MHz, DMSO-d$_6$): 8.05 (d, J=8.6 Hz, 2H), 7.99 (s, 1H), 7.88 (br s, 1H), 7.68 (d, J=8.5 Hz, 1H), 7.51 (t, J=8.9 Hz, 2H), 7.30 (d, J=2.8 Hz, 1H), 7.19 (br s, 1H), 7.12 (d, J=8.6 Hz, 2H), 6.97 (dd, J=8.8 Hz, J=2.8 Hz, 1H).

Example 5

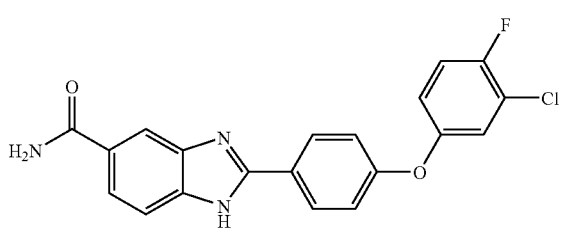

2-[4-(3-Chloro-4-fluoro-phenoxy)-phenyl]-1H-benzoimidazole-5-carboxylic acid amide.

This compound was prepared according to the methods described in Example 2 and Scheme 1, substituting 3-chloro-4-fluorophenol for 3-chloro-4-methylphenol.

HPLC: $R_t$=7.39. MS (ESI+): mass calculated for $C_{20}H_{13}ClFN_3O_2$, 381.07; m/z found 382.07 [M+H]$^+$. $^1$H NMR (400 MHz, DMSO-d$_6$): 8.13 (d, J=8.9 Hz, 2H), 8.08 (d, J=1.0 Hz, 1H), 7.98 (br s, 1H), 7.78 (dd, J=8.5 Hz, J=1.5 Hz, 1H), 7.59 (d, J=8.5 Hz, 1H), 7.44 (d, J=9.0 Hz, 1H), 7.39 (m, 1H), 7.29 (br s, 1H), 7.17 (d, J=8.9 Hz, 2H), 7.11 (m, 1H).

Example 6

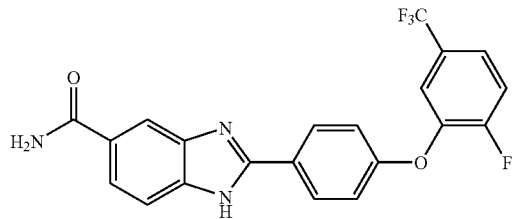

2-[4-(2-Fluoro-5-trifluoromethyl-phenoxy)-phenyl]-1H-benzoimidazole-5-carboxylic acid amide.

This compound was prepared according to the methods described in Example 2 and Scheme 1, substituting 2-fluoro-5-trifluoromethylphenol for 3-chloro-4-methylphenol.

HPLC: $R_t$=7.57. MS (ESI+): mass calculated for $C_{21}H_{13}F_4N_3O_2$, 415.09; m/z found 416.11 [M+H]$^+$. $^1$H NMR (400 MHz, DMSO-d$_6$): 8.22 (d, J=8.9 Hz, 2H), 8.16 (s, 1H), 8.06 (br s, 1H), 7.85 (dd, J=8.5 Hz, J=1.4 Hz, 1H), 7.77-7.71 (m, 3H), 7.67 (d, J=8.5 Hz, 1H), 7.37 (br s, 1H), 7.28 (d, J=8.8 Hz, 2H).

Example 7

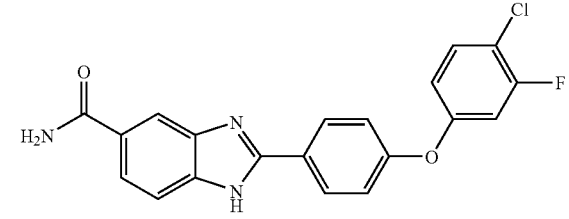

2-[4-(4-Chloro-3-fluoro-phenoxy)-phenyl]-1H-benzoimidazole-5-carboxylic acid amide.

This compound was prepared according to the methods described in Example 2 and Scheme 1, substituting 4-chloro-3-fluorophenol for 3-chloro-4-methylphenol.

HPLC: $R_t$=7.50. MS (ESI+): mass calculated for $C_{20}H_{13}ClFN_3O_2$, 381.07; m/z found 382.07 [M+H]$^+$. $^1$H NMR (400 MHz, DMSO-d$_6$): 8.23 (d, J=8.9 Hz, 2H), 8.17 (s, 1H), 8.07 (br s, 1H), 7.85 (dd, J=8.5 Hz, J=1.5 Hz, 1H), 7.67 (dd, J=8.3 Hz, J=1.5 Hz, 1H), 7.65 (d, J=8.8 Hz, 1H), 7.38 (br s, 1H), 7.33 (m, 1H), 7.30 (d, J=8.8 Hz, 2H), 7.01 (m, 1H).

Example 8

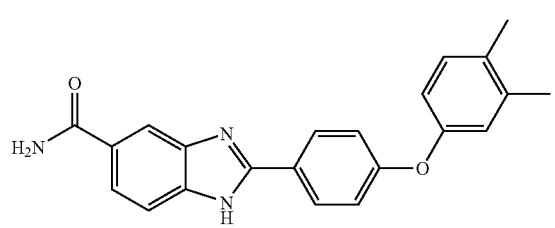

2-[4-(3,4-Dimethyl-phenoxy)-phenyl]-1H-benzoimidazole-5-carboxylic acid amide.

This compound was prepared according to the methods described in Example 2 and Scheme 1, substituting 3,4-dimethylphenol for 3-chloro-4-methylphenol.

HPLC: $R_t$=7.10. MS (ESI+): mass calculated for $C_{22}H_{19}N_3O_2$, 357.15; m/z found 358.1 [M+H]$^+$. $^1$H NMR (400 MHz, DMSO-d$_6$): 8.08 (d, J=8.9 Hz, 2H), 8.04 (s, 1H), 7.91 (br s, 1H), 7.70 (dd, J=8.4 Hz, J=1.5 Hz, 1H), 7.52 (d, J=8.5 Hz, 1H), 7.21 (br s, 1H), 7.12 (d, J=8.3 Hz, 1H), 7.03 (d, J=8.8 Hz, 2H), 6.86 d, J=2.5 Hz, 1H), 6.77 (dd, J=8.1 Hz, J=2.6 Hz, 1H), 2.14 (s, 6H).

Example 9

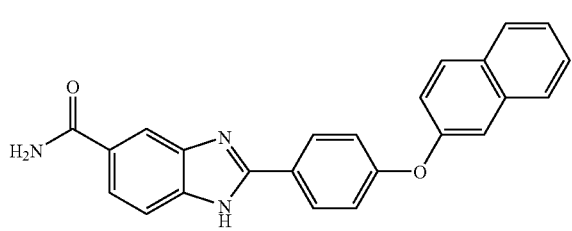

2-[4-(2-Naphthyloxy)-phenyl]-1H-benzoimidazole-5-carboxylic acid amide.

This compound was prepared according to the methods described in Example 1 and Scheme 2, substituting 2-naphthol for 4-chlorophenol.

HPLC: $R_t$=7.48. MS (ESI+): mass calculated for $C_{24}H_{17}N_3O_2$, 379.13; m/z found 380.1 [M+H]$^+$. $^1$H NMR (400 MHz, DMSO-d$_6$): 8.38 (d, J=8.7 Hz, 2H), 8.32 (s, 1H), 8.22 (br s, 1H), 8.19 (d, J=9.1 Hz, 1H), 8.12 (d, J=7.7 Hz, 1H), 8.03 (m, 2H), 7.83 (d, J=8.6 Hz, 1H), 7.75 (s, 1H), 7.67 (m, 2H), 7.53 (dd, J=8.8 Hz, J=2.4 Hz, 2H), 7.44 (d, J=8.7 Hz, 2H).

Example 10

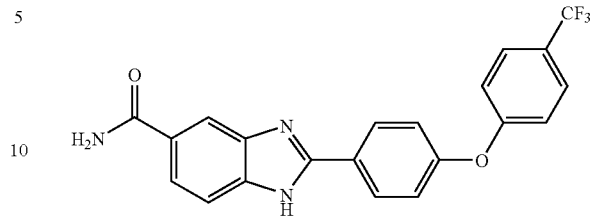

2-[4-(4-Trifluoromethyl-phenoxy)-phenyl]-1H-benzoimidazole-5-carboxylic acid amide.

This compound was prepared according to the methods described in Example 1 and Scheme 2, substituting 4-trifluoromethylphenol for 4-chlorophenol.

HPLC: $R_t$=7.60. MS (ESI+): mass calculated for $C_{21}H_{14}F_3N_3O_2$, 397.10; m/z found 398.1 [M+H]$^+$. $^1$H NMR (400 MHz, DMSO-d$_6$): 8.46 (d, J=8.9 Hz, 2H), 8.37 (d, J=1.0 Hz, 1H), 8.26 (br s, 1H), 8.06 (dd, J=8.5 Hz, J=1.5 Hz, 1H), 8.00 (d, J=8.5 Hz, 2H), 7.88 (d, J=8.5 Hz, 1H), 7.56 (br s, 1H), 7.55 (d, J=8.9 Hz, 2H), 7.49 (d, J=8.4 Hz, 2H).

Example 11

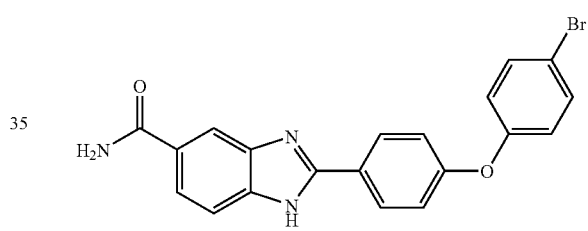

2-[4-(4-Bromo-phenoxy)-phenyl]-1H-benzoimidazole-5-carboxylic acid amide.

This compound was prepared according to the methods described in Example 1 and Scheme 2, substituting 4-bromophenol for 4-chlorophenol.

HPLC: $R_t$=7.44. MS (ESI+): mass calculated for $C_{20}H_{14}BrN_3O_2$, 407.03; m/z found 408.0 [M+H]$^+$. $^1$H NMR (400 MHz, DMSO-d$_6$): 8.17 (d, J=8.7 Hz, 2H), 8.11 (s, 1H), 8.01 (br s, 1H), 7.80 (d, J=8.5 Hz, 1H), 7.62 (d, J=8.5 Hz, 1H), 7.58 (d, J=8.9 Hz, 2H), 7.32 (br s, 1H), 7.20 (d, J=8.7 Hz, 2H), 7.07 (d, J=8.9 Hz, 2H).

Example 12

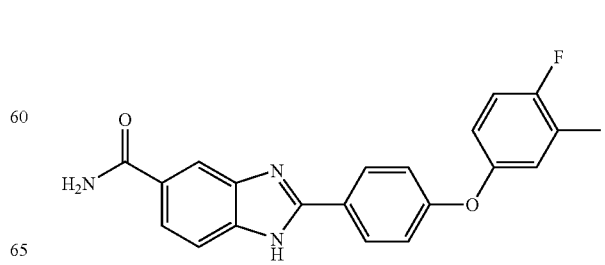

2-[4-(4-Fluoro-3-methyl-phenoxy)-phenyl]-1H-benzoimidazole-5-carboxylic acid amide.

This compound was prepared according to the methods described in Example 2 and Scheme 1, substituting 4-fluoro-3-methylphenol for 3-chloro-4-methylphenol.

HPLC: $R_t$=7.42. MS (ESI+): mass calculated for $C_{21}H_{16}FN_3O_2$, 361.12; m/z found 362.12 [M+H]$^+$. $^1$H NMR (400 MHz, DMSO-d$_6$): 8.19 (d, J=8.9 Hz, 2H), 8.16 (s, 1H), 8.07 (br s, 1H), 7.86 (dd, J=8.4 Hz, J=1.2 Hz, 1H), 7.67 (d, J=8.5 Hz, 1H), 7.38 (br s, 1H), 7.23 (t, J=9.1 Hz, 1H), 7.18 (d, J=8.9 Hz, 2H), 7.12 (m, 1H), 7.01 (m, 1H), 2.25 (s, 3H).

Example 13

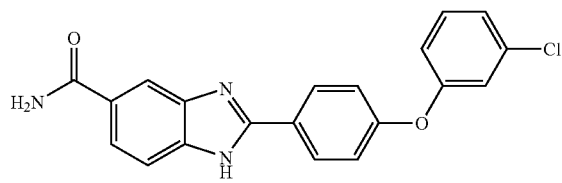

2-[4-(3-Chloro-phenoxy)-phenyl]-1H-benzoimidazole-5-carboxylic acid amide.

This compound was prepared according to the methods described in Example 1 and Scheme 2, substituting 3-chlorophenol for 4-chlorophenol.

HPLC: $R_t$=7.30. MS (ESI+): mass calculated for $C_{20}H_{14}ClN_3O_2$, 363.08; m/z found 364.0 [M+H]$^+$. $^1$H NMR (400 MHz, DMSO-d$_6$): 8.24 (d, J=8.6 Hz, 2H), 8.19 (s, 1H), 8.09 (br s, 1H), 7.88 (d, J=8.5 Hz, 1H), 7.70 (d, J=8.4 Hz, 1H), 7.49 (t, J=8.2 Hz, 1H), 7.40 (br s, 1H), 7.32 (s, 1H), 7.29 (d, J=8.6 Hz, 2H), 7.25 (m, 1H), 7.12 (m, 1H).

Example 14

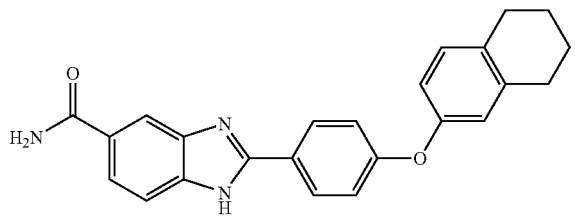

2-[4-(5,6,7,8-Tetrahydro-naphthalen-2-yloxy)-phenyl]-1H-benzoimidazole-5-carboxylic acid amide.

This compound was prepared according to the methods described in Example 1 and Scheme 2, substituting 5,6,7,8-tetrahydro-naphthalen-2-ol for 4-chlorophenol.

HPLC: $R_t$=7.89. MS (ESI+): mass calculated for $C_{24}H_{21}N_3O_2$, 383.16; m/z found 384.14 [M+H]$^+$. $^1$H NMR (400 MHz, DMSO-d$_6$): 8.18 (m, 3H), 8.07 (br s, 1H), 7.87 (d, J=8.5 Hz, 1H), 7.68 (d, J=8.5 Hz, 1H), 7.38 (br s, 1H), 7.17 (d, J=8.7 Hz, 2H), 7.14 (d, J=8.3 Hz, 1H), 6.86 (m, 2H), 2.73 (m, 4H), 1.74 (m, 4H).

Example 15

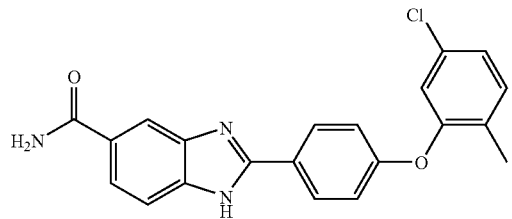

2-[4-(5-Chloro-2-methyl-phenoxy)-phenyl]-1H-benzoimidazole-5-carboxylic acid amide.

This compound was prepared according to the methods described in Example 2 and Scheme 1, substituting 5-chloro-2-methylphenol for 3-chloro-4-methylphenol.

HPLC: $R_t$=7.59. MS (ESI+): mass calculated for $C_{21}H_{16}ClN_3O_2$, 377.09; m/z found 378.09 [M+H]$^+$. $^1$H NMR (400 MHz, DMSO-d$_6$): 8.20 (d, J=8.9 Hz, 2H), 8.15 (s, 1H), 8.05 (br s, 1H), 7.84 (dd, J=8.5 Hz, J=1.3 Hz, 1H), 7.65 (d, J=8.5 Hz, 1H), 7.41 (d, J=8.0 Hz, 1H), 7.36 (br s, 1H), 7.26 (dd, J=8.2 Hz, J=2.1 Hz, 1H), 7.15 (d, J=8.9 Hz, 2H), 7.13 (d, J=2.1 Hz, 1H), 2.16 (s, 3H).

Example 16

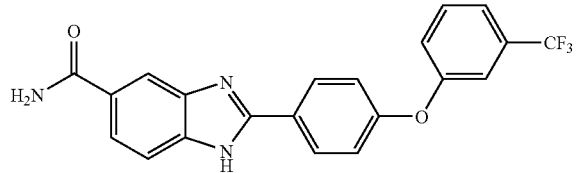

2-[4-(3-Trifluoromethyl-phenoxy)-phenyl]-1H-benzoimidazole-5-carboxylic acid amide.

This compound was prepared according to the methods described in Example 1 and Scheme 2, substituting 3-trifluoromethylphenol for 4-chlorophenol.

HPLC: $R_t$=7.16. MS (ESI+): mass calculated for $C_{21}H_{14}F_3N_3O_2$, 397.10; m/z found 398.10 [M+H]$^+$. $^1$H NMR (400 MHz, DMSO-d$_6$): 8.30 (br d, J=8.2 Hz, 3H), 8.10 (br s, 1H), 7.82 (br m, 1H), 7.74 (t, J=7.78 Hz, 1H), 7.62 (br d, J=7.8 Hz, 1H), 7.49 (br m, 3H), 7.32 (d, J=8.9 Hz, 2H).

Example 17

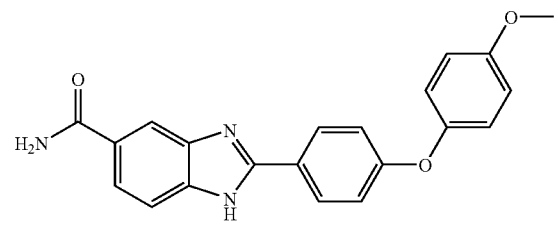

2-[4-(4-Methoxy-phenoxy)-phenyl]-1H-benzoimidazole-5-carboxylic acid amide.

This compound was prepared according to the methods described in Example 2 and Scheme 1, substituting 4-methoxyphenol for 3-chloro-4-methylphenol.

HPLC: $R_t$=6.95. MS (ESI+): mass calculated for $C_{21}H_{17}N_3O_3$, 359.13; m/z found, 360.1 [M+H]$^+$. $^1$H NMR (400 MHz, DMSO-d$_6$): 8.35-8.33 (m, 3H), 8.26 (br, s, 1H), 8.06 (d, J=8.5 Hz, 1H), 7.87 (d, J=8.4 Hz, 1H), 7.32-7.27 (m, 4H), 7.22-7.19 (m, 2H), 3.95 (s, 3H).

Example 18

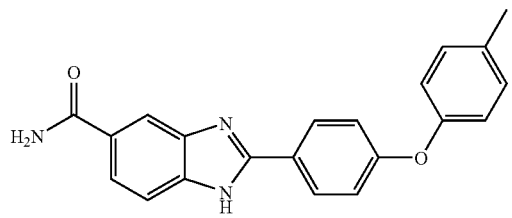

2-[4-(4-Methyl-phenoxy)-phenyl]-1H-benzoimidazole-5-carboxylic acid amide.

This compound was prepared according to the methods described in Example 1 and Scheme 2, substituting 4-methylphenol for 4-chlorophenol.

HPLC: $R_t$=7.27. MS (ESI+): mass calculated for $C_{21}H_{17}N_3O_2$, 343.13; m/z found 344.1 [M+H]$^+$. $^1$H NMR (400 MHz, DMSO-d$_6$): 8.20 (d, J=9.0 Hz, 2H), 8.11 (br s, 1H), 7.89 (dd, J=8.5 Hz, J=1.5 Hz, 1H), 7.70 (d, J=8.5 Hz, 1H), 7.42 (br s, 1H), 7.28 (d, J=8.6 Hz, 2H), 7.19 (d, J=8.9 Hz, 2H), 7.06 (d, J=8.5 Hz, 2H), 2.34 (s, 3H).

Example 19

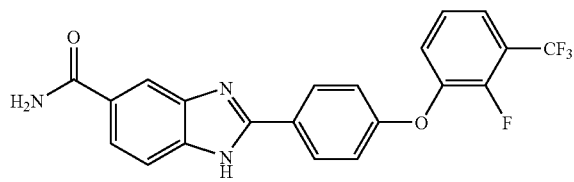

2-[4-(2-Fluoro-3-trifluoromethyl-phenoxy)-phenyl]-1H-benzoimidazole-5-carboxylic acid amide.

This compound was prepared according to the methods described in Example 2 and Scheme 1, substituting 2-fluoro-3-trifluoromethylphenol for 3-chloro-4-methylphenol.

HPLC: $R_t$=7.58. MS (ESI+): mass calculated for $C_{21}H_{13}F_4N_3O_2$, 415.09; m/z found 416.08 [M+H]$^+$. $^1$H NMR (400 MHz, DMSO-d$_6$): 8.23 (d, J=8.8 Hz, 2H), 8.17 (s, 1H), 8.06 (br s, 1H), 7.85 (dd, J=8.4 Hz, J=1.1 Hz, 1H), 7.67 (m, 3H), 7.49 (t, J=8.2 Hz, 1H), 7.37 (br s, 1H), 7.31 (d, J=8.8 Hz, 2H).

Example 20

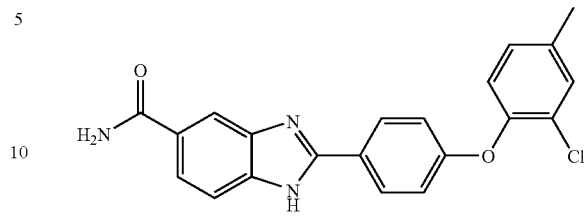

2-[4-(2-Chloro-4-methyl-phenoxy)-phenyl]-1H-benzoimidazole-5-carboxylic acid amide.

This compound was prepared according to the methods described in Example 2 and Scheme 1, substituting 2-chloro-4-methylphenol for 3-chloro-4-methylphenol.

HPLC: $R_t$=7.53. MS (ESI+): mass calculated for $C_{21}H_{16}ClN_3O_2$, 377.09; m/z found 378.09 [M+H]$^+$. $^1$H NMR (400 MHz, DMSO-d$_6$): 8.10 (d, J=8.9 Hz, 2H), 8.07 (d, J=0.9 Hz, 1H), 7.98 (br s, 1H), 7.76 (dd, J=8.5 Hz, J=1.5 Hz, 1H), 7.57 (d, J=8.5 Hz, 1H), 7.40 (d, J=1.6 Hz, 1H), 7.29 (br s, 1H), 7.15 (m, 2H), 7.02 (d, J=8.9 Hz, 2H), 2.26 (s, 3H).

Example 21

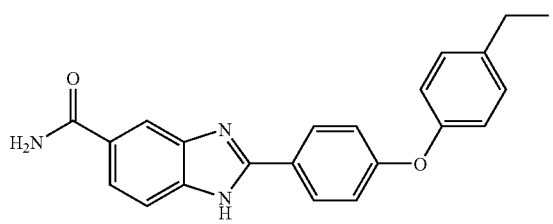

2-[4-(4-Ethyl-phenoxy)-phenyl]-1H-benzoimidazole-5-carboxylic acid amide.

This compound was prepared according to the methods described in Example 2 and Scheme 1, substituting 4-ethylphenol for 3-chloro-4-methylphenol.

HPLC: $R_t$=7.54. MS (ESI+): mass calculated for $C_{22}H_{19}N_3O_2$, 357.15; m/z found 358.1 [M+H]$^+$. $^1$H NMR (400 MHz, DMSO-d$_6$): 8.26 (d, J=8.6 Hz, 2H), 8.24 (s, 1H), 8.14 (br s, 1H), 7.94 (d, J=8.3 Hz, 1H), 7.75 (d, J=8.4 Hz, 1H), 7.45 (br s, 1H), 7.38 (d, J=8.3 Hz, 2H), 7.25 (d, J=8.6 Hz, 2H), 7.14 (d, J=8.3 Hz, 2H), 2.71 (q, J=7.2 Hz, 2H), 1.28 (t, J=7.6 Hz, 3H).

Example 22

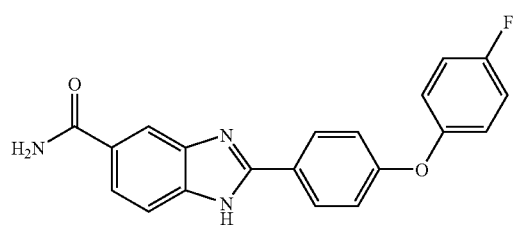

2-[4-(4-Fluoro-phenoxy)-phenyl]-1H-benzoimidazole-5-carboxylic acid amide.

Scheme 3: To a solution of 4-(4-fluoro-phenoxy)-benzaldehyde (136 mg, 0.67 mmol) in N,N-dimethylacetamide (2 mL) was added 100 mg (0.67 mmol) of 3,4-diaminobenzamide (100 mg, 0.67 mmol) followed by $Na_2S_2O_5$ (165 mg, 0.87 mmol). The reaction mixture was heated at 100° C. for 18 h, at which time it was allowed to cool to room temperature. The solution was filtered, and the filtrate was concentrated on a centrifugal evaporator. The residue was dissolved in 1.5 mL of N,N-dimethylformamide and was purified by reverse phase HPLC (Cl 8, acetonitrile/water/ 0.1% TFA) giving 136 mg (56%) of a white solid (isolated as TFA salt).

HPLC: $R_t$=7.02. MS (ESI+): mass calculated for $C_{20}H_{14}FN_3O_2$, 347.11; m/z found, 348.1 [M+H]$^+$. $^1$H NMR (400 MHz, DMSO-$d_6$): 8.16-8.13 (m, 4H), 8.05 (br, s, 1H), 7.84 (dd, J=8.5, 1.2 Hz, 1H), 7.64 (d, J=8.5 Hz, 1H), 7.36 (br, s, 1H), 7.27-7.23 (m, 2H), 7.18-7.14 (m, 5H).

Example 23

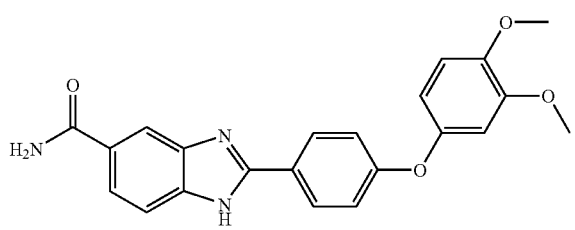

2-[4-(3,4-Dimethoxy-phenoxy)-phenyl]-1H-benzoimidazole-5-carboxylic acid amide.

This compound was prepared according to the methods described in Example 2 and Scheme 1, substituting 3,4-dimethoxyphenol for 3-chloro-4-methylphenol.

HPLC: $R_t$=6.76. MS (ESI+): mass calculated for $C_{22}H_{19}N_3O_4$, 389.14; m/z found 390.10 [M+H]$^+$. $^1$H NMR (400 MHz, DMSO-$d_6$): 8.17 (d, J=8.9 Hz, 2H), 8.15 (s, 1H), 8.06 (br s, 1H), 7.85 (d, J=8.4 Hz, 1H), 7.66 (d, J=8.4 Hz, 1H), 7.38 (br s, 1H), 7.15 (d, J=8.9 Hz, 2H), 7.01 (d, J=8.8 Hz, 1H), 6.83 (d, J=2.7 Hz, 1H), 6.67 (dd, J=8.7 Hz, J=2.7 Hz, 1H), 3.77 (s, 3H), 3.74 (s, 3H).

Example 24

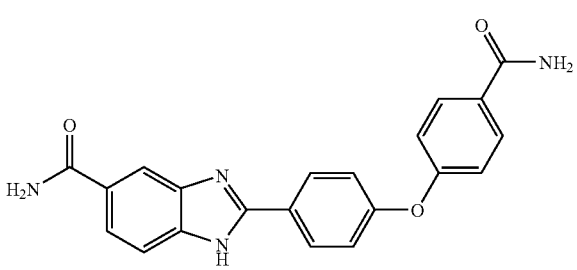

2-[4-(4-Carbamoyl-phenoxy)-phenyl]-1H-benzoimidazole-5-carboxylic acid amide.

This compound was prepared according to the methods described in Example 2 and Scheme 1, substituting 4-hydroxybenzamide for 3-chloro-4-methylphenol.

HPLC: $R_t$=5.77. MS (ESI+): mass calculated for $C_{21}H_{16}N_4O_3$, 372.12; m/z found, 373.1 [M+H]$^+$. $^1$H NMR (400 MHz, DMSO-$d_6$): 8.26-8.24 (m 2H), 8.20 (d, J=1.3 Hz, 1H), 8.11 (br, s, 1H), 7.99-7.96 (m, 3H), 7.91 (dd, J=8.6, 1.3 Hz, 1H), 7.28 (d, J=8.6 Hz, 1H), 7.43 (br, s, 1H), 7.34 (br, s, 1H), 7.30-7.33 (m, 2H), 7.17-7.19 (m, 2H).

Example 25

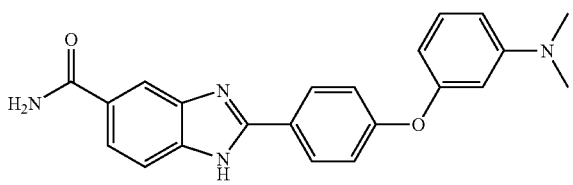

2-[4-(3-(N,N-Dimethyl)amino-phenoxy)-phenyl]-1H-benzoimidazole-5-carboxylic acid amide.

This compound was prepared according to the methods described in Example 2 and Scheme 1, substituting 3-(N,N-dimethylamino)-phenol for 3-chloro-4-methylphenol.

HPLC: $R_t$=6.16. MS (ESI+): mass calculated for $C_{22}H_{20}N_4O_2$, 372.16; m/z found 373.09 [M+H]$^+$. $^1$H NMR (400 MHz, DMSO-$d_6$): 8.18 (d, J=8.9 Hz, 2H), 8.13 (br s, 1H), 7.98 (br s, 1H), 7.77 (dd, J=8.4 Hz, J=1.6 Hz, 1H), 7.59 (br d, J=8.0 Hz, 1H), 7.27 (br s, 1H), 7.23 (t, J=8.2 Hz, 1H), 7.14 (d, J=8.9 Hz, 2H), 6.58 (m, 1H), 6.45 (t, J=2.3 Hz, 1H), 6.35 (m, 1H), 2.91 (s, 6H).

Example 26

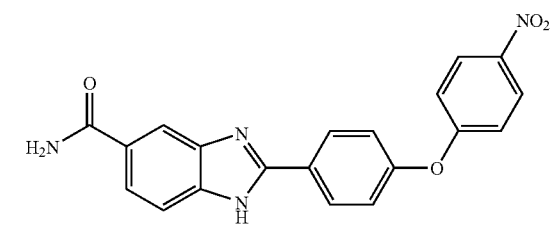

2-[4-(4-Nitro-phenoxy)-phenyl]-1H-benzoimidazole-5-carboxylic acid amide.

This compound was prepared according to the methods described in Example 22 and Scheme 3, substituting 4-(4-nitro-phenoxy)-benzaldehyde for 4-(4-fluoro-phenoxy)-benzaldehyde.

HPLC: $R_t$=6.99. MS (ESI+): mass calculated for $C_{20}H_{14}N_4O_4$, 374.10; m/z found, 375.1 [M+H]$^+$. $^1$H NMR (400 MHz, DMSO-$d_6$): 8.4-8.31 (m, 4H), 8.21 (s, 1H), 8.08 (br, s, 1H), 7.87 (d, J=8.5 Hz, 1H), 7.70 (d, J=8.5 Hz, 1H), 7.45 (d, J=8.6 Hz, 2H), 7.39 (br, s, 1H), 7.32-7.29 (m, 2H), 4.28 (br, s, 2H).

Example 27

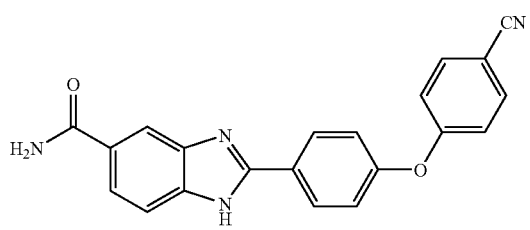

2-[4-(4-Cyano-phenoxy)-phenyl]-1H-benzoimidazole-5-carboxylic acid amide.

This compound was prepared according to the methods described in Example 22 and Scheme 3, substituting 4-(4-cyano-phenoxy)-benzaldehyde for 4-(4-fluoro-phenoxy)-benzaldehyde.

HPLC: $R_t$=6.75. MS (ESI+): mass calculated for $C_{21}H_{14}N_4O_2$, 354.11; m/z found, 355.1 $[M+H]^+$. $^1$H NMR (400 MHz, DMSO-$d_6$): 8.30 (d, J=8.7 Hz, 2H), 8.20 (s, 1H), 8.09 (br, s, 1H), 8.00-7.92 (m, 2H), 7.88 (dd, J=8.5, 1.4 Hz, 1H), 7.71 (d, J=8.5 Hz, 1H), 7.40 (d, J=8.7 Hz, 1H), 7.29-7.20 (m, 2H).

Example 28

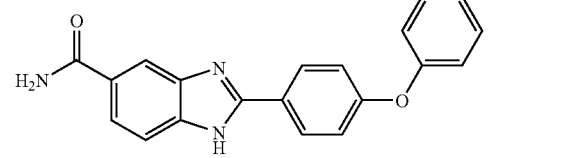

3-{4-[4-(5-Carbamoyl-1H-benzoimidazol-2-yl)-phenoxy]-phenyl}-propionic acid.

This compound was prepared according to the methods described in Example 2 and Scheme 1, substituting 4-phenoxy-propionic acid for 3-chloro-4-methylphenol.

HPLC: $R_t$=6.57. MS (ESI+): mass calculated for $C_{23}H_{19}N_3O_4$, 401.14; m/z found 402.1 $[M+H]^+$. $^1$H NMR (400 MHz, DMSO-$d_6$): 8.17 (d, J=8.5 Hz, 2H), 8.12 (br s, 1H), 7.97 (br s, 1H), 7.76 (d, J=8.4 Hz, 1H), 7.58 (d, J=8.3 Hz, 1H), 7.30 (d, J=8.3 Hz, 2H), 7.27 (br s, 1H), 7.12 (d, J=8.6 Hz, 2H), 7.04 (d, J=8.6 Hz, 2H), 2.83 (t, J=7.6 Hz, 2H), 2.55 (t, J=7.6 Hz, 2H).

Example 29

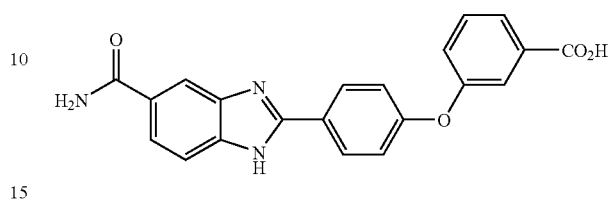

2-[4-(3-Carboxy-phenoxy)-phenyl]-1H-benzoimidazole-5-carboxylic acid amide.

This compound was prepared according to the methods described in Example 2 and Scheme 1, substituting 3-hydroxybenzoic acid for 3-chloro-4-methylphenol.

HPLC: $R_t$=6.42. MS (ESI+): mass calculated for $C_{21}H_{15}N_3O_4$, 373.11; m/z found 374.10 $[M+H]^+$. $^1$H NMR (400 MHz, DMSO-$d_6$): 13.00 (br s, 1H), 8.05 (d, J=8.8 Hz, 2H), 7.96 (br s, 1H), 7.80 (br s, 1H), 7.59 (m, 2H), 7.7 (br s, 1H), 7.40 (t, J=8.0 Hz, 1H), 7.36 (m, 1H), 7.23 (m, 1H), 7.09 (br s, 1H), 7.06 (d, J=8.9 Hz, 2H).

Example 30

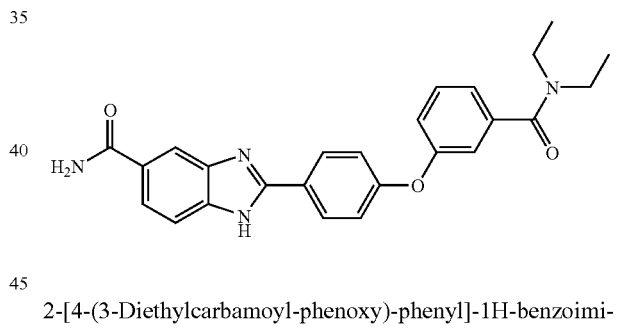

2-[4-(3-Diethylcarbamoyl-phenoxy)-phenyl]-1H-benzoimidazole-5-carboxylic acid amide.

Scheme 10. In a flask charged with 2-[4-(3-carboxyphenoxy)-phenyl]-1H-benzoimidazole-5-carboxylic acid amide (Example 29, 50 mg, 0.13 mmol), 1-(3-dimethylaminopropyl)-3-ethylcarbodiimide hydrochloride (36 mg, 0.19 mmol), 1-hydroxybenzotriazole hydrate (25 mg, 0.19 mmol) and N,N-dimethylformamide (5 mL), was added N,N-diethylamine (33 mg, 0.26 mmol). The mixture was stirred for 4 h at room temperature, and then diluted with ethyl acetate (100 mL/mmol), washed with saturated $NaHCO_3$ (2×50 mL/mmol) and water (4×50 mL/mmol), and dried with $Na_2SO_4$. Solvent was removed under reduced pressure to provide the title compound.

HPLC: $R_t$=6.78. MS (ESI+): mass calculated for $C_{25}H_{24}N_4O_3$, 428.18; m/z found 429.2 $[M+H]^+$. $^1$H NMR (400 MHz, DMSO-$d_6$): 8.17 (d, J=8.9 Hz, 2H), 8.12 (s, 1H), 8.02 (br s, 1H), 7.82 (dd, J=8.5 Hz, J=1.4 Hz, 1H), 7.63 (d, J=8.5 Hz, 1H), 7.46 (t, J=7.9 Hz, 1H), 7.33 (br s, 1H), 7.21 (d, J=8.9 Hz, 2H), 7.14 (m, 2H), 6.98 (m, 1H), 3.35 (br s, 2H), 3.11 (br s, 2H), 1.05 (br s, 3H), 0.97 (br s, 3H).

Example 31

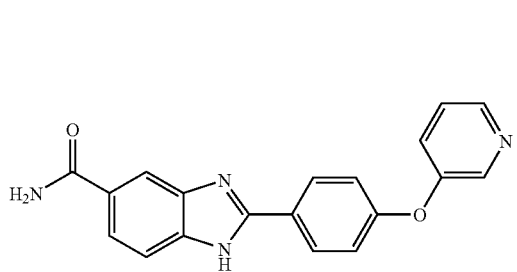

2-[4-(3-Pyridyloxy)-phenyl]-1H-benzoimidazole-5-carboxylic acid amide.

This compound was prepared according to the methods described in Example 22 and Scheme 3, substituting 4-(3-pyridyloxy)-benzaldehyde for 4-(4-fluoro-phenoxy)-benzaldehyde.

HPLC: $R_t$=5.20. MS (ESI+): mass calculated for $C_{19}H_{14}N_4O_2$, 330.11; m/z found, 331.1 [M+H]$^+$. $^1$H NMR (400 MHz, DMSO-d$_6$): 8.56 (d, J=2.8 Hz, 1H), 8.52 (dd, J=4.5, 1.4 Hz, 1H), 8.28-8.24 (m, 2H), 8.21 (d, J=1 Hz, 1H), 7.90 (dd, J=8.8, 1.2 Hz, 1H), 7.73 (s, 1H), 7.71-7.68 (m, 2H), 7.59-7.56 (m, 1H), 7.35-7.31 (m, 2H).

Example 32

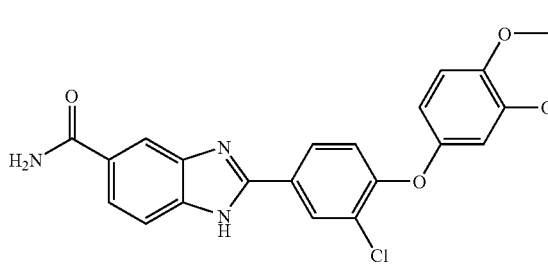

2-[3-Chloro-4-(3,4-dimethoxy-phenoxy)-phenyl]-1H-benzoimidazole-5-carboxylic acid amide.

This compound was prepared according to the methods described in Example 2 and Scheme 1, substituting 3,4-dimethoxyphenol for 3-chloro-4-methylphenol and 3-chloro-4-fluorobenzaldehyde for 4-fluorobenzaldehyde.

HPLC: $R_t$=7.06. MS (ESI+): mass calculated for $C_{22}H_{18}ClN_3O_4$, 423.10; m/z found 424.10 [M+H]$^+$. $^1$H NMR (400 MHz, DMSO-d$_6$): 8.36 (d, J=2.1 Hz, 1H), 8.14 (br s, 1H), 8.10 (dd, J=8.6 Hz, J=2.2 Hz, 1H), 8.01 (br s, 1H), 7.79 (dd, J=8.4 Hz, J=1.5 Hz, 1H), 7.61 (d, J=8.5 Hz, 1H), 7.31 (br s, 1H), 7.03 (m, 2H), 6.86 (d, J=2.8 Hz, 1H), 6.52 (dd, J=8.6 Hz, J=2.8 Hz, 1H), 3.76 (s, 3H), 3.75 (s, 3H).

Example 33

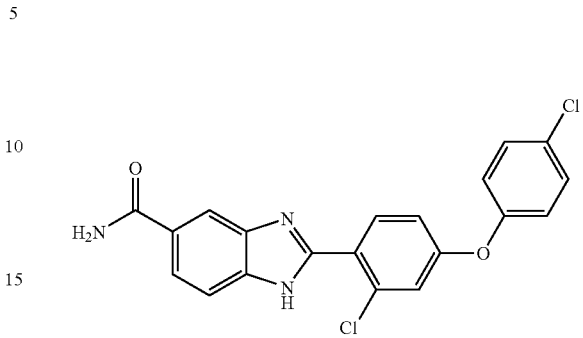

2-[2-Chloro-4-(4-chloro-phenoxy)-phenyl]-1H-benzoimidazole-5-carboxylic acid amide.

This compound was prepared according to the methods described in Example 2 and Scheme 1, substituting 4-chlorophenol for 3-chloro-4-methylphenol and 2-chloro-4-fluorobenzaldehyde for 4-fluorobenzaldehyde.

HPLC: $R_t$=7.51. MS (ESI+): mass calculated for $C_{20}H_{13}Cl_2N_3O_2$, 397.04; m/z found, 398.0 [M+H]$^+$. $^1$H NMR (400 MHz, DMSO-d$_6$): 8.22 (s, 1H), 8.03 (br s, 1H), 7.94 (d, J=8.4 Hz, 1H), 7.67 (d, J=8.4 Hz, 1H), 7.55-7.51 (m, 2H), 7.33 (d, J=2.8 Hz, 2H), 7.16 (dd, J=8.5, 2.2 Hz, 1H), 4.23 (br, s, 2H).

Example 34

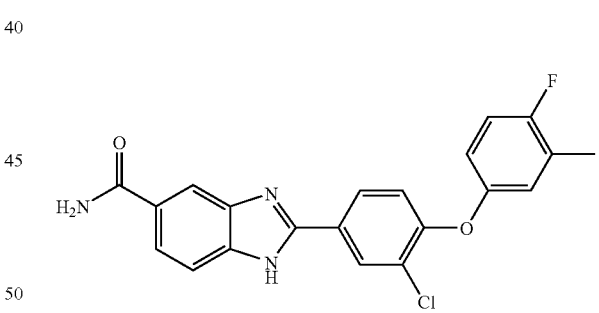

2-[3-Chloro-4-(4-fluoro-3-methyl-phenoxy)-phenyl]-1H-benzoimidazole-5-carboxylic acid amide.

This compound was prepared according to the methods described in Example 2 and Scheme 1, substituting 4-fluoro-3-methylphenol for 3-chloro-4-methylphenol and 3-chloro-4-fluorobenzaldehyde for 4-fluorobenzaldehyde.

HPLC: $R_t$=7.73. MS (ESI+): mass calculated for $C_{21}H_{15}ClFN_3O_2$, 395.08; m/z found 396.09 [M+H]$^+$. $^1$H NMR (400 MHz, DMSO-d$_6$): 8.41 (d, J=2.2 Hz, 1H), 8.18 (d, J=1.0 Hz, 1H), 8.14 (dd, J=8.6 Hz, J=2.2 Hz, 1H), 8.06 (br s, 1H), 7.84 (dd, J=8.5 Hz, J=1.6 Hz, 1H), 7.67 (d, J=8.5 Hz, 1H), 7.37 (br s, 1H), 7.24 (t, J=9.1 Hz, 1H), 7.16 (d, J=8.6 Hz, 1H), 7.12 (m, 1H), 7.0 (m, 1H).

Example 35

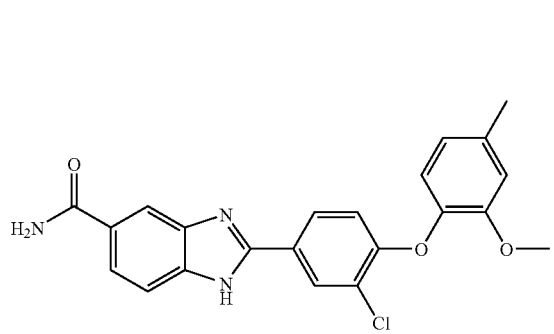

2-[3-Chloro-4-(2-methoxy-4-methyl-phenoxy)-phenyl]-1H-benzoimidazole-5-carboxylic acid amide.

This compound was prepared according to the methods described in Example 2 and Scheme 1, substituting 2-methoxy-4-methylphenol for 3-chloro-4-methylphenol and 3-chloro-4-fluorobenzaldehyde for 4-fluorobenzaldehyde.

HPLC: $R_t$=7.54. MS (ESI+): mass calculated for $C_{22}H_{18}ClN_3O_3$, 407.10; m/z found 408.10 [M+H]$^+$. $^1$H NMR (400 MHz, DMSO-d$_6$): 8.36 (d, J=2.2 Hz, 1H), 8.16 (d, J=1.0 Hz, 1H), 8.07 (br s, 1H), 8.04 (dd, J=8.7 Hz, J=2.2 Hz, 1H), 7.85 (dd, J=8.5 Hz, J=1.5 Hz, 1H), 7.66 (d, J=8.5 Hz, 1H), 7.38 (br s, 1H), 7.08 (m, 2H), 6.86 (dd, J=8.0 Hz, J=1.2 Hz, 1H), 6.79 (d, J=8.7 Hz, 1H), 3.74 (s, 3H), 2.37 (s, 3H).

Example 36

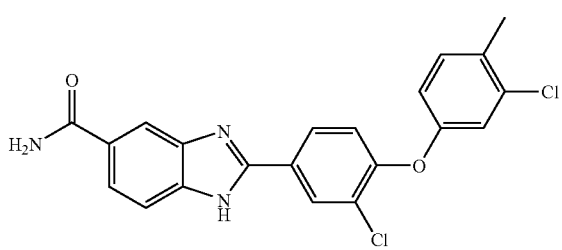

2-[3-Chloro-4-(3-chloro-4-methyl-phenoxy)-phenyl]-1H-benzoimidazole-5-carboxylic acid amide.

This compound was prepared according to the methods described in Example 2 and Scheme 1, substituting 3-chloro-4-fluorobenzaldehyde for 4-fluorobenzaldehyde.

HPLC: $R_t$=8.03. MS (ESI+): mass calculated for $C_{21}H_{15}Cl_2N_3O_2$, 411.05; m/z found 412.06 [M+H]$^+$. $^1$H NMR (400 MHz, DMSO-d$_6$): 8.42 (d, J=2.2 Hz, 1H), 8.17 (m, 2H), 8.06 (br s, 1H), 7.84 (dd, J=8.5 Hz, J=1.6 Hz, 1H), 7.67 (d, J=8.5 Hz, 1H), 7.43 (d, J=8.8 Hz, 1H), 7.36 (br s, 1H), 7.27 (d, J=8.6 Hz, 1H), 7.23 (d, J=2.5 Hz, 1H), 7.02 (dd, J=8.4 Hz, J=2.6 Hz, 1H), 2.33 (s, 3H).

Example 37

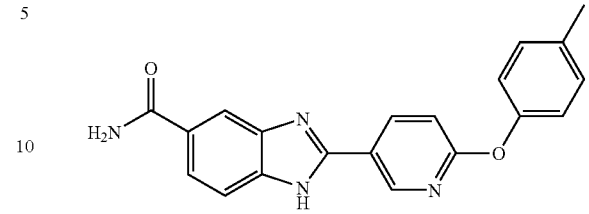

2-(6-p-Tolyloxy-pyridin-3-yl)-1H-benzoimidazole-5-carboxylic acid amide.

This compound was prepared according to the methods described in Example 22 and Scheme 3, substituting 6-p-tolyloxy-pyridine-3-carbaldehyde for 4-(4-fluoro-phenoxy)-benzaldehyde.

HPLC: $R_t$=6.86. MS (ESI+): mass found for $C_{20}H_{16}N_4O_2$, 344.13; m/z found 345.1 [M+H]$^+$. $^1$H NMR (400 MHz, DMSO-d$_6$): 8.90 (d, J=2.3 Hz, 1H), 8.55 (dd, J=8.8 Hz, J=2.7 Hz, 1H), 8.21 (br s, 1H), 7.99 (br s, 1H), 7.78 (d, J=8.0 Hz, 1H), 7.29 (br s, 1H), 7.26 (d, J=8.5 Hz, 2H), 7.18 (d, J=8.6 Hz, 1H), 7.09 (d, J=8.4 Hz, 2H) 2.34 (s, 3H).

Example 38

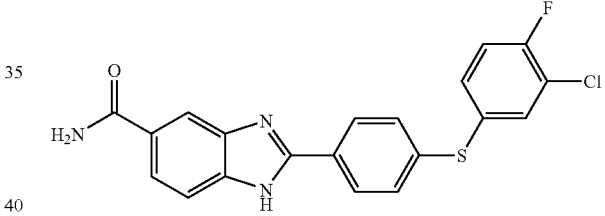

2-[4-(3-Chloro-4-fluoro-phenylsulfanyl)-phenyl]-1H-benzoimidazole-5-carboxylic acid amide.

This compound was prepared according to the methods described in Example 2 and Scheme 1, substituting 3-chloro-4-fluorobenzenethiol for 3-chloro-4-methylphenol.

HPLC: $R_t$=7.69. MS (ESI+): mass calculated for $C_{20}H_{13}ClFN_3OS$, 397.05; m/z found 398.07 [M+H]$^+$. $^1$H NMR (400 MHz, DMSO-d$_6$): 8.39 (d, J=8.5 Hz, 2H), 8.38 (s, 1H), 8.26 (br s, 1H), 8.05 (dd, J=8.4 Hz, J=1.6 Hz, 1H), 7.96 (dd, J=7.2 Hz, J=2.1 Hz, 1H), 7.87 (d, J=8.5 Hz, 1H), 7.74 (m, 1H), 7.73 (m, 1H), 7.71 (d, J=8.5 Hz, 2H).

Example 39

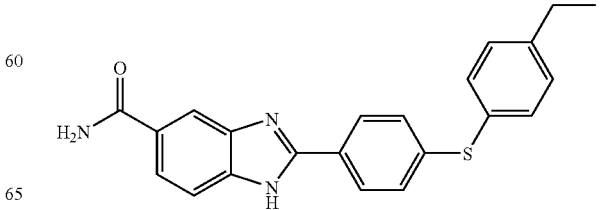

2-[4-(4-Ethyl-phenylsulfanyl)-phenyl]-1H-benzoimidazole-5-carboxylic acid amide.

This compound was prepared according to the methods described in Example 2 and Scheme 1, substituting 4-ethylbenzenethiol for 3-chloro-4-methylphenol.

HPLC: $R_t$=7.85. MS (ESI+): mass calculated for $C_{22}H_{19}N_3OS$, 373.12; m/z found 374.13 [M+H]$^+$. $^1$H NMR (400 MHz, DMSO-$d_6$): 7.97 (d, J=1.1 Hz, 1H), 7.92 (d, J=8.5 Hz, 2H), 7.86 (br s, 1H), 7.66 (dd, J=8.5 Hz, J=1.5 Hz, 1H), 7.48 (d, 8.5 Hz, 1H), 7.22 (d, J=8.2 Hz, 2H), 7.18 (d, J=8.5 Hz, 2H), 7.14 (d, J=8.2 Hz, 2H), 2.46 (q, J=7.6 Hz, 2H), 1.01 (t, J=7.6 Hz, 3H).

Example 40

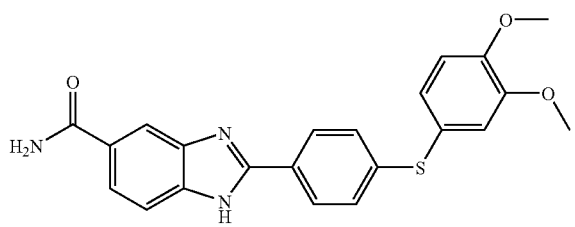

2-[4-(3,4-Dimethoxy-phenylsulfanyl)-phenyl]-1H-benzoimidazole-5-carboxylic acid amide.

This compound was prepared according to the methods described in Example 2 and Scheme 1, substituting 3,4-dimethoxybenzenethiol for 3-chloro-4-methylphenol.

HPLC: $R_t$=7.03. MS (ESI+): mass calculated for $C_{22}H_{19}N_3O_3S$, 405.11; m/z found 406.12 [M+H]$^+$. $^1$H NMR (400 MHz, DMSO-$d_6$): 8.16 (s, 1H), 8.08 (d, J=8.8 Hz, 2H), 8.08 (br s, 1H), 7.86 (dd, J=8.5 Hz, J=1.4 Hz, 1H), 7.67 (d, J=8.5 Hz, 1H), 7.39 (br s, 1H), 7.30 (d, J=8.6 Hz, 2H), 7.13 (m, 3H), 3.81 (s, 3H), 3.76 (s, 3H).

Example 41

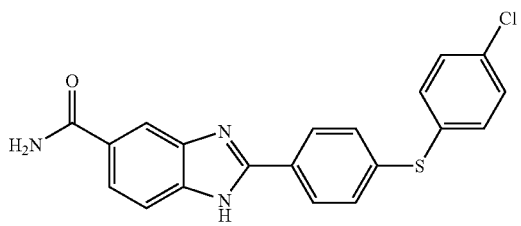

2-[4-(4-Chloro-phenylsulfanyl)-phenyl]-1H-benzoimidazole-5-carboxylic acid amide.

This compound was prepared according to the methods described in Example 2 and Scheme 1, substituting 4-chlorobenzenethiol for 3-chloro-4-methylphenol.

HPLC: $R_t$=7.57. MS (ESI+): mass calculated for $C_{20}H_{14}ClN_3OS$, 379.05; m/z found 380.00 [M+H]$^+$. $^1$H NMR (400 MHz, DMSO-$d_6$): 8.17 (d, J=8.7 Hz, 3H), 8.07 (br s, 1H), 7.85 (t, J=8.5 Hz, 2H), 7.68 (d, J=8.4 Hz, 1H), 7.56-7.48 (m, 6H), 7.37 (br s, 1H).

Example 42

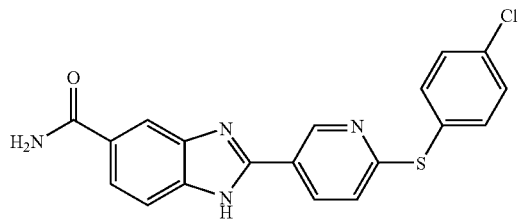

2-[6-(4-Chloro-phenylsulfanyl)-pyridin-3-yl]-1H-benzoimidazole-5-carboxylic acid amide.

This compound was prepared according to the methods described in Example 22 and Scheme 3, substituting 6-(4-chloro-phenylsulfanyl)-pyridine-3-carbaldehyde for 4-(4-fluoro-phenoxy)-benzaldehyde.

HPLC: $R_t$=7.32. MS (ESI+): mass calculated for $C_{19}H_{13}ClN_4OS$, 380.05; m/z found 381.0 [M+H]$^+$. $^1$H NMR (400 MHz, DMSO-$d_6$): 8.99 (d, J=2.5 Hz, 1H), 8.20 (dd, J=8.5 Hz, J=2.4 Hz, 1H), 8.01 (d, J=1.0 Hz, 1H), 7.87 (br s, 1H), 7.66 (dd, J=8.5 Hz, J=1.6 Hz, 1H), 7.51 (d, J=8.7 Hz, 2H), 7.50 (m, 2H), 7.44 (d, J=8.7 Hz, 2H), 7.18 (br s, 1H), 7.07 (dd, J=8.4 Hz, J=0.7 Hz, 1H).

Example 43

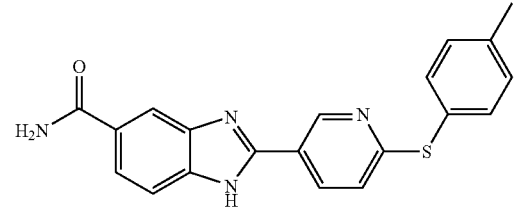

2-[6-(4-Methyl-phenylsulfanyl)-pyridin-3-yl]-1H-benzoimidazole-5-carboxylic acid amide.

This compound was prepared according to the methods described in Example 22 and Scheme 3, substituting 6-(4-methyl-phenylsulfanyl)-pyridine-3-carbaldehyde for 4-(4-fluoro-phenoxy)-benzaldehyde.

HPLC: $R_t$=7.19. MS (ESI+): mass calculated for $C_{20}H_{16}N_4OS$, 360.10; m/z found 361.1 [M+H]$^+$. $^1$H NMR (400 MHz, DMSO-$d_6$): 9.25 (s, 1H), 8.48 (d, J=8.5 Hz, 1H), 8.31 (s, 1H), 8.17 (br s, 1H), 7.97 (d, J=8.4 Hz, 1H), 7.80 (d, J=8.4 Hz, 1H), 7.70 (d, J=7.6 Hz, 2H), 7.52 (d, J=7.6 Hz, 2H), 7.48 (br s, 1H), 7.21 (d, J=8.6 Hz, 1H).2.54 (s, 3H).

Example 44

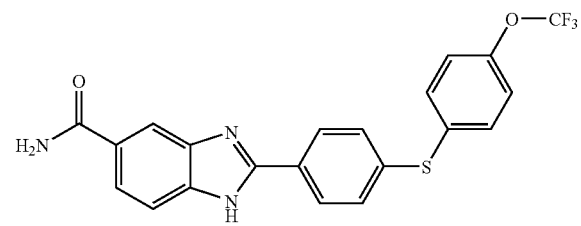

2-[4-(4-Trifluoromethoxy-phenylsulfanyl)-phenyl]-1H-benzoimidazole-5-carboxylic acid amide.

This compound was prepared according to the methods described in Example 2 and Scheme 1, substituting 4-trifluoromethoxybenzenethiol for 3-chloro-4-methylphenol.

HPLC: $R_t$=7.97. MS (ESI+): mass calculated for $C_{21}H_{14}F_3N_3O_2S$, 429.08; m/z found 430.06 [M+H]+. 1H NMR (400 MHz, DMSO-$d_6$): 8.19 (m, 3H), 8.06 (br s, 1H), 7.84 (dd, J=8.4 Hz, J=1.5 Hz, 1H), 7.67 (d, J=8.5 Hz, 1H), 7.57 (d, J=8.9 HZ, 2H), 7.53 (d, J=8.6 Hz, 2H), 7.46 (d, J=8.0 Hz, 2H), 7.37 (br s, 1H).

Example 45

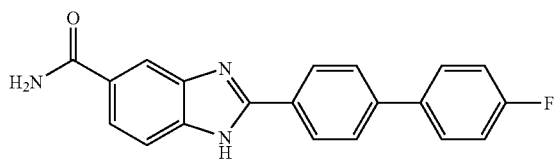

2-[4-(4-Fluoro-phenyl)-phenyl-1H-benzoimidazole-5-carboxylic acid amide.

This compound was prepared according to the methods described in Example 22 and Scheme 3, substituting 4-(4-fluoro-phenyl)-benzaldehyde for 4-(4-fluoro-phenoxy)-benzaldehyde.

HPLC: $R_t$=6.97. MS (ESI+): mass calculated for $C_{20}H_{14}FN_3$, 331.11; m/z found, 332.1 [M+H]+. 1H NMR (400 MHz, DMSO-$d_6$): 8.31 (d, J=8.5 Hz, 2H), 8.22 (s, 1H), 8.10 (br s, 1H), 7.96 (d, J=8.5 Hz, 2H), 7.91-7.86 (m, 3H), 7.72 (d, J=8.2 Hz, 1H), 7.46-7.36 (m, 3H). 4.07 (br s, 2H).

Example 46

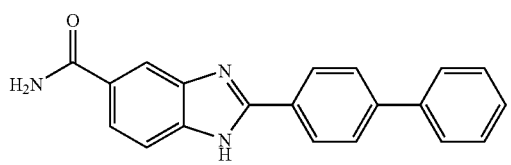

2-[4-Phenyl-phenyl]-1H-benzoimidazole-5-carboxylic acid amide.

This compound was prepared according to the methods described in Example 22 and Scheme 3, substituting 4-phenylbenzaldehyde for 4-(4-fluoro-phenoxy)-benzaldehyde.

HPLC: $R_t$=6.85. MS (ESI+): mass calculated for $C_{20}H_{15}N_3O$, 313.12; m/z found, 314.1 [M+H]+. 1H NMR (400 MHz, DMSO-$d_6$): 8.3 (d, J=8.4 Hz, 2H), 8.23 (s, 1H), 8.12 (br, s, 1H), 7.98 (d, J=8.4 Hz, 2H), 7.92 (dd, J=8.5, 1.7 Hz, 1H), 7.82 (d, J=8.5 Hz, 2H), 7.74 (d, J=8.5 Hz, 2H), 7.53 (t, J=7.6 Hz, 2H), 7.44 (t, J=7.5 Hz, 2H).

Example 47

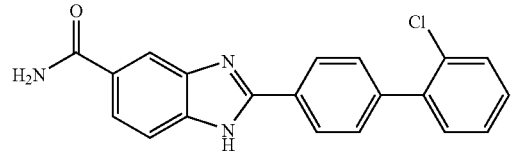

2-[4-(2-Chloro-phenyl)-phenyl]-1H-benzoimidazole-5-carboxylic acid amide.

This compound was prepared according to the methods described in Example 22 and Scheme 3, substituting 4-(2-chloro-phenyl)-benzaldehyde for 4-(4-fluoro-phenoxy)-benzaldehyde.

HPLC: $R_t$=7.07. MS (ESI+): mass calculated for $C_{20}H_{14}ClN_3O$, 347.08; m/z found, 348.1 [M+H]+. 1H-NMR (400 MHz, DMSO-$d_6$): 8.25 (dd, J=6.6, 1.7 Hz, 2H), 8.14 (s, 1H), 8.06 (br, s, 1H), 7.85 (d, J=8.5 Hz, 1H), 7.70-7.66 (m, 3H), 7.59-7.57 (m, 1H), 7.49-7.41 (m, 3H), 7.36 (br, s, 1H).

Example 48

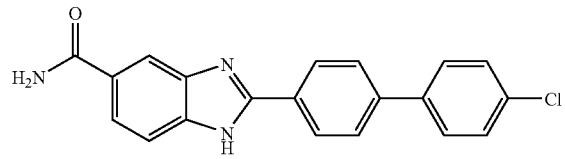

2-[4-(4-Chloro-phenyl)-phenyl]-1H-benzoimidazole-5-carboxylic acid amide.

This compound was prepared according to the methods described in Example 22 and Scheme 3, substituting 4-(4-chloro-phenyl)-benzaldehyde for 4-(4-fluoro-phenoxy)-benzaldehyde.

HPLC: Rt=7.29. MS (ESI+): mass calculated for $C_{20}H_{14}ClN_3O_2$, 347.08; m/z found, 348.0 [M+H]+. 1H NMR (400 MHz, DMSO-$d_6$): 8.31 (d, J=8.4 Hz, 2H), 8.21 (s, 1H), 8.09 (br, s, 1H), 7.97 (d, J=9.35 Hz, 2H), 7.89-7.84 (m, 3H), 7.83 (d, J=8.5 Hz, 1H), 7.61-7.57 (m, 2H), 7.39 (br, s, 1H).

Example 49

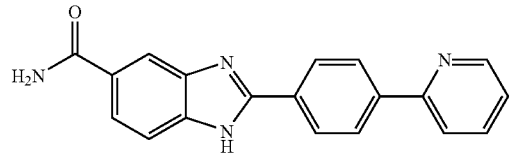

2-[4-(2-Pyridyl)-phenyl]-1H-benzoimidazole-5-carboxylic acid amide.

This compound was prepared according to the methods described in Example 22 and Scheme 3, substituting 4-(2-pyridyl)-benzaldehyde for 4-(4-fluoro-phenoxy)-benzaldehyde.

HPLC: $R_t$=5.31. MS (ESI+): mass calculated for $C_{19}H_{14}N_4O$, 314.12; m/z found, 315.1 [M+H]+. 1H NMR (400 MHz, DMSO-d$_6$); 8.59-8.50 (m, 1H), 8.21-8.16 (m, 5H), 8.05 (s, 1H), 7.98 (d, J=8.0 Hz, 1H), 7.84-7.79 (m, 1H), 7.71 (dd, J=8.6, 1.5 Hz, 1H), 7.54 (d, J=8.1 Hz, 1H), 7.30-7.27 (m, 2H).

Example 50

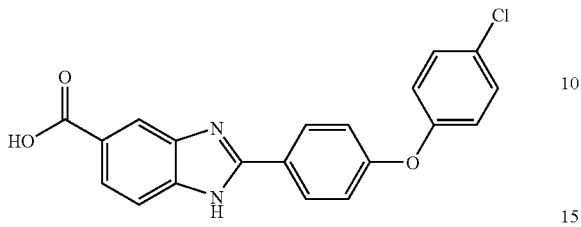

2-[4-(4-Chloro-phenoxy)-phenyl]-1H-benzoimidazole-5-carboxylic acid.

A. 4-(4-chloro-phenoxy)-benzaldehyde. Scheme 2. To a solution of 4-chlorophenol (19.2 g, 150 mmol) in N,N-dimethylformamide (250 mL) was added Cs$_2$CO$_3$ (48.7 g, 150 mmol) and 4-fluorobenzaldehyde (12.4 g, 100 mmol). The reaction was heated for 3 h at 80° C. The reaction mixture was then cooled to room temperature, diluted with water (2 L) and extracted with ether (3×500 mL). The organics were washed with 1 N KOH (2×) and water (2×), and dried over K$_2$CO$_3$. The solvent was removed in vacuo to afford 21.07 g (90%) of a tan powder.

HPLC: R$_t$=10.0. MS (ESI+): mass calculated for C$_{13}$H$_9$O$_2$Cl, 232.03; m/z found, 232.9 [M+H]$^+$. $^1$H-NMR (400 MHz, CDCl$_3$): 9.94 (s, 1H), 7.87 (d, J=6.7 Hz, 2H), 7.38 (d, J=6.7 Hz, 2H), 7.06 (m, 4H).

B. 2-[4-(4-chloro-phenoxy)-phenyl]-1H-benzoimidazole-5-carboxylic acid. To a solution of the above aldehyde (7.3 g, 31.5 mmol) in N,N-dimethyl acetamide (100 mL) was added 3,4-diaminobenzoic acid (4.8 g, 31.5 mmol) and Na$_2$S$_2$O$_5$ (7.2 g, 37.8 mmol). The mixture was heated to 100° C. for 6.5 h. The reaction mixture was then cooled, diluted with ethyl acetate (2 L), washed with water (5×500 mL), dried (MgSO$_4$), and concentrated in vacuo. The crude product was triterated with CH$_2$Cl$_2$ and methanol (50 mL, 20:1). The gray solid was collected on a sintered-glass filter and washed with CH$_2$Cl$_2$ (3×) to provide 8.0 g (70%) of the title compound.

HPLC: R$_t$=7.75. MS (ESI−): mass calculated for C$_{20}$H$_{13}$N$_2$O$_3$Cl, 364.06; m/z found, 363.1 [M−H]$^-$. $^1$H-NMR (400 MHz, DMSO-d$_6$): 8.12 (d, J=8.9 Hz, 2H), 8.06 (br s, 1H), 7.74 (d, J=8.4 Hz, 1H), 7.55 (br d, J=7.6 Hz, 1H), 7.40 (d, J=8.9 Hz, 2H), 7.11 (d, J=8.9 Hz, 2H), 7.07 (d, J=8.9 Hz, 2H).

Example 51

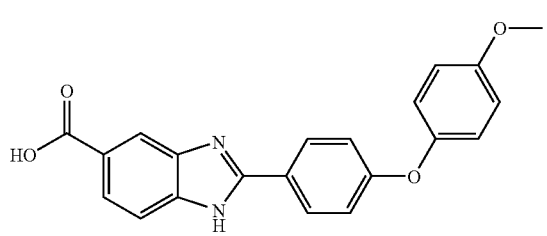

2-[4-(4-Methoxy-phenoxy)-phenyl]-1H-benzoimidazole-5-carboxylic acid.

This compound was prepared according to the methods described in Example 50 and Scheme 2, substituting 4-methoxyphenol for 4-chlorophenol.

HPLC: R$_t$=7.30. MS (ESI+): mass calculated for C$_{21}$H$_{16}$N$_2$O$_4$, 360.11; m/z found, 361.1 [M+H]$^+$.

Example 52

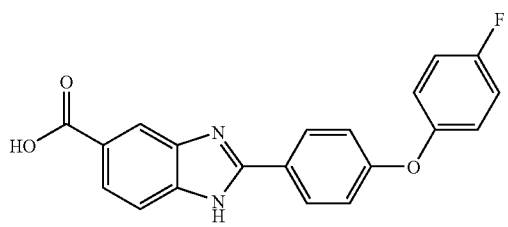

2-[4-(4-Fluoro-phenoxy)-phenyl]-1H-benzoimidazole-5-carboxylic acid.

This compound was prepared according to the methods described in Example 50 and Scheme 2, substituting 4-fluorophenol for 4-chlorophenol.

HPLC: R$_t$=7.40. MS (ESI+): mass calculated for C$_{20}$H$_{13}$FN$_2$O$_3$, 348.09; m/z found, 349.0 [M+H]$^+$. $^1$H NMR (400 MHz, DMSO-d$_6$): 8.22-8.19 (m, 3H), 7.90 (dd, J=8.4, 1.5 Hz, 1H), 7.71 (d, J=8.4 Hz, 1H), 7.34-7.29 (m, 2H), 7.25-7.18 (m, 4H).

Example 53

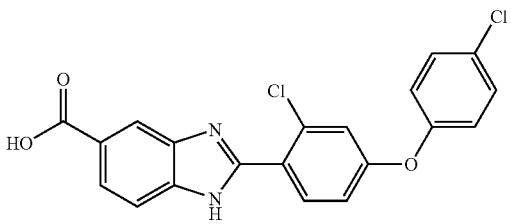

2-[2-Chloro-4-(4-chloro-phenoxy)-phenyl]-1H-benzoimidazole-5-carboxylic acid.

This compound was prepared according to the methods described in Example 50 and Scheme 2, substituting 2-chloro-4-fluorobenzaldehyde for 4-fluorobenzaldehyde.

HPLC: R$_t$=7.94. MS (ESI+): mass calculated for C$_{20}$H$_{12}$Cl$_2$N$_2$O$_3$, 398.02; m/z found, 399.0 [M+H]$^+$. $^1$H NMR (400 MHz, DMSO-d$_6$); 8.22 (s, 1H), 7.97 (d, J=8.6 Hz, 1H), 7.86 (dd, J=8.4, 1.5 Hz, 1H), 7.70 (d, J=8.5 Hz, 1H), 7.56-7.52 (m, 2H), 7.33 (d, J=2.5 Hz, 1H), 7.25-7.21 (m, 2H), 7.15 (dd, J=8.6, 2.4 Hz, 1H).

Example 54

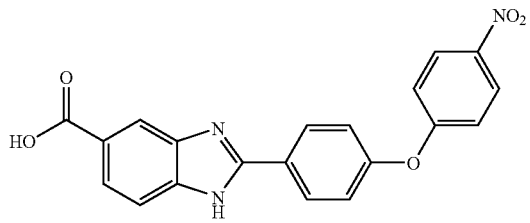

2-[4-(4-Nitro-phenoxy)-phenyl]-1H-benzoimidazole-5-carboxylic acid.

This compound was prepared according to the methods described in Example 50 and Scheme 2, substituting 4-nitrophenol for 4-chlorophenol.

HPLC: $R_t$=7.36. MS (ESI+): mass calculated for $C_{20}H_{13}N_3O_5$, 375.09; m/z found, 376.0 [M+H]$^+$. $^1$H NMR (400 MHz, DMSO-$d_6$); 8.23-8.28 (m, 4H), 8.19 (br, s, 1H), 7.85 (dd, J=8.4, 1.4 Hz, 1H), 7.67 (d, J=8.4 Hz, 1H), 7.30-7.28 (m, 2H), 7.18-7.16 (m, 2H).

Example 55

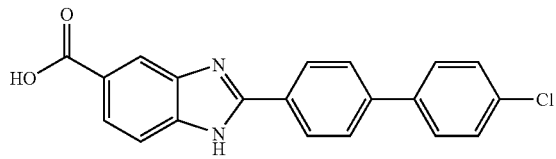

2-[4-(4-Chloro-phenyl)-phenyl]-1H-benzoimidazole-5-carboxylic acid.

This compound was prepared according to the methods described in Example 22 and Scheme 3, substituting 4-(4-chloro-phenyl)-benzaldehyde for 4-(4-fluoro-phenoxy)-benzaldehyde, and 3,4-diamino benzoic acid for 3,4-diamino benzoic acid amide.

HPLC: $R_t$=7.66. MS (ESI+): mass calculated for $C_{20}H_{13}N_2O_2$, 348.07; m/z found, 349.0 [M+H]$^+$. $^1$H NMR (400 MHz, DMSO-$d_6$); 8.29-8.27 (m, 2H), 8.19 (d, J=1.0 Hz, 1H), 7.94-7.92 (m, 2H), 7.87 (dd, J=8.6, 1.5 Hz, 1H), 7.87-7.80 (m, 2H), 7.70 (d, J=8.6 Hz, 1H), 7.58-7.54 (m, 2H).

Example 56

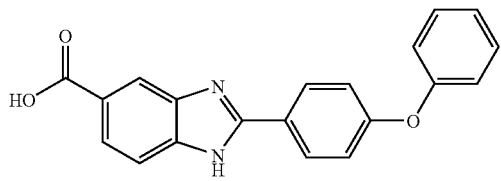

2-[4-Phenoxy-phenyl]-1H-benzoimidazole-5-carboxylic acid.

This compound was prepared according to the methods described in Example 22 and Scheme 3, substituting 4-phenoxybenzaldehyde for 4-(4-fluoro-phenoxy)-benzaldehyde, and 3,4-diaminobenzoic acid for 3,4-diaminobenzoic acid amide.

HPLC: $R_t$=7.22. MS (ESI+): mass calculated for $C_{20}H_{14}N_2O_3$, 330.10; m/z found, 331.1 [M+H]$^+$. $^1$H NMR (400 MHz, DMSO-$d_6$); 8.15-8.10 (m, 3H), 7.82 (dd, J=8.4, 1.5 Hz, 1H), 7.52 (d, J=8.8 Hz, 1H), 7.41-7.36 (m, 2H), 7.18-7.05 (m, 5H).

Example 57

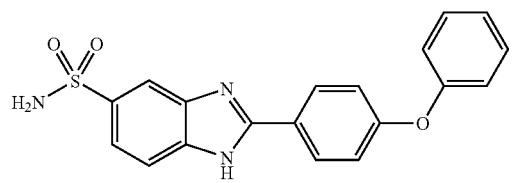

2-(4-Phenoxy-phenyl]-1H-benzoimidazole-5-sulfonic acid amide.

This compound was prepared according to the methods described in Example 22 and Scheme 3, substituting 4-phenoxybenzaldehyde for 4-(4-fluoro-phenoxy)-benzaldehyde, and 3,4-diaminobenzene sulfonamide for 3,4-diaminobenzoic acid amide.

MS (ESI+): mass calculated for $C_{19}H_{15}N_3O_3$, 365.08; m/z found, 366.1 [M+H]$^+$.

HPLC: $R_t$=7.21.

Example 58

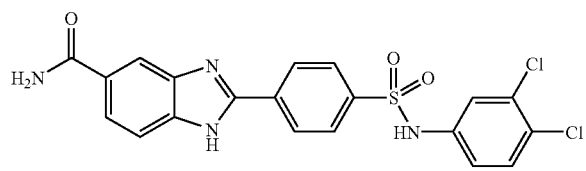

2-[4-(3,4-Dichloro-phenylsulfamoyl)-phenyl]-1H-benzoimidazole-5-carboxylic acid amide.

A. N-(3,4-Dichloro-phenyl)-4-formyl-benzenesulfonamide. Scheme 4. To a stirred solution of 3,4-dichloroaniline (174 mg, 1.07 mmol) and pyridine (0.08 mL, 1.07 mmol) in $CH_2Cl_2$ (4.0 mL), was added 200 mg (0.98 mmol) of 4-formylbenzenesulfonyl chloride. The mixture was stirred at room temperature for 16 h under $N_2$. The solvent was removed under reduced pressure to give a red semi-solid. Purification by chromatography (silica gel, 5% methanol/$CH_2Cl_2$) afforded 242 mg (75%) of N-(3,4-dichloro-phenyl)-4-formyl-benzenesulfonamide as a pale tan solid.

TLC (silica, 5% methanol/$CH_2Cl_2$): $R_f$=0.4.

HPLC: $R_t$=9.33. MS (ESI−): mass calculated for $C_{13}H_9Cl_2NO_3S$, 328.97; m/z found, 328.0 [M−H]$^-$. $^1$H NMR (400 MHz, $CD_3OD$): 10.61 (s, 1H), 8.09 (d, J=8.6 Hz, 2H), 8.04 (d, J=8.5 Hz, 2H), 7.42 (d, J=8.7 Hz, 1H), 7.34 (d, J=2.5 Hz, 1H), 7.06-7.04 (dd, J=8.6, 2.6 Hz, 2H).

B. 2-[4-(3,4-Dichloro-phenylsulfamoyl)-phenyl]-1H-benzoimidazole-5-carboxylic acid amide. 3,4-Diamino-benzamide (50 mg, 0.33 mmol), N-(3,4-dichloro-phenyl)-4-formyl-benzenesulfonamide (109 mg, 0.33 mmol) and $Na_2S_2O_5$ (82 mg, 0.43 mmol) were dissolved in N,N-dimethyl acetamide (2.0 mL) and stirred at 100° C. for 16 h. The mixture was then cooled and added dropwise to ice water (150 mL). The resulting pink precipitate was filtered, washed with hexanes (50 mL), and dried ($MgSO_4$). Purification by chromatography (silica gel, 1% methanol saturated with ammonia/9% methanol/$CH_2Cl_2$) afforded 130 mg (85%) of the title compound.

TLC (silica, 1% methanol saturated with ammonia/9% methanol/$CH_2Cl_2$): $R_f$=0.2. HPLC: $R_t$=7.53. MS (ESI+): mass calculated for $C_{20}H_{14}Cl_2N_4O_3S$, 460.02; m/z found, 461.0 [M+H]$^+$. $^1$H NMR (400 MHz, $CD_3OD$): 8.21 (d, J=8.6 Hz, 2H), 8.19 (br s, 1H), 7.93 (d, J=8.6 Hz, 2H), 7.82 (br d, J=8.5 Hz, 1H), 7.64 (br d, J=7.7 Hz, 1H), 7.34 (d, J=8.7 Hz, 1H), 7.28 (d, J=2.5 Hz, 1H), 7.06-7.03 (dd, J=8.7, 2.5 Hz, 1H).

Example 59

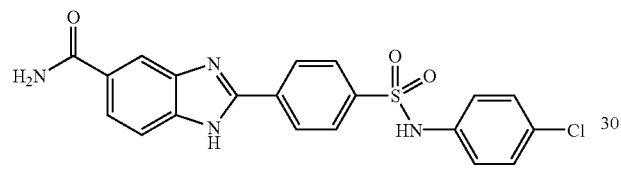

2-[4-(4-Chloro-phenylsulfamoyl)-phenyl]-1H-benzoimidazole-5-carboxylic acid amide.

This compound was prepared according to the methods described in Example 58 and Scheme 4, substituting 4-chloroaniline for 3,4-dichloroaniline.

TLC (silica, 1% methanol saturated with ammonia/9% methanol/$CH_2Cl_2$): $R_f$=0.3. HPLC: $R_t$=7.20. MS (ESI+): mass calculated for $C_{20}H_{15}ClN_4O_3S$, 426.06; m/z found, 427.0 [M+H]$^+$. $^1$H NMR (400 MHz, $CD_3OD$): 8.18 (d, J=8.7 Hz, 3H), 7.89 (d, J=8.7 Hz, 2H), 7.87-7.80 (m, 1H), 7.65-7.63 (br m, 1H), 7.20 (d, J=8.9 Hz, 2H), 7.08 (d, J=8.9 Hz, 2H).

Example 60

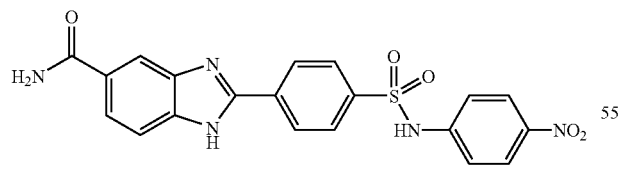

2-[4-(4-Nitro-phenylsulfamoyl)-phenyl]-1H-benzoimidazole-5-carboxylic acid amide.

This compound was prepared according to the methods described in Example 58 and Scheme 4, substituting 4-nitroaniline for 3,4-dichloroaniline.

HPLC: $R_t$=5.61. MS (ESI+): mass calculated for $C_{20}H_{15}N_2O_5S$, 437.08; m/z found, 438.1 [M+H]$^+$. $^1$H NMR (400 MHz, $CD_3OD$): 8.22 (s, 1H), 8.16 (d, J=8.6 Hz, 2H), 7.81 (s, 1H), 7.79 (d, J=8.7 Hz, 2H), 7.70 (s, 1H), 6.77 (d, J=8.7 Hz, 2H), 6.53 (d, J=8.7 Hz, 2H).

Example 61

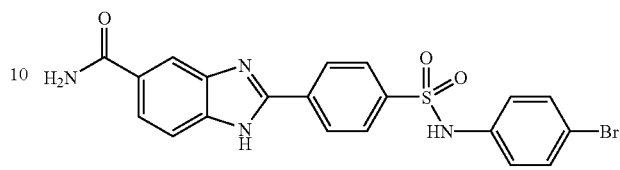

2-[4-(4-Bromo-phenylsulfamoyl)-phenyl]-1H-benzoimidazole-5-carboxylic acid amide.

This compound was prepared according to the methods described in Example 58 and Scheme 4, substituting 4-bromoaniline for 3,4-dichloroaniline.

TLC (silica, 1% methanol saturated with ammonia/9% methanol/$CH_2Cl_2$): $R_f$=0.2. HPLC: $R_t$=7.27. MS (ESI+): mass calculated for $C_{20}H_{15}BrN_4O_3S$, 470.00; m/z found, 471.0 [M+H]$^+$. $^1$H NMR (400 MHz, $CD_3OD$): 8.20 (br s, 1H), 8.19 (d, J=8.6 Hz, 2H), 7.81 (s, 1H), 7.90 (d, J=8.6 Hz, 2H), 7.83-7.81 (br m, 1H), 7.35 (d, J=8.8 Hz, 2H), 7.03 (d, J=8.8 Hz, 2H).

Example 62

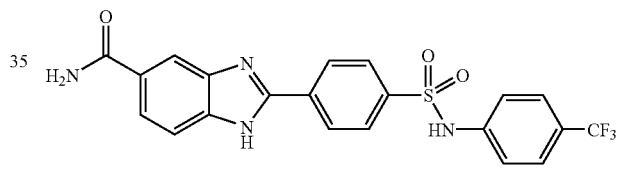

2-[4-(4-Trifluoromethyl-phenylsulfamoyl)-phenyl]-1H-benzoimidazole-5-carboxylic acid amide.

This compound was prepared according to the methods described in Example 58 and Scheme 4, substituting 4-trifluoromethylaniline for 3,4-dichloroaniline.

TLC (silica, 1% methanol saturated with ammonia/9% methanol/$CH_2Cl_2$): $R_f$=0.1. HPLC: $R_t$=7.37. MS (ESI+): mass calculated for $C_{21}H_{15}F_3N_4O_3S$, 460.08; m/z found, 461.12 [M+H]$^+$. $^1$H NMR (400 MHz, $CD_3OD$): 8.20 (d, J=8.65 Hz, 2H), 8.18 (s, 1H), 7.98 (d, J=8.6 Hz, 2H), 7.83-7.80 (dd, J=8.5, 1.6 Hz, 1H), 7.64 (d, J=8.5 Hz, 1H), 7.51 (d, J=8.5 Hz, 2H), 7.30 (d, J=8.5 Hz, 2H).

Example 63

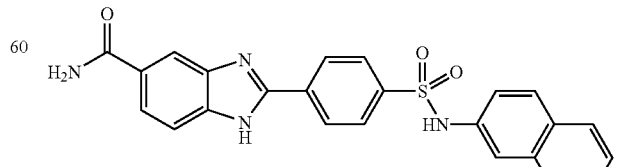

2-[4-(2-Naphthylsulfamoyl)-phenyl]-1H-benzoimidazole-5-carboxylic acid amide.

This compound was prepared according to the methods described in Example 58 and Scheme 4, substituting 2-aminonaphthalene for 3,4-dichloroaniline.

TLC (silica, 1% methanol saturated with ammonia/9% methanol/CH$_2$Cl$_2$): $R_f$=0.2. HPLC: $R_t$=7.31. MS (ESI+): mass calculated for C$_{24}$H$_{18}$N$_4$O$_3$S, 442.11; m/z found, 443.14 [M+H]$^+$. $^1$H NMR (400 MHz, CD$_3$OD): 8.14 (br s, 1H), 8.12 (d, J=8.5 Hz, 2H), 7.91 (d, J=8.5 Hz, 2H), 7.80-7.77 (dd, J=8.5, 1.4 Hz, 1H), 7.72-7.69 (m, 2H), 7.66 (d, J=8.0 Hz, 1H), 7.60 (br d, J=8.0 Hz, 1H), 7.54 (d, J=2.0 Hz, 1H), 7.40-7.31 (m, 2H), 7.27-7.24 (dd, J=8.8, 2.2 Hz, 1H).

Example 64

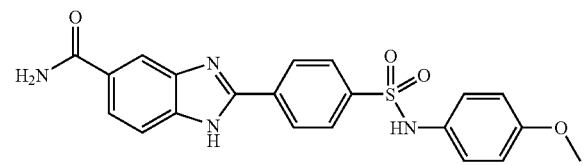

2-[4-(4-Methoxy-phenylsulfamoyl)-phenyl]-1H-benzoimidazole-5-carboxylic acid amide.

This compound was prepared according to the methods described in Example 58 and Scheme 4, substituting 4-methoxyaniline for 3,4-dichloroaniline.

TLC (silica, 1% methanol saturated with ammonia/9% methanol/CH$_2$Cl$_2$): $R_f$=0.2. HPLC: $R_t$=6.80. MS (ESI+): mass calculated for C$_{21}$H$_{18}$N$_4$O$_4$S, 422.10; m/z found, 423.09 [M+H]$^+$. $^1$H NMR (400 MHz, CD$_3$OD): 8.18 (s, 1H), 8.16 (d, J=8.5 Hz, 2H), 7.82-7.79 (m, 3H), 7.64 (d, J=8.5 Hz, 1H), 6.97 (d, J=9.0 Hz, 2H), 6.75 (d, J=9.0 Hz, 2H.), 3.68 (s, 3H).

Example 65

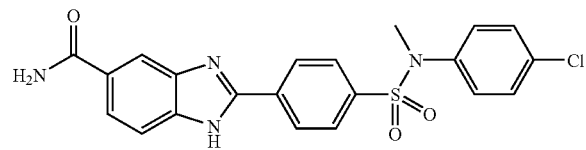

2-{4-[(4-Chloro-phenyl)-methyl-sulfamoyl]-phenyl}-1H-benzoimidazole-5-carboxylic acid amide.

This compound was prepared according to the methods described in Example 58 and Scheme 4, substituting 4-chloro-N-methyl-aniline for 3,4-dichloroaniline.

HPLC: $R_t$=7.52. MS (ESI+): mass calculated for C$_{21}$H$_{17}$ClN$_4$O$_3$S, 440.07; m/z found, 441.0 [M+H]$^+$. $^1$H NMR (400 MHz, CD$_3$OD): 8.17 (d, J=8.5 Hz, 2H), 8.1 (br s, 1H), 7.76 (br s, 1H), 7.62 (d, J=8.5 Hz, 2H), 7.56 (br s, 1H), 7.25 (d, J=8.8 Hz, 2H), 7.05 (d, J=8.8 Hz, 2H), 3.14 (s, 3H).

Example 66

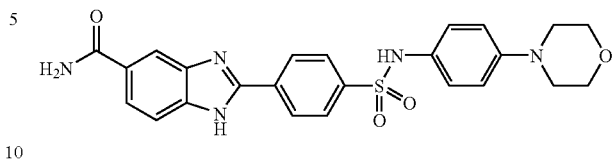

2-[4-(4-Morpholino-4-yl-phenylsulfamoyl)-phenyl]-1H-benzoimidazole-5-carboxylic acid amide.

This compound was prepared according to the methods described in Example 58 and Scheme 4, substituting 4-morpholinoaniline for 3,4-dichloroaniline.

HPLC: $R_t$=6.30. MS (ESI+): mass calculated for C$_{24}$H$_{23}$N$_5$O$_4$S, 477.15; m/z found, 478.1 [M+H]$^+$. $^1$H NMR (400 MHz, CD$_3$OD): 8.11 (br s, 1H), 8.10 (d, J=8.7 Hz, 2H), 7.76 (d, J=8.7 Hz, 3H), 7.58 (br s, 1H), 6.91 (d, J=9.0 Hz, 2H), 6.74 (d, J=9.0 Hz, 2H), 3.68 (t, J=4.8 Hz, 4H), 2.96 (t, J=4.8 Hz, 4H).

Example 67

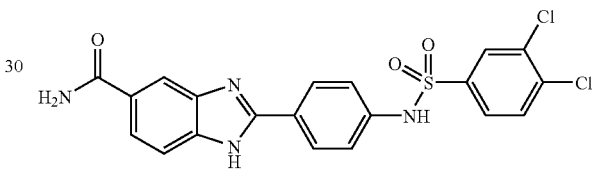

2-[4-(3,4-Dichloro-benzenesulfonylamino)-phenyl]-1H-benzoimidazole-5-carboxylic acid amide.

A. 4-Amino-benzaldehyde. Scheme 7. To a stirred solution of 4-nitro-benzaldehyde (1.0 g, 6.6 mmol) in ethanol (90 mL) was added tin (II) chloride dihydrate (7.5 g, 33 mmol). The mixture was heated to reflux for 4 h, cooled to room temperature, and then poured onto ice. The reaction mixture was treated with saturated NaHCO$_3$ until the pH was 7-8, and was then extracted with ethyl acetate. The organics were then washed with brine, dried (Na$_2$CO$_3$), and concentrated to afford 600 mg (75%) of 4-amino-benzaldehyde.

B. 2-(3-Nitro-phenyl)-1H-benzoimidazole-5-carboxylic acid amide. To a flask containing crude 4-amino-benzaldehyde (100 mg, 0.82 mmol), pyridine (0.15 mL, 1.87 mmol) and CH$_2$Cl$_2$ (4 mL), was added 3,4-dichlorobenzenesulfonyl chloride (184 mg, 0.75 mmol). The mixture was stirred for 16 h at room temperature, and was then cooled and concentrated. The crude product was purified by silica gel flash chromatography (eluted with 5% methanol/CH$_2$Cl$_2$) to provide 179 mg (72%) of 3,4-dichloro-N-(4-formyl-phenyl)-benzenesulfonamide.

HPLC: $R_t$=9.18. MS (ESI−): mass calculated for C$_{13}$H$_9$Cl$_2$NO$_3$S, 328.9; m/z found, 328.0 [M+H]$^-$. $^1$H NMR (400 MHz, CDCl$_3$): 9.91 (s, 1H), 7.97 (d, J=2.1, 1H), 7.81 (d, J=8.7, 3H), 7.69-7.66 (d, J=8.4, 2.1, 1H), 7.55 (d, J=8.4, 1H), 7.29 (d, J=8.5, 2H).

C. 2-[4-(3,4-Dichloro-benzenesulfonylamino)-phenyl]-1H-benzoimidazole-5-carboxylic acid amide. To a flask containing 3,4-dichloro-N-(4-formyl-phenyl)-benzenesulfonamide (109 mg, 0.33 mmol), 3,4-diaminobenzamide (50 mg, 0.33 mmol) and N,N-dimethyl acetamide (1.0 mL), was added Na$_2$S$_2$O$_5$ (80 mg, 0.42 mmol). The mixture was stirred for 24 h at 100° C., and was then cooled to room temperature. The reaction mixture was diluted with water, and the resulting precipitate was collected by filtration and washed with hexanes. Purification by silica gel flash chromatography (eluted with 1% methanol saturated with ammonia/9% methanol/CH$_2$Cl$_2$) afforded 80 mg (53%) of the title compound.

HPLC: R$_t$=7.14 min. MS (ESI+): mass calculated for C$_{20}$H$_{14}$Cl$_2$N$_4$O$_3$S, 460.02; m/z found, 461.0 [M+H]$^+$. $^1$H NMR (400 MHz, CD$_3$OD): 8.05 (br s, 1H), 7.91 (d, J=8.7, 2H), 7.86 (d, J=1.9, 1H), 7.70 (br d, J=8.3, 1H), 7.63-7.60 (dd, J=8.4, 2.0, 1H), 7.57 (d, J=8.4, 1H), 7.52 (br s, 1H), 7.21 (d, J=8.8, 2H).

Example 68

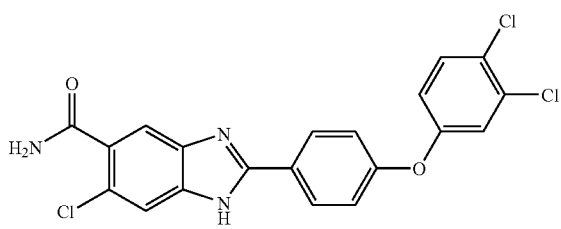

6-Chloro-2-[4-(3,4-dichloro-phenoxy)-phenyl]-1H-benzoimidazole-5-carboxylic acid amide.

A. 4-Acetylamino-2-chlorobenzoic acid. Scheme 5. To a flask containing 4-amino-2-chlorobenzoic acid (2.0 g, 11.69 mmol) in CH$_2$Cl$_2$/tetrahydrofuran (40 mL, 1:1) was added triethylamine (2.3 g, 2.33 mmol) and acetyl chloride (1.2 g, 14.02 mmol). The mixture was stirred for 2 h at room temperature and was then diluted with water (5 mL) and extracted with CH$_2$Cl$_2$. The organics were concentrated and then triturated with CH$_2$Cl$_2$. The resulting solid was collected by filtration and dried under vacuum to provide 2.3 g (92%) of the title compound.

HPLC: R$_t$=6.05. MS (ESI-): mass calculated for C$_9$H$_8$ClNO$_3$, 213.02; m/z found, 212.2 [M-H]$^-$.

B. 4-Acetylamino-2-chloro-5-nitrobenzoic acid. 4-Acetylamino-2-chlorobenzoic acid (0.10 g, 0.47 mmol) was dissolved in sulfuric acid (1 mL) at 0° C. Nitric acid (0.03 g, 0.47 mmol) was added, and the mixture was stirred for 2 h at room temperature. The reaction mixture was then poured onto ice water and extracted with ethyl acetate. The organic layer was concentrated to give 100 mg (82%) of 4-acetylamino-2-chloro-5-nitrobenzoic acid.

HPLC: R$_t$=7.25. MS (ESI-): mass calculated for C$_9$H$_7$ClN$_2$O$_5$, 258.00; m/z found, 257.0 [M-H]$^-$. $^1$H NMR (400 MHz, DMSO-d$_6$); 8.10 (s, 1H), 8.21 (s, 1H), 7.81 (s, 1H), 1.99 (s, 3H).

C. 4-Acetylamino-2-chloro-5-nitrobenzamide. To a round-bottom flask containing 4-acetylamino-2-chloro-5-nitrobenzoic acid (0.10 g, 0.39 mmol) was added thionyl chloride (5 mL, 42.0 mmol). The mixture was heated at 60° C. for 3 h, and then the excess thionyl chloride was removed under reduced pressure. The residue was dissolved in tetrahydrofuran (15 mL), and ammonia gas was passed through the solution for 30 min. The reaction mixture was then concentrated and washed with water (3×5 mL) to give 89 mg (89%) of 4-acetylamino-2-chloro-5-nitrobenzamide.

HPLC: R$_t$=5.21. MS (ESI-): mass calculated for C$_9$H$_8$ClN$_3$O$_4$, 257.02; m/z found, 256.0 [M-H]$^-$.

D. 4-Amino-2-chloro-5-nitrobenzamide. To a flask containing 4-acetylamino-2-chloro-5-nitrobenzamide (0.89 g, 0.35 mmol) was added a mixture of acetic acid and hydrochloric acid (30 mL, 1:1). After stirring 3 h at 70° C., the reaction mixture was partitioned between ethyl acetate and water. The organics were then dried (MgSO$_4$) and concentrated to give 750 mg (90%) of the title compound.

HPLC: R$_t$=5.21. MS (ESI+): mass calculated for C$_7$H$_6$ClN$_3$O$_3$, 215.01; m/z found, 216.0 [M+H]$^+$.

E. 4,5-Diamino-2-chloro-benzamide. To a solution of 4-amino-2-chloro-5-nitrobenzamide (0.5 g, 2.3 mmol) in tetrahydrofuran/water/ethanol (30 mL, 1:1:1) was added Na$_2$S$_2$O$_4$ (10 mmol). The reaction mixture was stirred for 18 h and was then concentrated under reduced pressure. The residue was triterated with ethanol to give 0.41 g (95%) of crude 4,5-diamino-2-chlorobenzamide.

F. 6-Chloro-2-[4-(3,4-dichloro-phenoxy)-phenyl]-1H-benzoimidazole-5-carboxylic acid amide. To a vial containing crude 4,5-diamino-2-chloro-benzamide (30 mg, 0.16 mmol) and 4-(3,4-dichloro-phenoxy)-benzaldehyde (34 mg, 0.16 mmol) in N,N-dimethylacetamide (1 mL), was added Na$_2$S$_2$O$_5$ (52 mg, 0.28 mmol). The mixture was stirred for 4 h at 90° C. The solution was filtered, and the crude product was chromatographed (C$_{18}$, water/acetonitrile/0.01% TFA) to afford 35 mg (53%) of the title compound as a white solid (TFA salt).

HPLC: R$_t$=7.96. MS (ESI+): mass calculated for C$_{20}$H$_{12}$Cl$_3$N$_3$O$_2$, 431.00; m/z found, 432.0 [M+H]$^+$. $^1$H NMR (400 MHz, DMSO-d$_6$): 9.08-8.89 (m, 2H), 8.64 (s, 1H), 8.47 (d, J=8.8 Hz, 1H), 8.46 (s, 1H), 8.39 (s, 1H), 8.31 (br, s, 1H), 8.23 (d, J=2.7 Hz, 1H), 8.06-8.03 (m, 2H), 7.92 (dd, J=8.8, 3.1 Hz, 1H).

Example 69

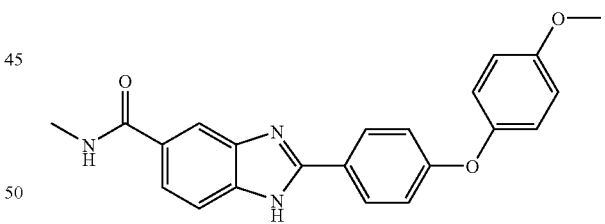

2-[4-(4-Methoxy-phenoxy)-phenyl]-1H-benzoimidazole-5-carboxylic acid methylamide.

Scheme 2. To a solution of 2-[4-(4-methoxy-phenoxy)-phenyl]-1H-benzoimidazole-5-carboxylic acid (Example 51, 50 mg, 0.13 mmol) in N,N-dimethylformamide (2 mL) was added 1,3-diisopropylcarbodiimide (32.8 mg, 0.26 mmol). The mixture was shaken 30 min at room temperature. Methylamine (1.0 mmol) was then added, and the reaction mixture was shaken for 2 h at room temperature. HPLC of the crude product (C18, water/acetonitrile/0.01% TFA) afforded 41.7 mg (85%) of a white solid (TFA salt).

HPLC: R$_t$=7.10. MS (ESI+): mass calculated for C$_{22}$H$_{19}$N$_3$O$_3$, 373.14; m/z found, 374.8 [M+H]$^+$.

Example 70

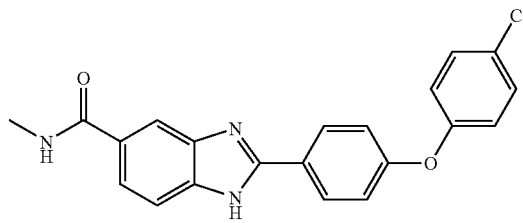

2-[4-(4-Chloro-phenoxy)-phenyl]-1H-benzoimidazole-5-carboxylic acid methylamide.

Scheme 2. To a solution of 2-[4-(4-chloro-phenoxy)-phenyl]-1H-benzoimidazole-5-carboxylic acid (Example 50, 50 mg, 0.13 mmol) in N,N-dimethylformamide (2 mL) was added 1,3-diisopropylcarbodiimide (32.8 mg, 0.26 mmol). The mixture was shaken 30 min at room temperature. Methylamine (1.0 mmol) was then added, and the reaction mixture was shaken for 2 h at room temperature. HPLC of the crude product (C18, water/acetonitrile/0.01% TFA) afforded 41.7 mg (85%) of a white solid (TFA salt).

HPLC: $R_t$=7.46. MS (ESI+): mass calculated for $C_{21}H_{16}ClN_3O_2$, 377.09; m/z found, 378.1 [M+H]$^+$. $^1$H NMR (400 MHz, DMSO-$d_6$): 8.22-8.20 (m, 1H), 7.94-7.91 (m, 2H), 7.81 (d, J=1 Hz, 1H), 7.51 (dd, J=8.5, 1.5 Hz, 1H), 7.39-7.36 (m, 2H), 7.28 (d, J=8.0 Hz, 1H), 7.16-7.12 (m, 2H), 2.17 (d, J=3.6 Hz, 3H).

Example 71

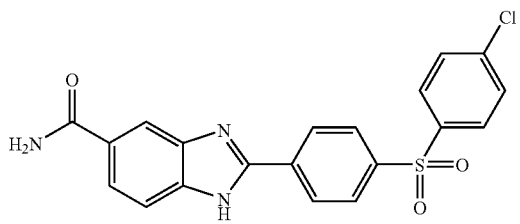

2-[4-(4-Chloro-benzenesulfonyl)-phenyl]-1H-benzoimidazole-5-carboxylic acid amide.

Scheme 6. To a flask containing a 2-[4-(4-chloro-benzenesulfonyl)-phenyl]-1H-benzoimidazole-5-carboxylic acid (Example 73, 1.0 g, 2.4 mmol) in anhydrous N,N-dimethylformamide (25 mL) was added 1,1'-carbonyldiimidazole (886 mg, 5.4 mmol). The mixture was stirred for 30 min at room temperature and was then cooled to 0° C. Ammonium carbonate (1.0 g, 10.8 mmol) was added in portions. The reaction mixture was allowed to gradually warm to room temperature over 1 h and was then stirred for an additional 24 h. The reaction mixture was then added slowly to ice water (480 mL). The resulting precipitate was collected, washed with water (3×200 mL) and dried.

HPLC: $R_t$=7.23. MS (ESI+): mass calculated for $C_{20}H_{14}ClN_3O_3S$, 411.04; m/z found 412.0 [M+H]$^+$. $^1$H NMR (400 MHz, DMSO-$d_6$): 8.42 (d, J=8.6 Hz, 2H), 8.19 (br s, 1H), 8.18 (d, J=8.6 Hz, 2H), 8.04 (d, J=8.7 Hz, 2H), 8.03 (br s, 1H), 7.83 (br d, J=8.4 Hz, 1H), 7.73 (d, J=8.7 Hz, 2H), 7.66 (br s, 1H), 7.33 (s, 1H).

Example 72

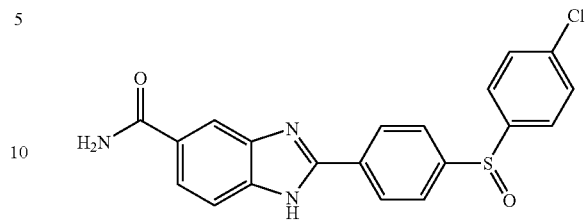

2-[4-(4-Chloro-benzenesulfinyl)-phenyl]-1H-benzoimidazole-5-carboxylic acid amide.

Scheme 6. To a flask containing a 2-[4-(4-chloro-benzenesulfinyl)-phenyl]-1H-benzoimidazole-5-carboxylic acid (Example 74, 396 mg, 1 mmol) in anhydrous N,N-dimethylformamide (11 mL) was added 1,1'-carbonyldiimidazole (369 mg, 2.28 mmol). The mixture was stirred for 30 min at room temperature and was then cooled to 0° C. Ammonium carbonate (432 mg, 4.5 mmol) was added in portions. The mixture was allowed to gradually warm to room temperature over 1 h and was then stirred for an additional 24 h. The reaction mixture was then added slowly to ice water (100 mL). The resulting precipitate was collected, washed with water (3×50 mL) and dried.

HPLC: $R_t$=6.65. MS (ESI+): mass calculated for $C_{20}H_{14}ClN_3O_2S$, 395.05; m/z found 396.0 [M+H]$^+$. $^1$H NMR (400 MHz, DMSO-$d_6$): 8.28 (d, J=8.6 Hz, 2H), 8.14 (s, 1H), 8.01 (br s, 1H), 7.91 (d, J=8.6 Hz, 2H), 7.80 (dd, J=8.0, 1.6 Hz, 1H), 7.76 (d, J=8.0 Hz, 2H), 7.63 (d, J=8.0, 1H), 7.58 (d, J=8.0, 2H), 7.32 (br s, 1H).

Example 73

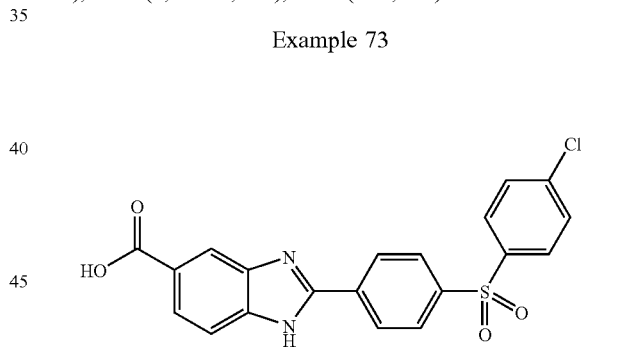

2-[4-(4-Chloro-benzenesulfonyl)-phenyl]-1H-benzoimidazole-5-carboxylic acid.

A. 4-(4-Chloro-phenylsulfanyl)-benzaldehyde. Scheme 6. To a solution of 4-chlorobenzenethiol (1.5 g, 10.4 mmol) and 4-fluorobenzaldehyde (1.03 g, 8.3 mmol) in N,N-dimethylformamide (21 mL), was added $Cs_2CO_3$ (3.4 g, 10.4 mmol). The mixture was heated to 90° C. for 24 h. The reaction mixture was cooled to room temperature, diluted with water (200 mL), and extracted with ether (3×150 mL). The combined organics were washed with 1 N NaOH (3×), water (4×), and brine. The organics were dried ($Na_2SO_4$) and concentrated to afford 2.0 g (97%) of 4-(4-Chloro-phenylsulfanyl)-benzaldehyde.

HPLC: $R_t$=10.43. $^1$H NMR (400 MHz, CDCl$_3$): 9.95 (s, 1H), 7.74 (d, J=8.6 Hz, 2H), 7.45 (d, J=8.7 Hz, 2H), 7.40 (d, J=8.7 Hz, 2H), 7.24 (d, J=8.6 Hz, 2H).

B. 2-[4-(4-Chloro-phenylsulfanyl)-phenyl]-1H-benzoimidazole-5-carboxylic acid. To a solution of 4-(4-chloro-phenylsulfanyl)-benzaldehyde (2.0 g, 8.0 mmol) and 3,4-diaminobenzoic acid (1.2 g, 8.0 mmol) in N,N-dimethylacetamide (20 mL), was added Na$_2$S$_2$O$_5$ (2.28 g, 12 mmol). The resulting mixture was heated to 100° C. for 24 h. The reaction mixture was cooled and then slowly poured onto ice water (2 L). The resulting precipitate was collected by filtration, washed with water (3×200 mL), and dried to give 2.3 g (75%) of crude 2-[4-(4-chloro-phenylsulfanyl)-phenyl]-1H-benzoimidazole-5-carboxylic acid.

C. 2-[4-(4-Chloro-benzenesulfonyl)-phenyl]-1H-benzoimidazole-5-carboxylic acid. To a flask containing 2-[4-chloro-phenylsulfanyl)-phenyl]-1H-benzoimidazole-5-carboxylic acid (100 mg, 0.26 mmol) was added oxone (480 mg, 0.78 mmol), methanol (1.0 mL) and water (1.0 mL). The mixture was stirred at room temperature for 24 h followed by collection of the resulting precipitate by filtration. The precipitate was washed with water (3×20 mL) and dried to give 105 mg (98%) of the title compound.

HPLC: R$_t$=7.75. MS (ESI+): mass calculated for C$_{20}$H$_{13}$ClN$_2$O$_4$S, 412.03; m/z found 413.0 [M+H]$^+$. $^1$H NMR (400 MHz, DMSO-d$_6$): 8.36 (d, J=8.7 Hz, 2H), 8.17 (m, 1H), 8.13 (d, J=8.7 Hz, 2H), 7.98 (d, 8.7 Hz, 2H), 7.83 (dd, J=8.5 Hz, J=1.5 Hz, 1H), 7.67 (d, J=8.7 Hz, 2H), 7.66 (m, 1H).

Example 74

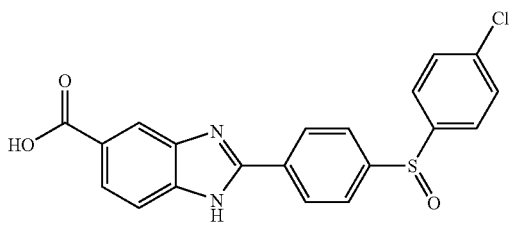

2-[4-(4-Chloro-benzenesulfinyl)-phenyl]-1H-benzoimidazole-5-carboxylic acid.

Scheme 6. To a flask containing 2-[4-(4-chloro-phenylsulfanyl)-phenyl]-1H-benzoimidazole-5-carboxylic acid (Example 73 Step B, 190 mg, 0.5 mmol) in methanol (6 mL) was added tellurium dioxide (80 mg, 0.5 mmol), 30% hydrogen peroxide (0.11 mL) and a drop of concentrated hydrochloric acid. The mixture was stirred at room temperature for 72 h. Water (10 mL) was then added, and the resulting precipitate was collected by filtration. The precipitate was washed with water (2×5 mL) and purified by reverse phase HPLC (C18; water, acetonitrile, 0.01% TFA) to give the title compound.

HPLC: R$_t$=6.99. MS (ESI+): mass calculated for C$_{20}$H$_{13}$ClN$_2$O$_3$S, 396.03; m/z found 397.0 [M+H]$^+$. $^1$H NMR (400 MHz, DMSO-d$_6$): 8.47 (d, J=8.6 Hz, 2H), 8.35 (s, 1H), 8.10 (d, J=8.6 Hz, 2H), 8.03 (dd, J=8.5, 1.5 Hz, 1H), 7.95 (d, J=8.6 Hz, 2H), 7.85 (d, J=8.5 Hz, 1H), 7.77 (d, J=8.7 Hz, 2H).

Example 75

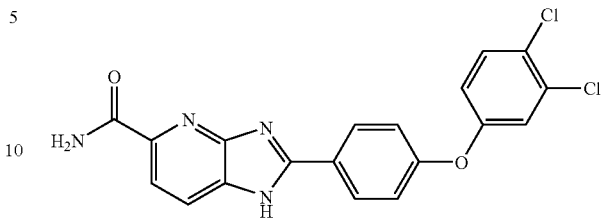

2-[4-(3,4-Dichloro-phenoxy)-phenyl]-1H-imidazo[4,5-b]pyridine-5-carboxylic acid amide.

A. 6-Methoxy-3-nitro-pyridin-2-ylamine. Scheme 8. To a glass pressure vessel was added 2-chloro-6-methoxy-3-nitro-pyridine (10.0 g, 53 mmol), ammonium carbonate (12.4 g, 159 mmol) and pyridine (100 mL). The mixture was heated at 40° C. for 24 h. The reaction mixture was concentrated in vacuo, and the residue was taken up in CH$_2$Cl$_2$ and chromatographed (silica gel; CH$_2$Cl$_2$) yielding 7.6 g (86%) of 6-methoxy-3-nitro-pyridin-2-ylamine.

HPLC: R$_t$=7.89. $^1$H NMR (400 MHz, DMSO-d$_6$): 8.26 (d, J=9.1 Hz, 1H), 8.17 (br s, 2H), 6.15 (d, J=9.1 Hz, 1H), 3.89 (s, 3H).

B. 6-Bromo-3-nitro-pyridin-2-ylamine. To a glass pressure vessel containing 6-methoxy-3-nitro-pyridin-2-ylamine (5.0 g, 29.5 mmol) was added 30% hydrogen bromide/acetic acid (60 mL). The vessel was sealed, and the contents were heated to 60° C. for 24 h. The reaction mixture was cooled, and the solvent was removed in vacuo giving 6.8 g (>95%) of crude 6-amino-5-nitro-pyridin-2-ol hydrobromide (HPLC: R$_t$=5.46). This material (2.0 g, 8.5 mmol) was taken up in toluene (30 mL), followed by phosphorus pentoxide (2.4 g, 17.0 mmol) and tetrabutyl ammonium bromide (3.2 g, 9.7 mmol). The mixture was heated to reflux for 4 h. The reaction mixture was cooled to 0° C., diluted with saturated NaHCO$_3$, and extracted with ethyl acetate (3×100 mL). The combined organics were washed with water (100 mL) and dried (Na$_2$SO$_4$) to afford 1.18 g (64%) of 6-bromo-3-nitro-pyridin-2-ylamine.

HPLC: R$_t$=8.17. $^1$H NMR (400 MHz, DMSO-d$_6$): 8.33 (br s, 2H), 8.32 (d, J=8.6 Hz, 1H), 6.96 (d, J=8.6 Hz, 1H).

C. 6-Amino-5-nitro-pyridine-2-carbonitrile. To a glass pressure vessel was added 6-bromo-3-nitro-pyridin-2-ylamine (100 mg, 0.46 mmol), copper cyanide (123 mg, 1.38 mmol) and N,N-dimethylacetamide (3.0 mL). The vessel was sealed, and the contents were heated to 120° C. for 24 h. The reaction mixture was cooled to room temperature and diluted with water (10 mL). The resulting precipitate was collected by filtration and was then stirred with CH$_2$Cl$_2$ (10 mL) for 24 h. The mixture was filtered, and the filtrate was concentrated to afford 50 mg (67%) of 6-amino-5-nitro-pyridine-2-carbonitrile.

HPLC: R$_t$=7.63. $^1$H NMR (400 MHz, DMSO-d$_6$): 8.68 (d, J=8.4 Hz, 1H), 8.27 (br s, 2H), 7.34 (d, J=8.4 Hz, 1H).

D. 2-[4-(3,4-Dichloro-phenoxy)-phenyl]-1H-imidazo[4,5-b]pyridine-5-carboxylic acid amide. A flask containing 6-amino-5-nitro-pyridine-2-carbonitrile (67 mg, 0.40 mmol), 10% palladium on carbon (catalytic) and ethanol (2.0 mL) was put under an atmosphere of H$_2$ using a balloon. The mixture was stirred at room temperature for 3 h, and filtered through a pad of celite. The filtrate was concentrated to provide crude 5,6-diamino-pyridine-2-carbonitrile. A portion of this 5,6-diamino-pyridine-2-carbonitrile (89 mg, 0.66 mmol) was treated with 4-(3,4-dichloro-phenoxy)-benzaldehyde (177 mg, 0.66 mmol), $Na_2S_2O_5$ (188 mg, 0.99 mmol) and N,N-dimethylacetamide (3.0 mL). The mixture was stirred at 120° C. for 24 h. The reaction mixture was then diluted with water (8 mL), and the resulting precipitate was collected by filtration. The crude filtrate, 2-[4-(3,4-dichlorophenoxy)-phenyl]-1H-imidazo[4,5-b]pyridine-5-carbonitrile (35 mg, 0.09 mmol), was treated with boron trifluoride/acetic acid complex (461 μL) and water (10 μL), and held at 115° C. for 30 min. The reaction mixture was cooled to room temperature and diluted with 4 N NaOH (10 mL). The resulting precipitate was collected by filtration, washed with water, and dried to provide 34 mg (94%) of the title compound.

HPLC: $R_t$=8.35. MS (ESI+): mass calculated for $C_{19}H_{12}Cl_2N_4O_2$, 398.03; m/z found 399.0 $[M+H]^+$. $^1H$ NMR (400 MHz, DMSO-$d_6$): 8.41 (d, J=8.8 Hz, 2H), 8.08 (d, J=8.2 Hz, 1H), 8.04 (br s, 1H), 7.96 (d, J=8.2 Hz, 1H), 7.75 (d, J=8.8 Hz, 1H), 7.57 (br s, 1H), 7.52 (d, J=2.8 Hz, 1H), 7.31 (d, J=8.8 Hz, 2H), 7.20 (dd, J=8.8 Hz, J=2.8 Hz, 1H).

Example 76

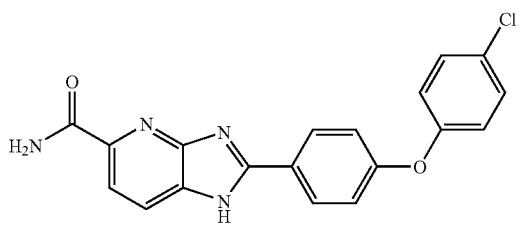

2-[4-(4-Chloro-phenoxy)-phenyl]-1H-imidazo[4,5-b]pyridine-5-carboxylic acid amide.

This compound was prepared according to the methods described in Example 75 and Scheme 8, substituting 4-(4-chloro-phenoxy)-benzaldehyde for 4-(3,4-dichloro-phenoxy)-benzaldehyde.

HPLC: $R_t$=7.91. MS (ESI+): mass calculated for $C_{19}H_{13}ClN_4O_2$, 364.07; m/z found 365.08 $[M+H]^+$. $^1H$ NMR (400 MHz, DMSO-$d_6$): 8.09 (d, J=8.8 Hz, 2H), 7.88 (d, J=8.2 Hz, 1H), 7.77-7.73 (m, 3H), 7.38 (br s, 1H), 7.31 (d, J=8.9 Hz, 2H), 7.02 (d, J=8.8 Hz, 2H), 6.98 (d, J=8.9 Hz, 2H).

Example 77

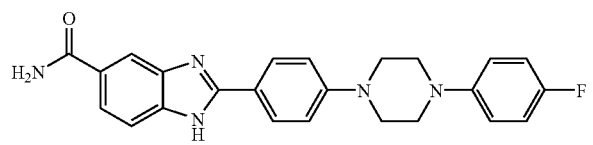

2-{4-[4-(4-Fluoro-phenyl)-piperazin-1-yl]-phenyl}-1H-benzoimidazole-5-carboxylic acid amide A. 4-[4-(4-Fluoro-phenyl)-piperazine-1-yl]-benzaldehyde. Scheme 9. To a vial containing 4-fluoro-benzaldehyde (70.0 mg, 0.56 mmol) in N,N-dimethylformamide (2 mL) was added 1-(4-fluoro-phenyl)-piperazine (100 mg, 0.56 mmol) and $Cs_2CO_3$ (368 mg, 1.13 mmol). The mixture was heated to 120° C. and was stirred for 18 h. The reaction mixture was cooled to room temperature and was then filtered, and the filtrate was purified by reverse phase HPLC (C18, acetonitrile/water, 0.05% TFA) to provide 86.4 mg (54.3%) of 4-[4-(4-fluoro-phenyl)-piperazine-1-yl]-benzaldehyde.

HPLC: $R_t$=8.75. MS (ESI+): mass calculated for $C_{17}H_{17}FN_2O$, 284.13; m/z found, 285.1 $[M+H]^+$.

B. 2-{4-[4-(4-Fluoro-phenyl)-piperazin-1-yl]-phenyl}-1H-benzoimidazole-5-carboxylic acid amide. Scheme 9. To a solution of 4-(4-fluoro-phenyl)-piperazin-1-yl]-benzaldehyde (93 mg, 0.33 mmol) in N,N-dimethylformamide (2 mL) was added 3,4-diaminobenzamide (50 mg, 0.33 mmol) followed by $Na_2S_2O_5$ (82 mg, 0.43 mmol). The mixture was heated at 100° C. for 18 h and was then cooled to room temperature. The crude reaction mixture was purified by preparative reverse phase HPLC (C18, acetonitrile/water (0.05% TFA) to give 32 mg (47%) of the title compound as a white solid (isolated as TFA salt).

HPLC: $R_t$=6.95. MS (ESI+): mass calculated for $C_{24}H_{22}FN_5O$, 415.18; m/z found, 416.2 $[M+H]^+$. $^1H$ NMR (400 MHz, DMSO-$d_6$); 8.50-8.49 (m, 1H), 8.32-8.27 (m, 3H), 8.03 (d, J=8.4 Hz, 1H), 7.51 (d, J=9.4 Hz, 2H), 7.33-7.14 (m, 4H), 3.93-3.90 (m, 4H), 3.57-3.52 (m, 4H).

Example 78

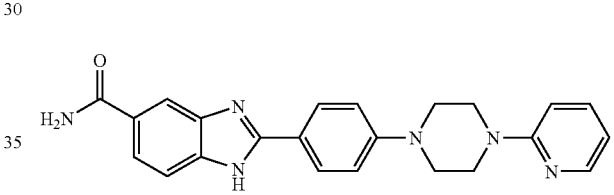

2-{4-[4-(Pyridin-2-yl)-piperazin-1-yl]-phenyl}-1H-benzoimidazole-5-carboxylic acid amide.

This compound was prepared using the methods outlined in Example 77 and Scheme 9, substituting 1-(pyridin-2-yl)-piperazine for 1-(4-fluoro-phenyl)-piperazine.

HPLC: $R_t$=5.45. MS (ESI+): mass calculated for $C_{23}H_{22}N_6O$, 398.19; m/z found, 399.2 $[M+H]^+$. $^1H$ NMR (400 MHz, DMSO-$d_6$): 8.20-8.18 (m, 4H), 7.98 (dd, J=8.6, 2 Hz, 1H), 7.75 (d, J=8.6 Hz, 2H), 7.26 (d, J=9.2 Hz, 2H), 7.13 (d, J=8.4 Hz, 1H), 6.81 (t, 6.5 Hz, 1H), 3.78-3.75 (m, 4H), 3.65-3.62 (m, 4H).

Example 79

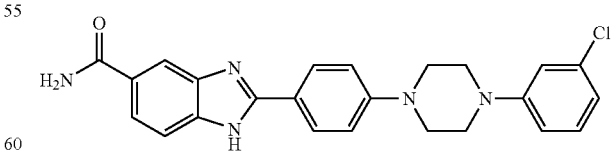

2-{4-[4-(3-Chloro-phenyl)-piperazin-1-yl]-phenyl}-1H-benzoimidazole-5-carboxylic acid amide.

This compound was prepared using the methods outlined in Example 77 and Scheme 9, substituting 1-(3-chloro-phenyl)-piperazine for 1-(4-fluoro-phenyl)-piperazine.

HPLC: $R_t$=7.70. MS (ESI+): mass calculated for $C_{24}H_{22}ClN_5O$, 431.15; m/z found, 432.1 [M+H]+. 1H NMR (400 MHz, DMSO-d6); 8.13 (d, J=1.0 Hz, 1H), 8.07 (d, J=9.0 Hz, 2H), 7.92 (dd, J=9.0, 1.3 Hz, 1H), 7.70 (d, J=8.5, Hz, 1H), 7.48-7.21 (m, 3H), 7.02-7.01 (m, 1H), 6.96 (dd, J=8.2, 2.1 Hz, 1H), 6.81 (dd, J=7.6, 2.1 Hz, 1H), 3.56-3.54 (m, 4H), 3.36-3.30 (m, 4H).

Example 80

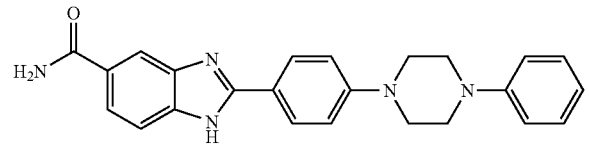

2-[4-(4-Phenyl-piperazin-1-yl)-phenyl]-1H-benzoimidazole-5-carboxylic acid amide.

This compound was prepared using the methods outlined in Example 77 and Scheme 9, substituting 1-phenyl-piperazine for 1-(4-fluoro-phenyl)-piperazine.

HPLC: $R_t$=6.69. MS (ESI+): mass calculated for $C_{24}H_{23}N_5O$, 397.19; m/z found, 398.2 [M+H]+. 1H NMR (400 MHz, DMSO-d6); 8.15 (s, 1H), 8.09 (d, J=9.1 Hz, 2H), 7.94 (dd, J=8.4, 1.2 Hz, 1H), 7.72 (d, J=8.6 Hz, 1H), 7.28-7.23 (m, 4H), 7.02 (d, J=8.6 Hz, 2H), 6.82 (t, J=6.6 Hz, 1H), 3.76-3.66 (m, 4H), 3.32-3.30 (m, 4H).

Example 81

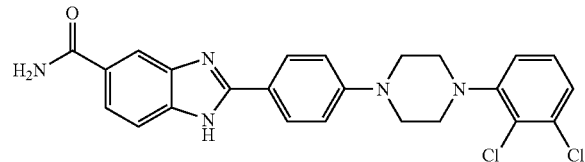

2-{4-[4-(2,3-Dichloro-phenyl)-piperazin-1-yl]-phenyl}-1H-benzoimidazole-5-carboxylic acid amide.

This compound was prepared using the methods outlined in Example 77 and Scheme 9, substituting 1-(2,3-dichlorophenyl)-piperazine for 1-(4-fluoro-phenyl)-piperazine.

HPLC: $R_t$=7.99. MS (ESI+): mass calculated for $C_{24}H_{24}Cl_2N_5O$, 465.11; m/z found, 466.1 [M+H]+.

Example 82

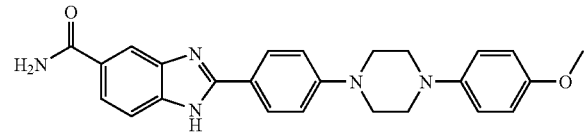

2-{4-[4-(4-Methoxy-phenyl)-piperazin-1-yl]-phenyl}-1H-benzoimidazole-5-carboxylic acid amide.

This compound was prepared using the methods outlined in Example 77 and Scheme 9, substituting 1-(4-methoxyphenyl)-piperazine for 1-(4-fluoro-phenyl)-piperazine.

HPLC: $R_t$=6.10. MS (ESI+): mass calculated for $C_{25}H_{25}N_5O_2$, 427.20; m/z found, 428.2 [M+H]+. 1H NMR (400 MHz, DMSO-d6): 8.20 (s, 1H), 8.06 (d, J=9.1 Hz, 2H), 7.96 (d, J=8.0 Hz, 2H), 7.74 (d, J=8.4 Hz, 2H), 7.52 (br s, 1H), 7.28 (d, J=9.1 Hz, 2H), 7.00 (d, J=8.8 Hz, 2H), 6.87 (d, J=8.8 Hz, 2H), 3.76 (s, 3H), 3.55-3.44 (m, 8H).

Example 83

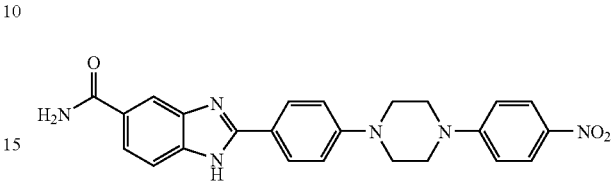

2-{4-[4-(4-Nitro-phenyl)-piperazin-1-yl]-phenyl}-1H-benzoimidazole-5-carboxylic acid amide.

This compound was prepared using the methods outlined in Example 77 and Scheme 9, substituting 1-(4-nitro-phenyl)-piperazine for 1-(4-fluoro-phenyl)-piperazine.

HPLC: $R_t$=7.20. MS (ESI+): mass calculated for $C_{24}H_{22}N_6O_3$, 442.18; m/z found, 443.0 [M+H]+.

Example 84

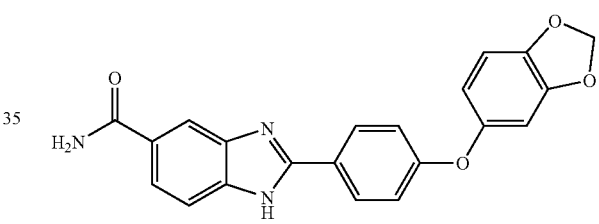

2-[4-(Benzo[1,3]dioxol-5-yloxy)-phenyl]-1H-benzoimidazole-5-carboxylic acid amide.

This compound was prepared according to the methods described in Example 1 and Scheme 2, substituting 3,4-methylenedioxyphenol for 4-chlorophenol.

HPLC: $R_t$=6.97. MS (ESI+): mass calculated for $C_{21}H_{15}N_3O_4$, 373.11; m/z found, 374.0 [M+H]+. 1H NMR (400 MHz, methanol-d4): 8.17 (s, 1H), 8.00 (d, J=8.9 Hz, 2H)), 7.93 (dd, J=8.6, 1.4 Hz, 1H), 7.69 (d, J=8.6 Hz, 1H), 7.10 (d, J=8.9 Hz, 2H), 6.79 (d, J=8.4 Hz, 1H), 6.60 (d, J=2.4 Hz, 1H), 6.52 (dd, J=2.4, 8.4 Hz, 1H), 5.93 (s, 2H).

Example 85

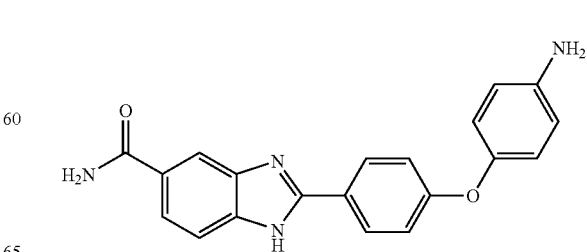

2-[4-(4-Amino-phenoxy)-phenyl]-1H-benzoimidazole-5-carboxylic acid amide.

Scheme 11. To a solution of 0.100 g (0.29 mmol) 2-[4-(4-nitro-phenoxy)-phenyl]-1H-benzoimidazole-5-carboxylic acid amide (Example 26) in 1:1 N,N-dimethylformamide (3 mL) and ethanol (3 mL), was added 10% palladium on carbon (catalytic). The mixture was stirred under an atmosphere of $H_2$ using a balloon at room temperature for 15 h and was then filtered through a pad of Celite. The filtrate was concentrated and purified by silica gel flash chromatography (eluted with 1% methanol saturated with ammonia/9% methanol/$CH_2Cl_2$) to afford 40 mg (40%) of the title compound.

HPLC: $R_t$=5.48. MS (ESI+): mass calculated for $C_{20}H_{16}N_4O_2$, 344.13; m/z found, 345.11 [M+H]$^+$. $^1$H NMR (400 MHz, $CD_3OD$): 8.40 (br s, 1H), 7.91 (d, J=8.8 Hz, 2H), 7.68 (dd, J=8.5, 1.3 Hz, 1H), 7.50 (d, J=8.7 Hz, 1H), 6.90 (d, J=8.8 Hz, 2H), 6.76 (d, J=8.8 Hz, 2H), 6.68 (d, J=8.8 Hz, 2H).

Example 86

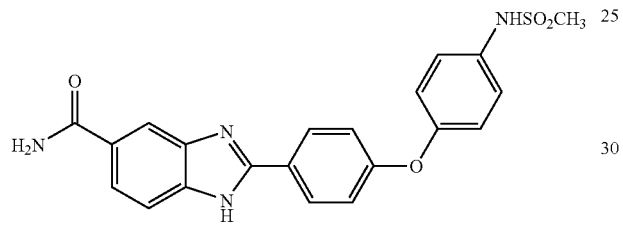

2-[4-(4-Methanesulfonylamino-phenoxy)-phenyl]-1H-benzoimidazole-5-carboxylic acid amide.

Scheme 11. To a solution of 40 mg (0.12 mmol) 2-[4-(4-amino-phenoxy)-phenyl]-1H-benzoimidazole-5-carboxylic acid amide (Example 85) in tetrahydrofuran (0.5 mL), was added pyridine (0.5 mL) followed by 0.5 mL of a 0.2 M solution of methanesulfonyl chloride in tetrahydrofuran. The mixture was stirred for 15 h at room temperature, and was concentrated and then purified by reverse phase HPLC ($C_{18}$, water/acetonitrile/0.1% TFA) to afford 10 mg (20%) of the title compound.

HPLC: $R_t$=6.45. MS (ESI+): mass calculated for $C_{21}H_{18}N_4O_4S$, 422.10; m/z found, 423.1 [M+H]$^+$. $^1$H NMR (400 MHz, $CD_3OD$): 8.18 (br s, 1H), 8.03 (d, J=8.9 Hz, 2H), 7.95 (dd, J=8.6, 1.5 Hz, 1H), 7.71 (d, J=8.6 Hz, 1H), 7.26 (d, J=8.9 Hz, 2H), 7.14 (d, J=8.9 Hz, 2H), 7.04 (d, J=8.9 Hz, 2H), 2.89 (s, 3H).

Example 87

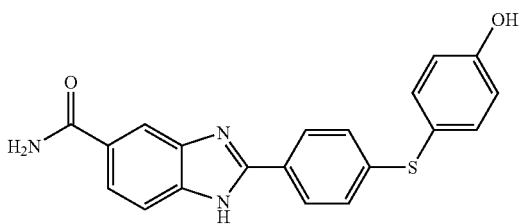

2-[4-(4-Hydroxy-phenylsulfanyl)-phenyl]-1H-benzoimidazole-5-carboxylic acid amide.

A. 2-[4-(4-Methoxy-phenylsulfanyl)-phenyl]-1H-benzoimidazole-5-carboxylic acid amide. This compound was prepared according to the methods described in Example 1 and Scheme 2, substituting 4-methoxythiophenol for 4-chlorophenol.

B. 2-[4-(4-Hydroxy-phenylsulfanyl)-phenyl]-1H-benzoimidazole-5-carboxylic acid amide. Scheme 12. To a solution of 65 mg (0.17 mmol) 2-[4-(4-methoxy-phenylsulfanyl)-phenyl]-1H-benzoimidazole-5-carboxylic acid amide in $CH_2Cl_2$ (2 mL) at −78° C., was added boron tribromide (0.2 mL, 2.1 mmol). The reaction mixture was allowed to warm to room temperature over 15 h and was then cooled to 0° C. for quenching with aqueous saturated ammonium chloride. The solid was filtered and rinsed with water to afford 60 mg (96%) of the title compound.

HPLC: $R_t$=6.70. MS (ESI+): mass calculated for $C_{20}H_{15}N_3O_2S$, 361.09; m/z found, 362.2 [M+H]$^+$. $^1$H NMR (400 MHz, $CD_3OD$): 8.19 (br s, 1H), 7.97 (dd, J=8.6, 1.4 Hz, 1H), 7.86 (d, J=8.6 Hz, 2H), 7.72 (2, J=8.6 Hz, 1H), 7.33 (d, J=8.6 Hz, 2H), 7.20 (d, J=8.6 Hz, 2H), 6.83 (d, J=8.6 Hz, 2H).

Example 88

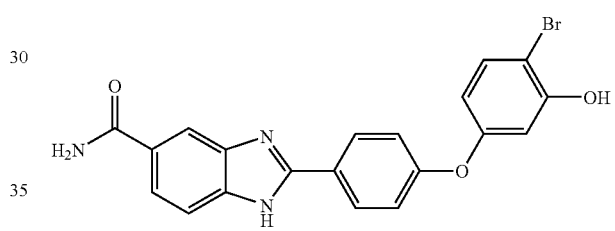

2-[4-(4-Bromo-3-hydroxy-phenoxy)-phenyl]-1H-benzoimidazole-5-carboxylic acid amide.

This compound was prepared according to the methods described in Example 87 and Scheme 12, substituting 2-[4-(4-bromo-3-methoxy-phenoxy)-phenyl]-1H-benzoimidazole-5-carboxylic acid amide for 2-[4-(4-methoxy-phenylsulfanyl)-phenyl]-1H-benzoimidazole-5-carboxylic acid amide.

HPLC: $R_t$=7.00. MS (ESI+): mass calculated for $C_{20}H_{14}BrN_3O_3$, 423.02; m/z found, 424.0 [M+H]$^+$. $^1$H NMR (400 MHz, DMSO-$d_6$): 8.18 (s, 1H), 8.03 (d, J=8.9 Hz, 2H), 7.94 (dd, J=1.6, 8.6 Hz, 1H), 7.70 (d, J=8.6 Hz, 1H), 7.42 (d, J=8.6 Hz, 1H), 7.16 (d, J=8.9 Hz, 2H), 6.58 (d, J=2.7 Hz, 1H), 6.45 (dd, J=8.6, 2.7 Hz, 1H).

Example 89

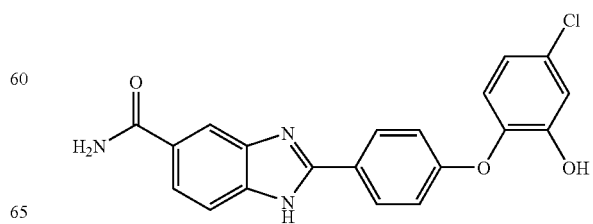

2-[4-(4-Chloro-2-hydroxy-phenoxy)-phenyl]-1H-benzoimidazole-5-carboxylic acid amide.

This compound was prepared according to the methods described in Example 87 and Scheme 12, substituting 2-[4-(4-chloro-2-methoxy-phenoxy)-phenyl]-1H-benzoimidazole-5-carboxylic acid amide for 2-[4-(4-methoxy-phenylsulfanyl)-phenyl]-1H-benzoimidazole-5-carboxylic acid amide.

HPLC: $R_t$=2.01. MS (ESI+): mass calculated for $C_{20}H_{14}ClN_3O_3$, 379.07; m/z found, 380.0 [M+H]+. $^1$H NMR (400 MHz, CD$_3$OD): 8.17 (s, 1H), 7.99 (d, J=9.0 Hz, 2H), 7.94 (dd, J=8.6, 1.6 Hz, 1H), 7.69 (d, J=8.6 Hz, 1H), 7.06 (d, J=8.9 Hz, 2H), 6.97 (d, J=8.5 Hz, 1H), 6.92 (d, J=2.4 Hz, 1H), 6.82 (dd, J=8.5, 2.4 Hz, 1H).

Example 90

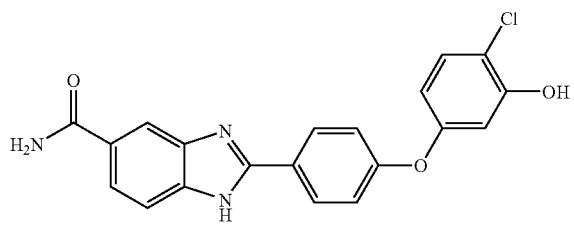

2-[4-(4-Chloro-3-hydroxy-phenoxy)-phenyl]-1H-benzoimidazole-5-carboxylic acid amide.

This compound was prepared according to the methods described in Example 87 and Scheme 12, substituting 2-[4-(4-chloro-3-methoxy-phenoxy)-phenyl]-1H-benzoimidazole-5-carboxylic acid amide for 2-[4-(4-methoxy-phenylsulfanyl)-phenyl]-1H-benzoimidazole-5-carboxylic acid amide.

HPLC: $R_t$=1.98. MS (ESI+): mass calculated for $C_{20}H_{14}ClN_3O_3$, 379.07; m/z found, 380.0 [M+H]+. $^1$H NMR (400 MHz, CD$_3$OD): 8.19 (s, 1H), 8.04 (d, J=9.0 Hz, 2H), 7.95 (dd, J=8.6, 1.6 Hz, 1H), 7.71 (d, J=8.6 Hz, 1H), 7.27 (d, J=8.7 Hz, 1H), 7.16 (d, J=8.9 Hz, 2H), 6.61 (d, J=2.7 Hz, 1H), 6.51 (d, J=8.6, 2.7 Hz, 1H).

Example 91

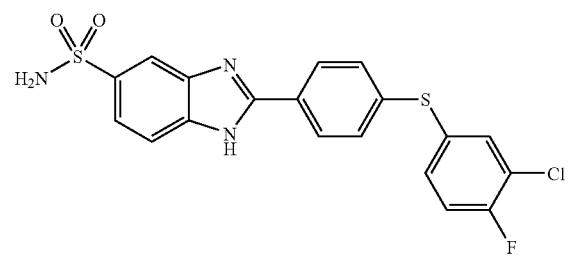

2-[4-(3-Chloro-4-fluoro-phenylsulfanyl)-phenyl]-1H-benzoimidazole-5-sulfonic acid amide.

This compound was prepared according to the methods described in Example 22 and Scheme 3, substituting 4-(3-chloro-4-fluoro-phenylsulfanyl)-benzaldehyde for 4-(4-fluoro-phenoxy)-benzaldehyde, and 3,4-diamino-benzenesulfonamide for 3,4-diaminobenzamide.

HPLC: $R_t$=8.57. MS (ESI+): mass calculated for $C_{19}H_{13}ClFN_3O_2S_2$, 433.01; m/z found, 434.0 [M+H]+, 436.0 [M+H]+. $^1$H NMR (500 MHz, CD$_3$OD): 8.23 (d, J=1.6, 1H), 8.05 (d, J=8.7, 2H), 7.96-7.94 (dd, J=8.6, 1.6, 1H), 7.81 (d, J=8.5, 1H), 7.67-7.65 (dd, J=6.9, 2.3, 1H), 7.52-7.46 (m, 1H), 7.45 (d, J=8.7, 2H), 7.35 (t, J=8.8, 1H).

Example 92

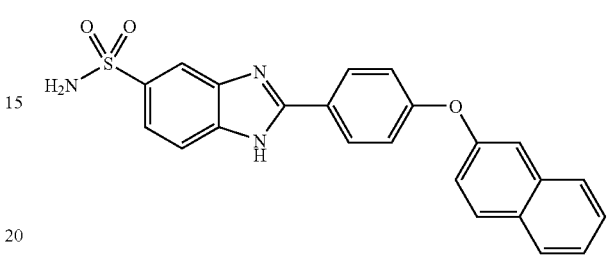

2-[4-(Naphthalen-2-yloxy)-phenyl]-1H-benzoimidazole-5-sulfonic acid amide.

This compound was prepared according to the methods described in Example 22 and Scheme 3, substituting 4-(naphthalen-2-yloxy)-benzaldehyde for 4-(4-fluoro-phenoxy)-benzaldehyde, and 3,4-diamino-benzenesulfonamide for 3,4-diaminobenzamide.

HPLC: $R_t$=8.27. MS (ESI+): mass calculated for $C_{23}H_{17}N_3O_3S$, 415.10; m/z found, 416.1 [M+H]+, 417.1 [M+H]+. $^1$H NMR (400 MHz, CD$_3$OD): 8.26 (d, J=0.9, 1H), 8.15 (d, J=8.9, 2H), 8.04-8.01 (dd, J=8.6, 1.6, 1H), 7.99 (d, J=8.9, 1H), 7.92 (d, J=7.4, 1H), 7.87 (d, J=8.6, 1H), 7.83 (d, J=7.6, 1H), 7.57 (d, J=2.3, 1H), 7.53-7.49 (m, 2H), 7.33 (d, J=2.4, 1H), 7.30 (d, J=9.0, 1H).

Example 93

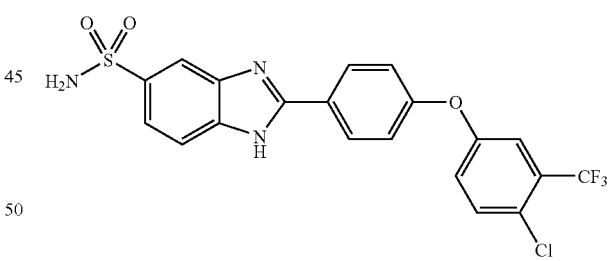

2-[4-(4-Chloro-3-trifluoromethyl-phenoxy)-phenyl]-1H-benzoimidazole-5-sulfonic acid amide.

This compound was prepared according to the methods described in Example 22 and Scheme 3, substituting 4-(4-chloro-3-trifluoromethyl-phenoxy)-benzaldehyde for 4-(4-fluoro-phenoxy)-benzaldehyde, and 3,4-diamino-benzenesulfonamide for 3,4-diaminobenzamide.

HPLC: $R_t$=8.62. MS (ESI+): mass calculated for $C_{20}H_{13}ClF_3N_3O_3S$, 467.03; m/z found, 468.0 [M+H]+, 470.0 [M+H]+. $^1$H NMR (500 MHz, CD$_3$OD): 8.14 (d, J=1.6, 1H), 8.09 (d, J=8.9, 2H), 7.87-7.85 (dd, J=8.6, 1.7, 1H), 7.73 (d, J=8.6, 1H), 7.59 (d, J=8.7, 1H), 7.42 (d, J=2.9, 1H), 7.28-7.25 (dd, J=8.6, 2.8, 1H), 7.22 (d, J=8.9, 2H).

Example 94

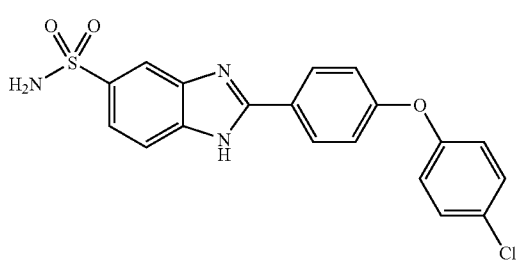

2-[4-(4-Chloro-phenoxy)-phenyl]-1H-benzoimidazole-5-sulfonic acid amide.

This compound was prepared according to the methods described in Example 22 and Scheme 3, substituting 4-(4-chloro-phenoxy)-benzaldehyde for 4-(4-fluoro-phenoxy)-benzaldehyde, and 3,4-diamino-benzenesulfonamide for 3,4-diaminobenzamide.

TLC (silica, 1% methanol saturated with ammonia/9% methanol/CH$_2$Cl$_2$): R$_f$=0.3. HPLC: R$_t$=7.68. MS (ESI+): mass calculated for C$_{19}$H$_{14}$ClN$_3$O$_3$S, 399.04; m/z found, 400.0 [M+H]$^+$. $^1$H NMR (400 MHz, CD$_3$OD): 8.18 (br s, 1H), 8.10 (d, J=8.7, 2H), 7.80 (d, J=8.5, 1H), 7.67 (br s, 1H), 7.40 (d, J=8.9, 2H), 7.15 (d, J=8.8, 2H), 7.07 (d, J=8.9, 2H).

Example 95

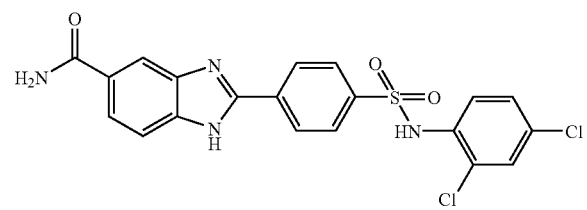

2-[4-(2,4-Dichloro-phenylsulfamoyl)-phenyl]-1H-benzoimidazole-5-carboxylic acid amide.

This compound was prepared according to the methods described in Example 58 and Scheme 4, substituting 2,5-dichloroaniline for 3,4-dichloroaniline.

TLC (silica, 1% methanol saturated with ammonia/9% methanol/CH$_2$Cl$_2$): R$_f$=0.2. HPLC: R$_t$=7.31. MS (ESI+): mass calculated for C$_{20}$H$_{14}$Cl$_2$N$_4$O$_3$S, 460.02; m/z found, 461.0 [M+H]$^+$, 463.0 [M+H]$^+$. $^1$H NMR (500 MHz, CD$_3$OD): 8.11 (d, J=8.6, 3H), 7.80 (d, J=8.6, 2H), 7.75 (d, J=8.3, 1H), 7.57 (br s, 1H), 7.45 (d, J=8.7, 1H), 7.26 (d, J=2.3, 1H), 7.24-7.22 (dd, J=8.7, 2.4, 1H).

Example 96

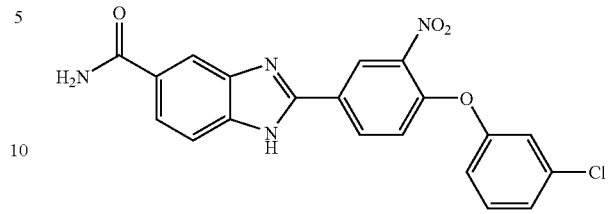

2-[4-(3-Chloro-phenoxy)-3-nitro-phenyl]-1H-benzoimidazole-5-carboxylic acid amide.

This compound was prepared according to the methods described in Example 22 and Scheme 3, substituting 4-(3-chloro-phenoxy)-3-nitro-benzaldehyde for 4-(4-fluoro-phenoxy)-benzaldehyde.

TLC (silica, 1% methanol saturated with ammonia/9% methanol/CH$_2$Cl$_2$): R$_f$=0.3. HPLC: R$_t$=2.38. MS (ESI+): mass calculated for C$_{20}$H$_{13}$ClN$_4$O$_4$, 408.06; m/z found, 409.0 [M+H]$^+$. $^1$H NMR (400 MHz, CD$_3$OD): 8.80 (d, J=1.9, 1H), 8.40-8.37 (dd, J=8.7, 2.2, 1H), 8.24 (br s, 1H), 7.89 (d, J=8.5, 1H), 7.70 (d, J=8.3, 1H), 7.48 (t, J=8.2, 1H), 7.35 (d, J=8.8, 1H), 7.31 (s, 1H), 7.25-7.24 (m, 1H), 7.14-7.11 (dd, J=8.3, 2.3, 1H).

Example 97

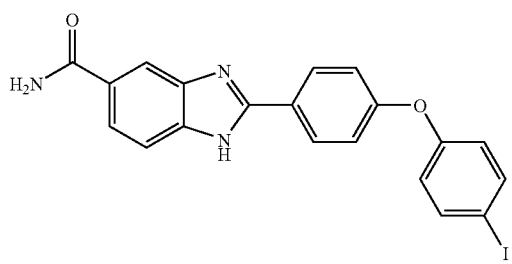

2-[4-(4-Iodo-phenoxy)-phenyl]-1H-benzoimidazole-5-carboxylic acid amide.

This compound was prepared according to the methods described in Example 1 and Scheme 2, substituting 4-iodophenol for 4-chlorophenol.

TLC (silica, 1% methanol saturated with ammonia/9% methanol/CH$_2$Cl$_2$): R$_f$=0.2. HPLC: R$_t$=7.60. MS (ESI+): mass calculated for C$_{20}$H$_{14}$IN$_3$O$_2$, 455.01; m/z found, 456.0 [M+H]$^+$. $^1$H NMR (500 MHz, CD$_3$OD): 8.07 (br s, 1H), 8.01 (d, J=8.21, 2H), 7.71 (d, J=8.3, 1H), 7.63 (d, J=8.2, 2H), 7.54-7.52 (m, 1H), 7.06 (d, J=8.0, 2H), 6.80 (d, J=8.0, 2H).

Example 98

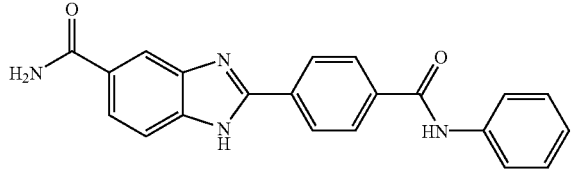

2-(4-Phenylcarbamoyl-phenyl)-1H-benzoimidazole-5-carboxylic acid amide.

A. 4-Formyl-N-phenyl-benzamide. Scheme 4. To a cooled solution of 4-formyl-benzoic acid (1.0 g, 6.6 mmol) and triethylamine (1.0 mL, 7.3 mmol) in $CH_2Cl_2$ (17 mL), was added isobutyl chloroformate (0.95 mL, 7.3 mmol) dropwise. The mixture was stirred for 40 min at 5° C. Aniline (668 µL, 7.3 mmol) was then added, and the reaction mixture was stirred for 18 h at room temperature. $CH_2Cl_2$ (50 mL) was added, and the organics were washed with water (75 mL) and brine (75 mL), dried over $Na_2SO_4$, and then filtered. The organics were concentrated under reduced pressure. The crude solid was dissolved in a minimal amount of ethyl acetate, and the product was precipitated out by the addition of hexanes (120 mL). The resulting solid was collected and dried under reduced pressure yielding 1.0 g (67%) of 4-formyl-N-phenyl-benzamide as a light yellow solid.

HPLC: $R_t$=8.2. MS (ESI+): mass calculated for $C_{14}H_{11}NO_2$, 225.08; m/z found, 224.1 [M−H]−. 1H NMR (500 MHz, $CDCl_3$): 10.11 (s, 1H), 8.04-8.00 (m, 4H), 7.84 (br s, 1H), 7.65 (d, J=7.7, 2H), 7.40 (t, J=7.6, 2H), 7.19 (t, J=7.4, 1H).

B. 2-(4-Phenylcarbamoyl-phenyl)-1H-benzoimidazole-5-carboxylic acid amide.

This compound was prepared according to the methods described in Example 22 and Scheme 3, substituting 4-formyl-N-phenyl-benzamide for 4-(4-fluoro-phenoxy)-benzaldehyde.

HPLC: $R_t$=6.57. MS (ESI+): mass calculated for $C_{21}H_{16}N_4O_2$, 356.13; m/z found, 357.1 [M+H]+. 1H NMR (500 MHz, DMSO-$d_6$+TFA): 10.45 (S, 1H), 8.32 (d, J=8.6, 2H), 8.28 (s, 1H), 8.25 (d, J=8.5, 3H), 8.07-8.05 (dd, J=8.5, 1.5, 1H), 7.88 (d, J=8.8, 1H), 7.76 (d, J=7.6, 2H), 7.55 (br s, 1H), 7.33 (t, J=7.9, 2H), 7.08 (d, J=7.4, 1H).

Example 99

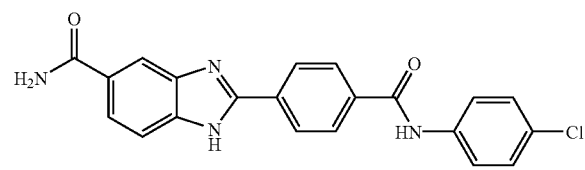

2-[4-(4-Chloro-phenylcarbamoyl)-phenyl]-1H-benzoimidazole-5-carboxylic acid amide.

This compound was prepared according to the methods described in Example 98 and Scheme 4, substituting 4-chloroaniline for aniline.

HPLC: $R_t$=7.07. MS (ESI+): mass calculated for $C_{21}H_{15}ClN_4O_2$, 390.09; m/z found, 389.2 [M−H]−. 1H NMR (400 MHz, $CD_3OD$): 8.26 (d, J 8.5, 2H), 8.20 (br s, 1H), 8.12 (d, J=8.6, 2H), 7.86-7.84 (m, 1H), 7.74 (d, J=8.8, 2H), 7.65 (br s, 1H), 7.37 (d, J=8.9, 2H).

Example 100

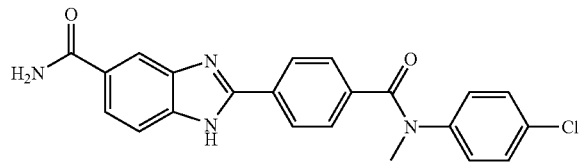

2-{4-[(4-Chloro-phenyl)-methyl-carbamoyl]-phenyl}-1H-benzoimidazole-5-carboxylic acid amide.

This compound was prepared according to the methods described in Example 98 and Scheme 4, substituting (4-chloro-phenyl)-methylamine for aniline.

TLC (silica, 1% methanol saturated with ammonia/9% methanol/$CH_2Cl_2$): $R_f$=0.3. HPLC: $R_t$=6.71. MS (ESI+): mass calculated for $C_{22}H_{17}ClN_4O_2$, 404.10; m/z found, 405.1 [M+H]+. 1H NMR (500 MHz, DMSO-$d_6$+TFA): 8.27 (s, 2H), 8.08-8.06 (m, 3H), 7.87 (d, J=8.5, 1H), 7.62 (d, J=8.0, 2H), 7.58 (br s, 1H), 7.33 (d, J=8.7, 2H), 7.29 (d, J=8.7, 2H), 3.40 (s, 3H).

Example 101

Determination of Compound Inhibition of Human Cds1 Activity

For the determination of human Cds1 activity in the presence of Cds1 inhibitory compounds, such compounds were incubated in an aqueous mixture at pH 7.4 containing 50 mM HEPES, 100 mM NaCl, 10 mM $MgCl_2$, 5 nM recombinant human Cds1, 10 µM synthetic peptide substrate SGLYRSPSMPENLNRPR having an N-terminal biotin, 1 µM Adenosine Triphosphate, 50 µCi/ml of [γ-$^{33}$P] Adenosine Triphosphate, and a protease inhibitor mixture. The reaction mixtures were incubated at 37° C. for 3 h. The peptide substrate was captured from the reaction mixture by incubating the reaction mixture with streptavidin conjugated to agarose beads and 50 mM Adenosine Triphosphate. The agarose beads were washed repeatedly with a 0.1% solution of Tween-20 in Phosphate-buffered saline, pH 7.4. Enzyme activity at different Cds1 inhibitory compound concentrations was determined by measuring the amount of radioactive phosphate bound to the substrate peptide by scintillation counting. Results are expressed as $IC_{50}$ in Table 1 below.

TABLE 1

| Cds1 Inhibition | |
|---|---|
| Example | $IC_{50}$ (nM) |
| 1 | 16 |
| 2 | 4 |
| 3 | 3 |
| 4 | 5 |
| 5 | 10 |
| 6 | 12 |
| 7 | 6 |
| 8 | 12 |
| 9 | 12 |
| 10 | 14 |
| 11 | 14 |
| 12 | 16 |
| 13 | 17 |
| 14 | 17 |
| 15 | 18 |

TABLE 1-continued

| Example | Cds1 Inhibition IC$_{50}$ (nM) |
|---|---|
| 16 | 19 |
| 17 | 23 |
| 18 | 24 |
| 19 | 26 |
| 20 | 26 |
| 21 | 28 |
| 22 | 29 |
| 23 | 31 |
| 24 | 47 |
| 25 | 72 |
| 26 | 82 |
| 27 | 108 |
| 28 | 163 |
| 29 | 715 |
| 30 | 820 |
| 31 | 633 |
| 32 | 46 |
| 33 | 60 |
| 34 | 68 |
| 35 | 68 |
| 36 | 71 |
| 37 | 191 |
| 38 | 4 |
| 39 | 10 |
| 40 | 15 |
| 41 | 7 |
| 42 | 21 |
| 43 | 26 |
| 44 | 67 |
| 45 | 53 |
| 46 | 103 |
| 47 | 209 |
| 48 | 253 |
| 49 | 277 |
| 50 | 133 |
| 51 | 276 |
| 52 | 351 |
| 53 | 445 |
| 54 | 478 |
| 55 | 270 |
| 56 | 844 |
| 57 | 289 |
| 58 | 3 |
| 59 | 10 |
| 60 | 14 |
| 61 | 15 |
| 62 | 13 |
| 63 | 29 |
| 64 | 69 |
| 65 | 652 |
| 66 | 409 |
| 67 | 6 |
| 68 | 1500 |
| 69 | 601 |
| 70 | 608 |
| 71 | 7 |
| 72 | 13 |
| 73 | 147 |
| 74 | 348 |
| 75 | 35 |
| 76 | 77 |
| 77 | 34 |
| 78 | 31 |
| 79 | 31 |
| 80 | 46 |
| 81 | 117 |
| 82 | 147 |
| 83 | 643 |
| 84 | 14 |
| 85 | 30 |
| 86 | 46 |
| 87 | 2 |
| 88 | 4 |
| 89 | 9 |
| 90 | 10 |

TABLE 1-continued

| Example | Cds1 Inhibition IC$_{50}$ (nM) |
|---|---|
| 91 | 33 |
| 92 | 46 |
| 93 | 41 |
| 94 | 55 |
| 95 | 16 |
| 96 | 11 |
| 97 | 6 |
| 98 | 410 |
| 99 | 679 |
| 100 | 896 |

Example 102

Determination of the Effect of Cds1 Inhibitory Compounds on Tumor Cell Line Clonogenic Survival Typically 3 to 300 cells from an established tumor line were plated per cm$^2$ in petri dishes in the appropriate growth medium at 37° C. Cells were exposed to compounds dissolved in the growth medium from appropriately formulated stock solutions for times ranging from 12 to 48 h. During the course of compound exposure the cells were treated with a second agent with DNA-damaging capabilities, such as ionizing radiation or certain chemotherapeutic compounds. After this treatment regimen cells were incubated in growth medium containing no compound for a period of 7 to 14 days. At that time the cells were fixed with methanol and stained with 0.25% crystal violet. The number of colonies of cells exceeding 50 cells was determined for each treatment, and this number was used to calculate the effect of compounds on the survival of cells. When cells were exposed to compound 1, a decrease in the number of colonies of cells was observed as compared to a control group having no compound 1.

Example 103

Effect of Cds1 Inhibitors on Tumor Growth in Murine Xenograft Models

One×10$^6$ to ten×10$^6$ tumor cells from an established tumor cell line are injected in the hind limbs of athymic nu/nu mice. Tumors are allowed to grow until they reach 30-100 mm$^3$. At that time mice are randomized into different treatment groups, and compound or vehicle is administered by injection or oral gavage. The mice are irradiated locally on the tumor using a radiation source such as a $^{137}$Cs irradiator. This treatment regimen is typically repeated one to three times. After this treatment tumor growth rate is followed by measurement of tumor size twice weekly in three orthogonal directions, which is used to calculate the tumor volume. The results of this procedure using Compound 1 were inconclusive.

Example 104

Determination of the Effect of Cds1 Inhibitory Compounds on Radiation-Induced Apoptosis in Isolated Primary Cells Spleen cells were isolated from C57/BL6 mice as follows: Spleens were disrupted by grinding between two frosted glass slides, and cells were passed through a cell strainer. Erythrocytes were lysed by incubation in ammonium chloride solution followed by careful washing of cells in isotonic medium. The spleen cells were plated in 60 mm petri dishes at 5×10$^6$ cells/mL in RPMI medium containing 10% fetal calf serum and Cds1 inhibitor. One hour after plating of cells with compound, the cells were dosed with 0.5-1 Gy from a $^{137}$Cs γ-radiation source. Determination of apoptotic cells by Annexin V staining was performed using the Annexin V-FITC Apoptosis Detection Kit™ (Cat# PF032 Oncogene Research Products) according to the manufacturer's instructions. Briefly, 6-24 h after irradiation, the cells were washed with buffered isotonic salt solution and suspended at 1×10$^6$ cells/mL in binding buffer (10 mM Hepes pH 7.4, 150 mM NaCl, 2.5 mM CaCl$_2$, 1 mM MgCl$_2$, 4% bovine serum albumin) containing 80 ng/mL Annexin V labelled with FITC and 0.4 µg/mL anti-B220 antibody labelled with allophycocyanin. The cells were then pelleted and resuspended in binding buffer containing 0.6 µg/mL propidium iodide. The stained cells were analyzed on a FACS machine (Fluorescence Activated Cell Sorter™, Becton Dickinson). The fraction of viable, non-apoptotic cells was determined by quantifying the number of cells that did not stain with propidium iodide or Annexin V versus the total number of cells. Fraction of non-apoptotic B-cells or total cells were determined separately based on staining with the B220 antibody mentioned above. It was found that compounds set forth in Example 1, 9, 11, 38, 42, 43, 84, 87, 88, 94, 97 and 106 (each of the three) protected spleen B cells from radiation-induced apoptosis.

Example 105

Determination of the Effect of Cds1 Inhibitory Compounds on Radiation-Induced Apoptosis in Splenocytes in vivo Female C57/BL mice, 6-8 weeks of age, were dosed by oral gavage or by injection with Cds1 inhibitory compound before and at regular intervals after radiation exposure. One to three hours after first compound dose, the animals were irradiated with γ-rays administered to the whole animal at a dose between 0.5 and 4 Gy. At times between 4 and 24 h after irradiation, the animals were sacrificed, and the tissues of interest were excised. Cell apoptosis was quantified using Annexin V staining as described in Example 104. When animals was dosed with the compound set forth in Example 1 and exposed to 4Gy radiation protection of spleen cells from apoptosis was observed compared to animals dosed with vehicle alone. Apoptosis can be studied in a variety of tissues. In some cases other metods for quantification of apoptosis than the method described in Example 104 may be more appropriate. Thus, apoptosis can also be determined by detection of DNA degradation by TUNEL staining, as described by Darzynkiewicz and Bedner (In *Analysis of Apoptotic Cells by Flow and Laser Scanning Cytometry*, Reed, J. C., Ed.; Methods of Enzymology, Vol. 322; Academic Press: San Diego, 2000; 18-39). Briefly, cells or tissues are fixed with formaldehyde and permeabilized with ethanol, and DNA ends are then labelled by attaching nucleotide derivatives such as BrdUTP using the enzyme terminal deoxynucleotidyl transferase. DNA ends can then be detected by incubating the cells or tissues with fluorescently-labelled antibodies reactive with BrdU. Quantification can be done by laser scanning cytometry, by visual microscopical examination or by FACS.

Example 106

The following compounds were made as described in Examples 1-100 and Schemes 1-12:

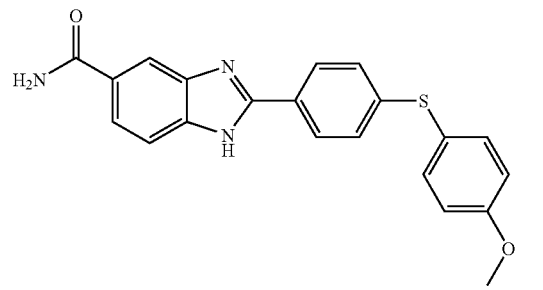

106A

2-[4-(4-Methoxy-phenylsulfanyl)-phenyl]-1H-benzoimidazole-5-carboxylic acid amide, IC$_{50}$=5 nM;

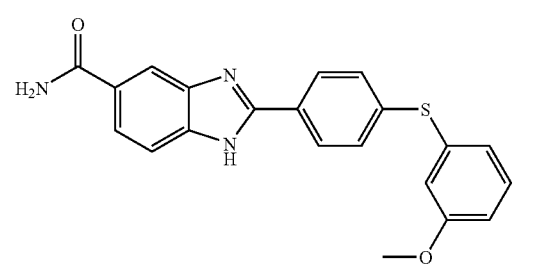

106B

2-[4-(3-Methoxy-phenylsulfanyl)-phenyl]-1H-benzoimidazole-5-carboxylic acid amide, IC$_{50}$=13 nM; and

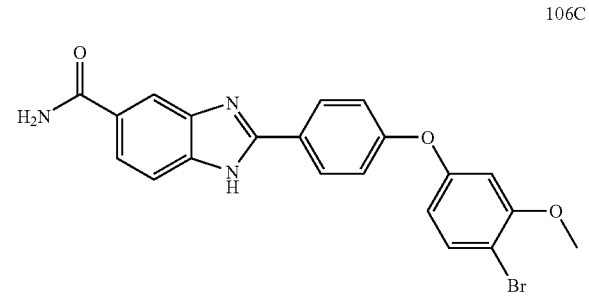

106C

2-[4-(4-Bromo-3-methoxy-phenoxy)-phenyl]-1H-benzoimidazole-5-carboxylic acid amide, IC$_{50}$=5 nM.

E. OTHER EMBODIMENTS

The features and advantages of the invention are apparent to one of ordinary skill in the art. Based on this disclosure, including the summary, detailed description, background, examples, and claims, one of ordinary skill in the art will be able to make modifications and adaptations to various conditions and usages. These other embodiments are also within the scope of the invention.

What is claimed is:

1. A compound of the formula:

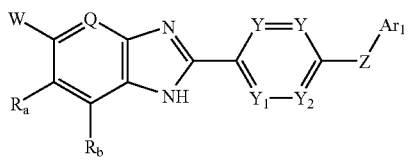

wherein
W is COOH, —(CO)NHR$^1$, or —(SO$_2$)NHR$^1$;
R$^1$ is H or C$_{1-4}$alkyl;
Q is CH;
R$_a$ and R$_b$ are H or halogen;
Y, Y$_1$ and Y$_2$ are independently selected from N and C—R$_c$ with the proviso that 0, 1 or 2 of Y, Y$_1$ and Y$_2$ are N and at least 2 of R$_c$ must be hydrogen;
R$_c$ are independently selected from the group consisting of —H, —OH, —C$_{1-6}$alkyl, —SCF$_3$, halo, —CF$_3$ and —OCF$_3$;
Z is selected from the group consisting of O, S, SO, SO$_2$, SO$_2$NR$^2$, NR$^2$SO$_2$, NH, CONR$^2$, piperazin-diyl or a covalent bond;
R$^2$ is H or C$_{1-4}$alkyl;
Ar$_1$ is selected from the group consisting of:
a) phenyl, optionally mono-, di- or tri-substituted with R$^p$;
R$^p$ is selected from the group consisting of —OH, —C$_{1-6}$alkyl, —OC$_{1-6}$alkyl, —C$_{3-6}$cycloalkyl, —OC$_{3-6}$cycloalkyl, —CN, —NO$_2$, —N(R$^y$)R$^z$ (wherein R$^y$ and R$^z$ are independently selected from H or C$_{1-6}$alkyl, or may be taken together with the nitrogen of attachment to form an otherwise aliphatic hydrocarbon ring, said ring having 5 to 7 members, optionally having one carbon replaced with >O, =N—, >NH or >N(C$_{1-4}$alkyl) and optionally having one or two unsaturated bonds in the ring), —(C=O)N(R$^y$)R$^z$, —(N—R$^t$)COR$^t$ (wherein R$^t$ is independently H or C$_{1-6}$alkyl), —(N—R$^t$)SO$_2$C$_{1-6}$alkyl, —(C=O)C$_{1-6}$alkyl, —(S=(O)$_n$)—C$_{1-6}$alkyl (wherein n is selected from 0, 1 or 2), —SO$_2$N(R$^y$)R$^z$, —SCF$_3$, halo, —CF$_3$, —OCF$_3$, —COOH, —C$_{1-6}$alkylCOOH, —COOC$_{1-6}$alkyl and —C$_{1-6}$alkylCOOC$_{1-6}$alkyl;
b) phenyl, attached at two adjacent ring members to a C$_{3-5}$alkyl moiety to form a fused 5 to 7 membered ring, said fused ring optionally having a second unsaturated bond, said fused ring optionally having one or two members replaced with, =N—, >O, >NH or >N(C$_{1-4}$alkyl) except that no such replacement is permitted where the fused ring is 5 membered and has a second unsaturated bond, and said fused ring optionally having one carbon member replaced with >C=O, the fused rings optionally mono-, di- or tri-substituted with R$^p$;
c) a monocyclic aromatic hydrocarbon group having six ring carbon atoms, having a carbon atom which is the point of attachment, having one or two carbon atoms replaced by N, and optionally mono- or di-substituted with R$^p$;
d) a monocyclic aromatic hydrocarbon group having six ring carbon atoms, having a carbon atom which is the point of attachment, having zero, one or two carbon atoms replaced by N, and having attachment at two adjacent carbon ring members to a three membered hydrocarbon moiety to form a fused five membered aromatic ring, which moiety has one carbon atom replaced by >O, >S, >NH or >N(C$_{1-4}$alkyl) and which moiety has up to one additional carbon atom optionally replaced by N, the fused rings optionally mono-, di- or tri-substituted with R$^p$;
e) a monocyclic aromatic hydrocarbon group having six ring carbon atoms, having a carbon atom which is the point of attachment, having zero, one or two carbon atoms replaced by N, and having attachment at two adjacent carbon ring members to a four membered hydrocarbon moiety to form a fused six membered aromatic ring, which moiety has zero, one or two carbon atoms replaced by N, the fused rings optionally mono-, di- or tri-substituted with R$^p$;
f) a monocyclic aromatic hydrocarbon group having five ring carbon atoms, having a carbon atom which is the point of attachment, having one carbon atom replaced by >O, >S, >NH or >N(C$_{1-4}$alkyl), having up to one additional carbon atom optionally replaced by N, and optionally mono- or di-substituted with R$^p$;
g) a monocyclic aromatic hydrocarbon group having five ring carbon atoms, having a carbon atom which is the point of attachment, having one carbon atom replaced by >O, >S, >NH or >N(C$_{1-4}$alkyl), and having attachment at two adjacent carbon ring members to a four membered hydrocarbon moiety to form a fused six membered aromatic ring, which moiety has zero, one or two carbon atoms replaced by N, the fused rings optionally mono-, di- or tri-substituted with R$^p$, provided that when W is —COOH, Z is not O; and
and enantiomers, diastereomers and pharmaceutically acceptable salts, esters or amides thereof.

2. The compound of claim 1 wherein W is COOH, —(CO)NHCH$_3$, —(CO)NH$_2$, —(SO$_2$)NHCH$_3$ or —(SO$_2$)NH$_2$.

3. The compound of claim 1 wherein W is COOH, —(CO)NH$_2$ or —(SO$_2$)NH$_2$.

4. The compound of claim 1 wherein R$_a$ and R$_b$ are independently H, Cl or F.

5. The compound of claim 1 wherein Y, Y$_1$ and Y$_2$ are C—R$_c$.

6. The compound of claim 1 wherein R$_c$ is selected from the group consisting of —H, —OH, —CH$_3$, —CH$_2$CH$_3$, —SCF$_3$, —F, —Cl, —Br, I, —CF$_3$ and —OCF$_3$.

7. The compound of claim 1 wherein R$_c$ is selected from the group consisting of H, F, Cl, CH$_3$, OCH$_3$.

8. The compound of claim 1 wherein Z is selected from the group consisting of O, S, SO, SO$_2$, SO$_2$NH, SO$_2$NCH$_3$, NHSO$_2$, NCH$_3$SO$_2$, NH, CONH, CONCH$_3$, piperazin-1,4-diyl and a covalent bond.

9. The compound of claim 1 wherein Z is selected from the group consisting of O, S, SO, SO$_2$, SO$_2$NH, NHSO$_2$, NH and CONH.

10. The compound of claim 1 wherein Z is selected from the group consisting of O, S, SO, SO$_2$ and SO$_2$NH.

11. The compound of claim 1 wherein Ar$_1$, optionally substituted with R$^p$, is selected from the group consisting of:
a) phenyl,
b) tetralin-5,6,7 or 8-yl, chroman-5,6,7 or 8-yl, benzo-1,2-pyran-5,6,7 8-yl, benzo-2,3-pyran-5,6,7 or 8-yl, coumarin-5,6,7 or 8-yl, isocoumarin-5,6,7 or 8-yl, benzo-1,3,2-benzoxazin-5,6,7 or 8-yl, benzo-1,4-dioxan-5,6,7 or 8-yl, 1,2,3,4-tetrahydroquinolin-5,6,7 or 8-yl, 1,2,3,4-tetrahydroquinoxalin-5,6,7 or 8-yl, thiochroman-5, 6,7 or 8-yl, 2,3-dihydrobenzo[1,4]dithiin-5,6,7 or 8-yl, 1,2,3,4-tetrahydroisoquinolin-5,6,7 or 8-yl, indene-4,5,6, or 7-yl, 1,2,3,4-tetrahydronapth-5,6,7, or 8 yl, 1,2-dihydroisoindolo-4,5,6, or 7-yl, 2,3-dihydroindene-4,5,6, or 7-yl, benzo-1,3-dioxol-4,5,6 or 7-yl, 2,3-dihydroindol-4,5,6 or 7-yl, 2,3-dihydrobenzofuran-4,5,6 or 7-yl, 2,3-dihydrobenzothiophen-4,5,6 or 7-yl, 2,3-dihydrobenzoimidazol-4,5,6 or 7-yl,
c) pyridinyl, pyrazinyl, pyrimidinyl, pyridazinyl,
d) benzoxazol-4,5,6 or 7-yl, benzothiophen-4,5,6 or 7-yl, benzofuran-4,5,6 or 7-yl, indol-4,5,6 or 7-yl, benzthiazol-4,5,6 or 7-yl, benzimidazo-4,5,6 or 7-yl, indazol-4,5,6 or 7-yl, 1H-pyrrolo[2,3-b]pyridin-4,5 or 6-yl, 1H-pyrrolo[3,2-c]pyridin-4,6 or 7-yl, 1H-pyrrolo[2,3-c]pyridin-4,5 or 7-yl, 1H-pyrrolo[3,2-b]pyridin-5,6 or 7-yl, purin-2-yl,
e) isoquinolin-5,6,7 or 8-yl, quinolin-5,6,7 or 8-yl, quinoxalin-5,6,7 or 8-yl, quinazolin-5,6,7 or 8-yl, naphthyridinyl,
f) furanyl, oxazolyl, isoxazolyl, thiophenyl, thiazolyl, isothiazolyl, pyrrolyl, imidazolyl, pyrazolyl, and
g) benzothiophen-2 or 3-yl, benzofuran-2 or 3-yl, indol-2 or 3yl, 1H-pyrrolo[2,3-b]pyridin-2 or 3-yl, 1H-pyrrolo[3,2-c]pyridin-2 or 3-yl, 1H-pyrrolo[2,3-c]pyridin-2 or 3-yl, 1H-pyrrolo[3,2-b]pyridin-2 or 3-yl.

12. The compound of claim 1 wherein $Ar_1$, optionally substituted with $R^p$, is selected from the group consisting of:
a) phenyl,
b) coumarin-5,6,7 or 8-yl, benzo-1,4-dioxan-5,6,7 or 8-yl, 1,2,3,4-tetrahydroquinolin-5,6,7 or 8-yl, or 8-yl, 1,2,3,4-tetrahydroisoquinolin-5,6,7 or 8-yl, indene-4,5,6, or 7-yl, 1,2,3,4-tetrahydronapth-5,6,7, or 8 yl, 1,2-dihydroisoindolo-4,5,6, or 7-yl, 2,3-dihydroindene-4,5,6, or 7-yl, benzo-1,3-dioxol-4,5,6 or 7-yl, 2,3-dihydroindol-4,5,6 or 7-yl, 2,3-dihydrobenzofuran-4,5,6 or 7-yl, 2,3-dihydrobenzothiophen-4,5,6 or 7-yl,
c) pyridinyl, pyrazinyl, pyrimidinyl, pyridazinyl,
d) benzothiophen-4,5,6 or 7-yl, benzofuran-4,5,6 or 7-yl, indol-4,5,6 or 7-yl,
e) isoquinolin-5,6,7 or 8-yl, quinolin-5,6,7 or 8-yl,
f) furanyl, oxazolyl, isoxazolyl, thiophenyl, thiazolyl, isothiazolyl, pyrrolyl, imidazolyl, pyrazolyl, and
g) benzothiophen-2 or 3-yl, benzofuran-2 or 3-yl, indol-2 or 3-yl.

13. The compound of claim 1 wherein $Ar^1$, optionally substituted with $R^p$, is selected from the group consisting of: phenyl, benzo-1,4-dioxan-5,6,7 or 8-yl, indene-4,5,6, or 7-yl, 1,2,3,4-tetrahydronapth-5,6,7, or 8 yl, 2,3-dihydroindene-4, 5,6, or 7-yl, benzo-1,3-dioxol-4,5,6 or 7-yl, 2,3-dihydroindol-4,5,6 or 7-yl, 2,3-dihydrobenzofuran-4,5,6 or 7-yl, 2,3-dihydrobenzothiophen-4,5,6 or 7-yl, pyridinyl, benzothiophen-4,5,6 or 7-yl, benzofuran-4,5,6 or 7-yl, indol-4,5,6 or 7-yl, furanyl, thiophenyl, pyrrolyl, pyrazolyl, and benzothiophen-2 or 3-yl, benzofuran-2 or 3-yl and indol-2 or 3yl.

14. The compound of claim 1 wherein $Ar_1$, including the $R^p$ substituent, is selected from the group consisting of pyridyl, phenyl, naphthyl, 4-chloro phenyl, 4-methyl-3-chloro phenyl, 4-chloro-3-trifluoromethyl phenyl, 3,4-dichloro phenyl, 3-chloro-4-fluoro phenyl, 2-flouro-5-trifluoromethyl, 4-chloro-3-fluoro phenyl, 3,4-dimethyl phenyl, 2-napthyl, 4-trifluoromethyl phenyl, 4-bromo phenyl, 4-fluoro-3-methyl phenyl, 3-chloro phenyl, tetrahydronapthyl, 5-chloro-2-methyl phenyl, 3-trifluoromethyl phenyl, 4-methoxy phenyl, 4-methyl phenyl, 2-fluoro-3-trifluoromethyl phenyl, 2-chloro-4-methyl phenyl, 4-ethyl phenyl, 4-fluoro phenyl, 3,4-dimethoxy phenyl, 3-(dimethylamino) phenyl, 4-nitro phenyl, 4-cyano phenyl, 2-methoxy-4-methyl phenyl, 4-trifluoromethoxy phenyl, 2-chloro phenyl, 4-morpholino phenyl, 3-chloro phenyl, 2,3-dichloro phenyl, benzo[1,3]dioxolyl, 4-amino phenyl, 4-hydroxy phenyl, 4-bromo-3-hydroxy phenyl, 4-chloro-2-hydroxy phenyl, 4-chloro-3-hydroxy phenyl, 2,4-dichloro phenyl, 4-bromo-3-methoxy phenyl and 4-iodo phenyl.

15. The compound of claim 1 wherein $R^p$ is selected from the group consisting of —OH, —CH₃, —CH₂CH₃, —OCH₃, —OCH₂CH₃, —OCH(CH₃)₂, cyclopropyl, cyclobutyl, cyclopentyl, cyclohexyl, -Ocyclopentyl, -Ocyclohexyl, —CN, —NO₂, —C(O)NH₂, —C(O)N(CH₃)₂, —C(O)NH(CH₃), —NHCOCH₃, —NCH₃COCH₃, —NHSO₂CH₃, —NCH₃SO₂CH₃, —C(O)CH₃, —SOCH₃, —SO₂CH₃, —SO₂NH₂, —SO₂NHCH₃, —SO₂N(CH₃)₂, —SCF₃, —F, —Cl, —Br, I, —CF₃, —OCF₃, —COOH, —COOCH₃, —COOCH₂CH₃, —NH₂, —NHCH₃, —N(CH₃)₂, —N(CH₂CH₃)₂, —NCH₃(CH(CH₃)₂), imidazolidin-1-yl, 2-imidazolin-1-yl, pyrazolidin-1-yl, piperidin-1-yl, 2- or 3-pyrrolin-1-yl, 2-pyrazolinyl, morpholin-4-yl, thiomorpholin-4-yl, piperazin-1-yl, pyrrolidin-1-yl, homopiperidin-1-yl.

16. The compound of claim 1 wherein $R^p$ is selected from the group consisting of H, —OH, OCH₃, OCF₃, —CH₃, —CH₂CH₃, —CF₃, —F, —Cl, —Br, —I, —NH₂, —N(CH₃)₂, morpholin-4-yl, —NO₂, CN, —C(O)NH₂, —COOH, —NHSO₂CH₃, —SO₂NH₂.

17. A compound selected from the group consisting of:

| EX | Compound Name |
|---|---|
| 1 | 2-[4-(4-chloro-phenoxy)-phenyl]-1H-benzoimidazole-5-carboxylic acid amide |
| 2 | 2-[4-(3-chloro-4-methyl-phenoxy)-phenyl]-1H-benzoimidazole-5-carboxylic acid amide |
| 3 | 2-[4-(4-chloro-3-trifluoromethyl-phenoxy)-phenyl]-1H-benzoimidazole-5-carboxylic acid amide |
| 4 | 2-[4-(3,4-dichloro-phenoxy)-phenyl]-1H-benzoimidazole-5-carboxylic acid amide |
| 5 | 2-[4-(3-chloro-4-fluoro-phenoxy)-phenyl]-1H-benzoimidazole-5-carboxylic acid amide |
| 6 | 2-[4-(2-fluoro-5-trifluoromethyl-phenoxy)-phenyl]-1H-benzoimidazole-5-carboxylic acid amide |
| 7 | 2-[4-(4-chloro-3-fluoro-phenoxy)-phenyl]-1H-benzoimidazole-5-carboxylic acid amide |
| 8 | 2-[4-(3,4-dimethyl-phenoxy)-phenyl]-1H-benzoimidazole-5-carboxylic acid amide |
| 9 | 2-[4-(2-naphthyloxy)-phenyl]-1H-benzoimidazole-5-carboxylic acid amide |
| 10 | 2-[4-(4-trifluoromethyl-phenoxy)-phenyl]-1H-benzoimidazole-5-carboxylic acid amide |
| 11 | 2-[4-(4-bromo-phenoxy)-phenyl]-1H-benzoimidazole-5-carboxylic acid amide |
| 12 | 2-[4-(4-fluoro-3-methyl-phenoxy)-phenyl]-1H-benzoimidazole-5-carboxylic acid amide |
| 13 | 2-[4-(3-chloro-phenoxy)-phenyl]-1H-benzoimidazole-5-carboxylic acid amide |
| 14 | 2-[4-(5,6,7,8-tetrahydro-naphthalen-2-yloxy)-phenyl]-1H-benzoimidazole-5-carboxylic acid amide |
| 15 | 2-[4-(5-chloro-2-methyl-phenoxy)-phenyl]-1H-benzoimidazole-5-carboxylic acid amide |
| 16 | 2-[4-(3-trifluoromethyl-phenoxy)-phenyl]-1H-benzoimidazole-5-carboxylic acid amide |
| 17 | 2-[4-(4-methoxy-phenoxy)-phenyl]-1H-benzoimidazole-5-carboxylic acid amide |
| 18 | 2-[4-(4-methyl-phenoxy)-phenyl]-1H-benzoimidazole-5-carboxylic acid amide |
| 19 | 2-[4-(2-fluoro-3-trifluoromethyl-phenoxy)-phenyl]-1H-benzoimidazole-5-carboxylic acid amide |
| 20 | 2-[4-(2-chloro-4-methyl-phenoxy)-phenyl]-1H-benzoimidazole-5-carboxylic acid amide |
| 21 | 2-[4-(4-ethyl-phenoxy)-phenyl]-1H-benzoimidazole-5-carboxylic acid amide |

| EX | Compound Name |
|---|---|
| 22 | 2-[4-(4-fluoro-phenoxy)-phenyl]-1H-benzoimidazole-5-carboxylic acid amide |
| 23 | 2-[4-(3,4-dimethoxy-phenoxy)-phenyl]-1H-benzoimidazole-5-carboxylic acid amide |
| 24 | 2-[4-(4-carbamoyl-phenoxy)-phenyl]-1H-benzoimidazole-5-carboxylic acid amide |
| 25 | 2-[4-(3-(N,N-dimethyl)amino-phenoxy)-phenyl]-1H-benzoimidazole-5-carboxylic acid amide |
| 26 | 2-[4-(4-nitro-phenoxy)-phenyl]-1H-benzoimidazole-5-carboxylic acid amide |
| 27 | 2-[4-(4-cyano-phenoxy)-phenyl]-1H-benzoimidazole-5-carboxylic acid amide |
| 28 | 3-{4-[4-(5-carbamoyl-1H-benzoimidazol-2-yl)-phenoxy]-phenyl}-propionic acid |
| 29 | 2-[4-(3-carboxy-phenoxy)-phenyl]-1H-benzoimidazole-5-carboxylic acid amide |
| 30 | 2-[4-(3-diethylcarbamoyl-phenoxy)-phenyl]-1H-benzoimidazole-5-carboxylic acid amide |
| 31 | 2-[4-(3-pyridyloxy)-phenyl]-1H-benzoimidazole-5-carboxylic acid amide |
| 32 | 2-[3-chloro-4-(3,4-dimethoxy-phenoxy)-phenyl]-1H-benzoimidazole-5-carboxylic acid amide |
| 33 | 2-[2-chloro-4-(4-chloro-phenoxy)-phenyl]-1H-benzoimidazole-5-carboxylic acid amide |
| 34 | 2-[3-chloro-4-(4-fluoro-3-methyl-phenoxy)-phenyl]-1H-benzoimidazole-5-carboxylic acid amide |
| 35 | 2-[3-chloro-4-(2-methoxy-4-methyl-phenoxy)-phenyl]-1H-benzoimidazole-5-carboxylic acid amide |
| 36 | 2-[3-chloro-4-(3-chloro-4-methyl-phenoxy)-phenyl]-1H-benzoimidazole-5-carboxylic acid amide |
| 37 | 2-(6-p-tolyloxy-pyridin-3-yl)-1H-benzoimidazole-5-carboxylic acid amide |
| 38 | 2-[4-(3-chloro-4-fluoro-phenylsulfanyl)-phenyl]-1H-benzoimidazole-5-carboxylic acid amide |
| 39 | 2-[4-(4-ethyl-phenylsulfanyl)-phenyl]-1H-benzoimidazole-5-carboxylic acid amide |
| 40 | 2-[4-(3,4-dimethoxy-phenylsulfanyl)-phenyl]-1H-benzoimidazole-5-carboxylic acid amide |
| 41 | 2-[4-(4-chloro-phenylsulfanyl)-phenyl]-1H-benzoimidazole-5-carboxylic acid amide |
| 42 | 2-[6-(4-chloro-phenylsulfanyl)-pyridin-3-yl]-1H-benzoimidazole-5-carboxylic acid amide |
| 43 | 2-[6-(4-methyl-phenylsulfanyl)-pyridin-3-yl]-1H-benzoimidazole-5-carboxylic acid amide |
| 44 | 2-[4-(4-trifluoromethoxy-phenylsulfanyl)-phenyl]-1H-benzoimidazole-5-carboxylic acid amide |
| 45 | 2-[4-(4-fluoro-phenyl)-phenyl]-1H-benzoimidazole-5-carboxylic acid amide |
| 46 | 2-[4-phenyl-phenyl]-1H-benzoimidazole-5-carboxylic acid amide |
| 47 | 2-[4-(2-chloro-phenyl)-phenyl]-1H-benzoimidazole-5-carboxylic acid amide |
| 48 | 2-[4-(4-chloro-phenyl)-phenyl]-1H-benzoimidazole-5-carboxylic acid amide |
| 49 | 2-[4-(2-pyridyl)-phenyl]-1H-benzoimidazole-5-carboxylic acid amide |
| 50 | 2-[4-(4-chloro-phenoxy)-phenyl]-1H-benzoimidazole-5-carboxylic acid |
| 51 | 2-[4-(4-methoxy-phenoxy)-phenyl]-1H-benzoimidazole-5-carboxylic acid |
| 52 | 2-[4-(4-fluoro-phenoxy)-phenyl]-1H-benzoimidazole-5-carboxylic acid |
| 53 | 2-[2-chloro-4-(4-chloro-phenoxy)-phenyl]-1H-benzoimidazole-5-carboxylic acid |
| 54 | 2-[4-(4-nitro-phenoxy)-phenyl]-1H-benzoimidazole-5-carboxylic acid |
| 55 | 2-[4-(4-chloro-phenyl)-phenyl]-1H-benzoimidazole-5-carboxylic acid |
| 56 | 2-(4-phenoxy-phenyl)-1H-benzoimidazole-5-carboxylic acid |
| 57 | 2-(4-phenoxy-phenyl)-1H-benzoimidazole-5-sulfonic acid amide |
| 58 | 2-[4-(3,4-dichloro-phenylsulfamoyl)-phenyl]-1H-benzoimidazole-5-carboxylic acid amide |
| 59 | 2-[4-(4-chloro-phenylsulfamoyl)-phenyl]-1H-benzoimidazole-5-carboxylic acid amide |
| 60 | 2-[4-(4-nitro-phenylsulfamoyl)-phenyl]-1H-benzoimidazole-5-carboxylic acid amide |
| 61 | 2-[4-(4-bromo-phenylsulfamoyl)-phenyl]-1H-benzoimidazole-5-carboxylic acid amide |
| 62 | 2-[4-(4-trifluoromethyl-phenylsulfamoyl)-phenyl]-1H-benzoimidazole-5-carboxylic acid amide |
| 63 | 2-[4-(2-naphthylsulfamoyl)-phenyl]-1H-benzoimidazole-5-carboxylic acid amide |
| 64 | 2-[4-(4-methoxy-phenylsulfamoyl)-phenyl]-1H-benzoimidazole-5-carboxylic acid amide |
| 65 | 2-{4-[(4-chloro-phenyl)-methyl-sulfamoyl]-phenyl}-1H-benzoimidazole-5-carboxylic acid amide |
| 66 | 2-[4-(4-morpholino-4-yl-phenylsulfamoyl)-phenyl]-1H-benzoimidazole-5-carboxylic acid amide |
| 67 | 2-[4-(3,4-dichloro-benzenesulfonylamino)-phenyl]-1H-benzoimidazole-5-carboxylic acid amide |
| 68 | 6-chloro-2-[4-(3,4-dichloro-phenoxy)-phenyl]-1H-benzoimidazole-5-carboxylic acid amide |
| 69 | 2-[4-(4-methoxy-phenoxy)-phenyl]-1H-benzoimidazole-5-carboxylic acid methylamide |
| 70 | 2-[4-(4-chloro-phenoxy)-phenyl]-1H-benzoimidazole-5-carboxylic acid methylamide |
| 71 | 2-[4-(4-chloro-benzenesulfonyl)-phenyl]-1H-benzoimidazole-5-carboxylic acid amide |
| 72 | 2-[4-(4-chloro-benzenesulfinyl)-phenyl]-1H-benzoimidazole-5-carboxylic acid amide |
| 73 | 2-[4-(4-chloro-benzenesulfonyl)-phenyl]-1H-benzoimidazole-5-carboxylic acid |
| 74 | 2-[4-(4-chloro-benzenesulfinyl)-phenyl]-1H-benzoimidazole-5-carboxylic acid |
| 75 | 2-[4-(3,4-dichloro-phenoxy)-phenyl]-1H-imidazo[4,5-b]pyridine-5-carboxylic acid amide |
| 76 | 2-[4-(4-chloro-phenoxy)-phenyl]-1H-imidazo[4,5-b]pyridine-5-carboxylic acid amide |
| 77 | 2-{4-[4-(4-fluoro-phenyl)-piperazin-1-yl]-phenyl}-1H-benzoimidazole-5-carboxylic acid amide |
| 78 | 2-{4-[4-(pyridin-2-yl)-piperazin-1-yl]-phenyl}-1H-benzoimidazole-5-carboxylic acid amide |
| 79 | 2-{4-[4-(3-chloro-phenyl)-piperazin-1-yl]-phenyl}-1H-benzoimidazole-5-carboxylic acid amide |
| 80 | 2-[4-(4-phenyl-piperazin-1-yl)-phenyl]-1H-benzoimidazole-5-carboxylic acid amide |
| 81 | 2-{4-[4-(2,3-dichloro-phenyl)-piperazin-1-yl]-phenyl}-1H-benzoimidazole-5-carboxylic acid amide |
| 82 | 2-{4-[4-(4-methoxy-phenyl)-piperazin-1-yl]-phenyl}-1H-benzoimidazole-5-carboxylic acid amide |
| 83 | 2-{4-[4-(4-nitro-phenyl)-piperazin-1-yl]-phenyl}-1H-benzoimidazole-5-carboxylic acid amide |
| 84 | 2-[4-(benzo[1,3]dioxol-5-yloxy)-phenyl]-1H-benzoimidazole-5-carboxylic acid amide |
| 85 | 2-[4-(4-amino-phenoxy)-phenyl]-1H-benzoimidazole-5-carboxylic acid amide |
| 86 | 2-[4-(4-methanesulfonylamino-phenoxy)-phenyl]-1H-benzoimidazole-5-carboxylic acid amide |
| 87 | 2-[4-(4-hydroxy-phenylsulfanyl)-phenyl]-1H-benzoimidazole-5-carboxylic acid amide |
| 88 | 2-[4-(4-bromo-3-hydroxy-phenoxy)-phenyl]-1H-benzoimidazole-5-carboxylic acid amide |
| 89 | 2-[4-(4-chloro-2-hydroxy-phenoxy)-phenyl]-1H-benzoimidazole-5-carboxylic acid amide |
| 90 | 2-[4-(4-chloro-3-hydroxy-phenoxy)-phenyl]-1H-benzoimidazole-5-carboxylic acid amide |
| 91 | 2-[4-(3-chloro-4-fluoro-phenylsulfanyl)-phenyl]-1H-benzoimidazole-5-sulfonic acid amide |
| 92 | 2-[4-(naphthalen-2-yloxy)-phenyl]-1H-benzoimidazole-5-sulfonic acid amide |
| 93 | 2-[4-(4-chloro-3-trifluoromethyl-phenoxy)-phenyl]-1H-benzoimidazole-5-sulfonic acid amide |
| 94 | 2-[4-(4-chloro-phenoxy)-phenyl]-1H-benzoimidazole-5-sulfonic acid amide |
| 95 | 2-[4-(2,4-dichloro-phenylsulfamoyl)-phenyl]-1H-benzoimidazole-5-carboxylic acid amide |
| 96 | 2-[4-(3-chloro-phenoxy)-3-nitro-phenyl]-1H-benzoimidazole-5-carboxylic acid amide |
| 97 | 2-[4-(4-iodo-phenoxy)-phenyl]-1H-benzoimidazole-5-carboxylic acid amide |
| 98 | 2-(4-phenylcarbamoyl-phenyl)-1H-benzoimidazole-5-carboxylic acid amide |
| 99 | 2-[4-(4-chloro-phenylcarbamoyl)-phenyl]-1H-benzoimidazole-5-carboxylic acid amide |

-continued

| EX | Compound Name |
|---|---|
| 100 | 2-{4-[(4-chloro-phenyl)-methyl-carbamoyl]-phenyl}-1H-benzoimidazole-5-carboxylic acid amide |
| 106A | 2-[4-(4-Methoxy-phenylsulfanyl)-phenyl]-1H-benzoimidazole-5-carboxylic acid amide |
| 106B | 2-[4-(3-Methoxy-phenylsulfanyl)-phenyl]-1H-benzoimidazole-5-carboxylic acid amide and |
| 106C | 2-[4-(4-Bromo-3-methoxy-phenoxy)-phenyl]-1H-benzoimidazole-5-carboxylic acid amide. |

18. A compound selected from the group consisting of: 2-[6-(4-chloro-phenoxy)-pyridazin-3-yl]-3H-benzoimidazole-5-carboxylic acid amide; 2-[4-(4-chloro-phenylamino)-phenyl]-3H-benzoimidazole-5-carboxylic acid amide; 2-[4-(4-chloro-3-dimethylamino-phenoxy)-phenyl]-3H-benzoimidazole-5-carboxylic acid amide; 2-[4-(4-chloro-3-methanesulfonylamino-phenoxy)-phenyl]-3H-benzoimidazole-5-carboxylic acid amide; 2-[4-(4-chloro-3-sulfamoyl-phenoxy)-phenyl]-3H-benzoimidazole-5-carboxylic acid amide; 2-[3-chloro-4-(4-chloro-phenylsulfamoyl)-phenyl]-3H-benzoimidazole-5-carboxylic acid amide; 2-[6-(4-chloro-phenylsulfamoyl)-pyridin-3-yl]-3H-benzoimidazole-5-carboxylic acid amide; 2-[6-(3,4-dichloro-phenylsulfamoyl)-pyridin-3-yl]-3H-benzoimidazole-5-carboxylic acid amide; 2-[6-(2,4-dichloro-phenylsulfamoyl)-pyridin-3-yl]-3H-benzoimidazole-5-carboxylic acid amide; and 2-[6-(4-chloro-benzenesulfonylamino)-pyridin-3-yl]-3H-benzoimidazole-5-carboxylic acid amide.

* * * * *